US011291807B2

(12) United States Patent
Eigler et al.

(10) Patent No.: US 11,291,807 B2
(45) Date of Patent: Apr. 5, 2022

(54) ASYMMETRIC SHUNT FOR REDISTRIBUTING ATRIAL BLOOD VOLUME

(71) Applicant: V-Wave Ltd., Caesarea (IL)

(72) Inventors: Neal Eigler, Malibu, CA (US); James Whiting, Los Angeles, CA (US); Nir Nae, Binyamina (IL)

(73) Assignee: V-Wave Ltd., Caesarea (IL)

( * ) Notice: Subject to any disclaimer, the term of this patent is extended or adjusted under 35 U.S.C. 154(b) by 510 days.

(21) Appl. No.: 16/408,419

(22) Filed: May 9, 2019

(65) Prior Publication Data
US 2019/0262118 A1    Aug. 29, 2019

Related U.S. Application Data

(63) Continuation-in-part of application No. 16/130,988, filed on Sep. 13, 2018, now Pat. No. 10,925,706,
(Continued)

(51) Int. Cl.
*A61M 27/00* (2006.01)
*A61F 2/01* (2006.01)
(Continued)

(52) U.S. Cl.
CPC ............ *A61M 27/002* (2013.01); *A61F 2/01* (2013.01); *A61F 2/2487* (2013.01); *A61F 2/91* (2013.01);
(Continued)

(58) Field of Classification Search
CPC ..... A61M 27/002; A61M 27/006; A61F 2/01; A61F 2/2478; A61F 2/91;
(Continued)

(56) References Cited

U.S. PATENT DOCUMENTS 3,852,334 A    12/1974 Dusza et al.
3,874,388 A    4/1975 King et al.
(Continued)

FOREIGN PATENT DOCUMENTS

AU    2003291117 B2    4/2009
CA    2378920 A1    2/2001
(Continued)

OTHER PUBLICATIONS

Abraham et al., "Hemodynamic Monitoring in Advanced Heart Failure: Results from the LAPTOP-HF Trial," J Card Failure, 22:940 (2016) (Abstract Only).
(Continued)

*Primary Examiner* — Philip R Wiest
(74) *Attorney, Agent, or Firm* — Eversheds Sutherland (US) LLP; Christopher C. Bolten; Nicola A. Pisano

(57) ABSTRACT

An asymmetric device for regulating blood volume distribution across a patient's atrial septum having a first expandable end region and a second expandable end region. The first expandable end region is transitionable from a contracted delivery state to an expanded deployed state in which the first expandable end region extends into the patient's left atrium and an inlet end of the first expandable end region is in a first plane. The second expandable end region is transitionable from a contracted delivery state to an expanded deployed state in which the second expandable end region extends into the patient's right atrium and an outlet end of the second expandable end region is in a second plane, such that the first plane intersects the second plane. The device further includes a neck region joining the first expandable end region to the second expandable end region, wherein the neck region is sized and shaped for placement in the patient's atrial septum.

20 Claims, 8 Drawing Sheets

Related U.S. Application Data which is a continuation of application No. 15/449,834, filed on Mar. 3, 2017, now Pat. No. 10,076,403.

(51) Int. Cl.
  *A61F 2/24* (2006.01)
  *A61F 2/91* (2013.01)

(52) U.S. Cl.
  CPC ... *A61F 2002/249* (2013.01); *A61F 2230/001* (2013.01); *A61F 2230/0013* (2013.01); *A61F 2230/0054* (2013.01); *A61F 2250/0039* (2013.01); *A61F 2250/0051* (2013.01); *A61F 2250/0098* (2013.01)

(58) Field of Classification Search
  CPC .......... A61F 2002/249; A61F 2230/001; A61F 2230/0013; A61F 2250/0039; A61F 2250/0051; A61F 2250/0098
  See application file for complete search history.

(56) References Cited

U.S. PATENT DOCUMENTS

| | | |
|---|---|---|
| 3,952,334 A | 4/1976 | Bokros et al. |
| 4,484,955 A | 11/1984 | Hochstein |
| 4,601,309 A | 7/1986 | Chang |
| 4,617,932 A | 10/1986 | Kornberg |
| 4,662,355 A | 5/1987 | Pieronne et al. |
| 4,665,906 A | 5/1987 | Jervis |
| 4,705,507 A | 11/1987 | Boyles |
| 4,836,204 A | 6/1989 | Landymore et al. |
| 4,979,955 A | 12/1990 | Smith |
| 4,988,339 A | 1/1991 | Vadher |
| 4,995,857 A | 2/1991 | Arnold |
| 5,035,706 A | 7/1991 | Giantureo et al. |
| 5,037,427 A | 8/1991 | Harada et al. |
| 5,089,005 A | 2/1992 | Harada |
| 5,186,431 A | 2/1993 | Tamari |
| 5,197,978 A | 3/1993 | Hess |
| 5,267,940 A | 12/1993 | Moulder |
| 5,290,227 A | 3/1994 | Pasque |
| 5,312,341 A | 5/1994 | Turi |
| 5,326,374 A | 7/1994 | Ilbawi et al. |
| 5,332,402 A | 7/1994 | Teitelbaum |
| 5,334,217 A | 8/1994 | Das |
| 5,378,239 A | 1/1995 | Termin et al. |
| 5,409,019 A | 4/1995 | Wilk |
| 5,429,144 A | 7/1995 | Wilk |
| 5,500,015 A | 3/1996 | Deac |
| 5,531,759 A | 7/1996 | Kensey et al. |
| 5,545,210 A | 8/1996 | Hess et al. |
| 5,556,386 A | 9/1996 | Todd |
| 5,578,008 A | 11/1996 | Hara |
| 5,584,803 A | 12/1996 | Stevens et al. |
| 5,597,377 A | 1/1997 | Aldea |
| 5,645,559 A | 7/1997 | Hachtman et al. |
| 5,655,548 A | 8/1997 | Nelson et al. |
| 5,662,711 A | 9/1997 | Douglas |
| 5,702,412 A | 12/1997 | Popov et al. |
| 5,725,552 A | 3/1998 | Kotula et al. |
| 5,741,324 A | 4/1998 | Glastra |
| 5,749,880 A | 5/1998 | Banas et al. |
| 5,779,716 A | 7/1998 | Cano et al. |
| 5,795,307 A | 8/1998 | Krueger |
| 5,810,836 A | 9/1998 | Hussein et al. |
| 5,824,062 A | 10/1998 | Patke et al. |
| 5,824,071 A | 10/1998 | Nelson et al. |
| 5,846,261 A | 12/1998 | Kotula et al. |
| 5,910,144 A | 6/1999 | Hayashi |
| 5,916,193 A | 6/1999 | Stevens et al. |
| 5,941,850 A | 8/1999 | Shah et al. |
| 5,957,949 A | 9/1999 | Leonhardt et al. |
| 5,990,379 A | 11/1999 | Gregory |
| 6,027,518 A | 2/2000 | Gaber |
| 6,039,755 A | 3/2000 | Edwin et al. |
| 6,039,759 A | 3/2000 | Carpentier et al. |
| 6,086,610 A | 7/2000 | Duerig et al. |
| 6,111,520 A | 8/2000 | Allen et al. |
| 6,117,159 A | 9/2000 | Huebsch et al. |
| 6,120,534 A | 9/2000 | Ruiz |
| 6,124,523 A | 9/2000 | Banas et al. |
| 6,126,686 A | 10/2000 | Badylak et al. |
| 6,165,188 A | 12/2000 | Saadat et al. |
| 6,210,318 B1 | 4/2001 | Lederman |
| 6,214,039 B1 | 4/2001 | Banas et al. |
| 6,217,541 B1 | 4/2001 | Yu |
| 6,221,096 B1 | 4/2001 | Aiba et al. |
| 6,242,762 B1 | 6/2001 | Brown et al. |
| 6,245,099 B1 | 6/2001 | Edwin et al. |
| 6,254,564 B1 | 7/2001 | Wilk et al. |
| 6,260,552 B1 | 7/2001 | Mortier et al. |
| 6,264,684 B1 | 7/2001 | Banas et al. |
| 6,270,515 B1 | 8/2001 | Linden et al. |
| 6,270,526 B1 | 8/2001 | Cox |
| 6,277,078 B1 | 8/2001 | Porat et al. |
| 6,278,379 B1 | 8/2001 | Allen et al. |
| 6,302,892 B1 | 10/2001 | Wilk |
| 6,306,141 B1 | 10/2001 | Jervis |
| 6,328,699 B1 | 12/2001 | Eigler et al. |
| 6,344,022 B1 | 2/2002 | Jarvik |
| 6,358,277 B1 | 3/2002 | Duran |
| 6,391,036 B1 | 5/2002 | Berg et al. |
| 6,398,803 B1 | 6/2002 | Layne et al. |
| 6,406,422 B1 | 6/2002 | Landesberg |
| 6,447,539 B1 | 9/2002 | Nelson et al. |
| 6,451,051 B2 | 9/2002 | Drasler et al. |
| 6,458,153 B1 | 10/2002 | Bailey et al. |
| 6,468,303 B1 | 10/2002 | Amplatz et al. |
| 6,475,136 B1 | 11/2002 | Forsell |
| 6,478,776 B1 | 11/2002 | Rosenman et al. |
| 6,485,507 B1 | 11/2002 | Walak et al. |
| 6,488,702 B1 | 12/2002 | Besselink |
| 6,491,705 B2 | 12/2002 | Gifford et al. |
| 6,527,698 B1 | 3/2003 | Kung et al. |
| 6,544,208 B2 | 4/2003 | Ethier et al. |
| 6,547,814 B2 | 4/2003 | Edwin et al. |
| 6,562,066 B1 * | 5/2003 | Martin .................. A61F 2/2493 604/8 |
| 6,572,652 B2 | 6/2003 | Shaknovich |
| 6,579,314 B1 | 6/2003 | Lombardi et al. |
| 6,589,198 B1 | 7/2003 | Soltanpour et al. |
| 6,632,169 B2 | 10/2003 | Korakianitis et al. |
| 6,638,303 B1 | 10/2003 | Campbell |
| 6,641,610 B2 | 11/2003 | Wolf et al. |
| 6,652,578 B2 | 11/2003 | Bailey et al. |
| 6,685,664 B2 | 2/2004 | Levin et al. |
| 6,712,836 B1 | 3/2004 | Berg et al. |
| 6,740,115 B2 | 5/2004 | Lombardi et al. |
| 6,758,858 B2 | 7/2004 | McCrea et al. |
| 6,764,507 B2 | 7/2004 | Shanley et al. |
| 6,770,087 B2 | 8/2004 | Layne et al. |
| 6,797,217 B2 | 9/2004 | McCrea et al. |
| 6,890,350 B1 | 5/2005 | Walak |
| 6,970,742 B2 | 11/2005 | Mann et al. |
| 7,001,409 B2 | 2/2006 | Amplatz |
| 7,004,966 B2 | 2/2006 | Edwin et al. |
| 7,025,777 B2 | 4/2006 | Moore |
| 7,060,150 B2 | 6/2006 | Banas et al. |
| 7,083,640 B2 | 8/2006 | Lombardi et al. |
| 7,115,095 B2 | 10/2006 | Eigler et al. |
| 7,118,600 B2 | 10/2006 | Dua et al. |
| 7,137,953 B2 | 11/2006 | Eigler et al. |
| 7,147,604 B1 | 12/2006 | Allen et al. |
| 7,149,587 B2 | 12/2006 | Wardle et al. |
| 7,169,160 B1 | 1/2007 | Middleman et al. |
| 7,169,172 B2 | 1/2007 | Levine et al. |
| 7,195,594 B2 | 3/2007 | Eigler et al. |
| 7,208,010 B2 | 4/2007 | Shanley et al. |
| 7,226,558 B2 | 6/2007 | Nieman et al. |
| 7,245,117 B1 | 7/2007 | Joy et al. |
| 7,294,115 B1 | 11/2007 | Wilk |
| 7,306,756 B2 | 12/2007 | Edwin et al. |
| 7,402,899 B1 | 7/2008 | Whiting et al. |

(56) References Cited

U.S. PATENT DOCUMENTS

| | | |
|---|---|---|
| 7,439,723 B2 | 10/2008 | Allen et al. |
| 7,468,071 B2 | 12/2008 | Edwin et al. |
| 7,483,743 B2 | 1/2009 | Mann et al. |
| 7,498,799 B2 | 3/2009 | Allen et al. |
| 7,509,169 B2 | 3/2009 | Eigler et al. |
| 7,550,978 B2 | 6/2009 | Joy et al. |
| 7,578,899 B2 | 8/2009 | Edwin et al. |
| 7,590,449 B2 | 9/2009 | Mann et al. |
| 7,615,010 B1 | 11/2009 | Najafi et al. |
| 7,621,879 B2 | 11/2009 | Eigler et al. |
| 7,679,355 B2 | 3/2010 | Allen et al. |
| 7,717,854 B2 | 5/2010 | Mann et al. |
| 7,794,473 B2 | 9/2010 | Tessmer et al. |
| 7,839,153 B2 | 11/2010 | Joy et al. |
| 7,842,083 B2 | 11/2010 | Shanley et al. |
| 7,854,172 B2 | 12/2010 | O'Brien et al. |
| 7,862,513 B2 | 1/2011 | Eigler et al. |
| 7,914,639 B2 | 3/2011 | Layne et al. |
| 7,939,000 B2 | 5/2011 | Edwin et al. |
| 7,988,724 B2 | 8/2011 | Salahieh et al. |
| 7,993,383 B2 | 8/2011 | Hartley et al. |
| 8,012,194 B2 | 9/2011 | Edwin et al. |
| 8,016,877 B2 | 9/2011 | Seguin et al. |
| 8,021,420 B2 | 9/2011 | Dolan |
| 8,025,625 B2 | 9/2011 | Allen |
| 8,025,668 B2 | 9/2011 | McCartney |
| 8,043,360 B2 | 10/2011 | McNamara et al. |
| 8,070,708 B2 | 12/2011 | Rottenberg et al. |
| 8,091,556 B2 | 1/2012 | Keren et al. |
| 8,096,959 B2 | 1/2012 | Stewart et al. |
| 8,137,605 B2 | 3/2012 | McCrea et al. |
| 8,142,363 B1 | 3/2012 | Eigler et al. |
| 8,147,545 B2 | 4/2012 | Avior |
| 8,157,852 B2 | 4/2012 | Bloom et al. |
| 8,157,860 B2 | 4/2012 | McNamara et al. |
| 8,157,940 B2 | 4/2012 | Edwin et al. |
| 8,158,041 B2 | 4/2012 | Colone |
| 8,187,321 B2 | 5/2012 | Shanley et al. |
| 8,202,313 B2 | 6/2012 | Shanley et al. |
| 8,206,435 B2 | 6/2012 | Shanley et al. |
| 8,235,916 B2 | 8/2012 | Whiting et al. |
| 8,235,933 B2 | 8/2012 | Keren et al. |
| 8,246,677 B2 | 8/2012 | Ryan |
| 8,287,589 B2 | 10/2012 | Otto et al. |
| 8,298,150 B2 | 10/2012 | Mann et al. |
| 8,298,244 B2 | 10/2012 | Garcia et al. |
| 8,303,511 B2 | 11/2012 | Eigler et al. |
| 8,313,524 B2 | 11/2012 | Edwin et al. |
| 8,328,751 B2 | 12/2012 | Keren et al. |
| 8,337,650 B2 | 12/2012 | Edwin et al. |
| 8,348,996 B2 | 1/2013 | Tuval et al. |
| 8,357,193 B2 | 1/2013 | Phan et al. |
| 8,398,708 B2 | 3/2013 | Meiri et al. |
| 8,460,366 B2 | 6/2013 | Rowe |
| 8,468,667 B2 | 6/2013 | Straubinger et al. |
| 8,480,594 B2 | 7/2013 | Eigler et al. |
| 8,579,966 B2 | 11/2013 | Seguin et al. |
| 8,597,225 B2 | 12/2013 | Kapadia |
| 8,617,337 B2 | 12/2013 | Layne et al. |
| 8,617,441 B2 | 12/2013 | Edwin et al. |
| 8,652,284 B2 | 2/2014 | Bogert et al. |
| 8,665,086 B2 | 3/2014 | Miller et al. |
| 8,696,611 B2 | 4/2014 | Nitzan et al. |
| 8,790,241 B2 | 7/2014 | Edwin et al. |
| 8,882,697 B2 | 11/2014 | Celermajer et al. |
| 8,882,798 B2 | 11/2014 | Schwab et al. |
| 8,911,489 B2 | 12/2014 | Ben-Muvhar |
| 9,005,155 B2 * | 4/2015 | Sugimoto ............ A61M 27/002 604/8 |
| 9,034,034 B2 | 5/2015 | Nitzan et al. |
| 9,055,917 B2 | 6/2015 | Mann et al. |
| 9,060,696 B2 | 6/2015 | Eigler et al. |
| 9,067,050 B2 | 6/2015 | Gallagher et al. |
| 9,205,236 B2 | 12/2015 | McNamara et al. |
| 9,220,429 B2 | 12/2015 | Nabutovsky et al. |
| 9,358,371 B2 | 6/2016 | McNamara et al. |
| 9,393,115 B2 | 7/2016 | Tabor et al. |
| 9,456,812 B2 | 10/2016 | Finch et al. |
| 9,622,895 B2 | 4/2017 | Cohen et al. |
| 9,629,715 B2 | 4/2017 | Nitzan et al. |
| 9,681,948 B2 | 6/2017 | Levi et al. |
| 9,707,382 B2 | 7/2017 | Nitzan et al. |
| 9,713,696 B2 | 7/2017 | Yacoby et al. |
| 9,757,107 B2 | 9/2017 | McNamara et al. |
| 9,789,294 B2 | 10/2017 | Taft et al. |
| 9,918,677 B2 | 3/2018 | Eigler et al. |
| 9,943,670 B2 | 4/2018 | Keren et al. |
| 9,980,815 B2 | 5/2018 | Nitzan et al. |
| 10,045,766 B2 | 8/2018 | McNamara et al. |
| 10,047,421 B2 | 8/2018 | Khan et al. |
| 10,076,403 B1 | 9/2018 | Eigler et al. |
| 10,105,103 B2 | 10/2018 | Goldshtein et al. |
| 10,111,741 B2 | 10/2018 | Michalak |
| 10,207,087 B2 | 2/2019 | Keren et al. |
| 10,207,807 B2 | 2/2019 | Moran et al. |
| 10,251,740 B2 | 4/2019 | Eigler et al. |
| 10,251,750 B2 | 4/2019 | Eigler et al. |
| 10,299,687 B2 | 5/2019 | Nabutovsky et al. |
| 10,357,320 B2 | 7/2019 | Beira |
| 10,357,357 B2 | 7/2019 | Levi et al. |
| 10,368,981 B2 | 8/2019 | Nitzan et al. |
| 10,463,490 B2 | 11/2019 | Rottenberg et al. |
| 10,478,594 B2 | 11/2019 | Yacoby et al. |
| 10,548,725 B2 | 2/2020 | Alkhatib et al. |
| 10,561,423 B2 | 2/2020 | Sharma |
| 10,639,459 B2 | 5/2020 | Nitzan et al. |
| 10,828,151 B2 | 11/2020 | Nitzan et al. |
| 10,835,394 B2 | 11/2020 | Nae et al. |
| 10,898,698 B1 | 1/2021 | Eigler et al. |
| 10,912,645 B2 | 2/2021 | Rottenberg et al. |
| 10,925,706 B2 | 2/2021 | Eigler et al. |
| 10,940,296 B2 | 3/2021 | Keren |
| 2002/0120277 A1 | 8/2002 | Hauschild et al. |
| 2002/0165479 A1 | 11/2002 | Wilk |
| 2002/0165606 A1 | 11/2002 | Wolf et al. |
| 2002/0169371 A1 | 11/2002 | Gilderdale |
| 2002/0169377 A1 | 11/2002 | Khairkhahan et al. |
| 2002/0173742 A1 | 11/2002 | Keren et al. |
| 2002/0183628 A1 | 12/2002 | Reich et al. |
| 2003/0028213 A1 | 2/2003 | Thill et al. |
| 2003/0100920 A1 | 5/2003 | Akin et al. |
| 2003/0125798 A1 | 7/2003 | Martin |
| 2003/0136417 A1 | 7/2003 | Fonseca et al. |
| 2003/0139819 A1 | 7/2003 | Beer et al. |
| 2003/0176914 A1 | 9/2003 | Rabkin et al. |
| 2003/0209835 A1 | 11/2003 | Chun et al. |
| 2003/0216679 A1 | 11/2003 | Wolf et al. |
| 2003/0216803 A1 | 11/2003 | Ledergerber |
| 2004/0010219 A1 | 1/2004 | McCusker et al. |
| 2004/0016514 A1 | 1/2004 | Nien |
| 2004/0073242 A1 | 4/2004 | Chanduszko |
| 2004/0077988 A1 | 4/2004 | Tweden et al. |
| 2004/0088045 A1 | 5/2004 | Cox |
| 2004/0093075 A1 | 5/2004 | Kuehne |
| 2004/0102797 A1 | 5/2004 | Golden et al. |
| 2004/0116999 A1 | 6/2004 | Ledergerber |
| 2004/0138743 A1 | 7/2004 | Myers et al. |
| 2004/0147869 A1 | 7/2004 | Wolf et al. |
| 2004/0147871 A1 | 7/2004 | Burnett |
| 2004/0147886 A1 | 7/2004 | Bonni |
| 2004/0147969 A1 | 7/2004 | Mann et al. |
| 2004/0162514 A1 | 8/2004 | Alferness et al. |
| 2004/0193261 A1 | 9/2004 | Berreklouw |
| 2004/0210190 A1 | 10/2004 | Kohler et al. |
| 2004/0210307 A1 | 10/2004 | Khairkhahan |
| 2004/0225352 A1 | 11/2004 | Osborne et al. |
| 2005/0003327 A1 | 1/2005 | Elian et al. |
| 2005/0033327 A1 | 2/2005 | Gainor et al. |
| 2005/0033351 A1 | 2/2005 | Newton |
| 2005/0065589 A1 | 3/2005 | Schneider et al. |
| 2005/0125032 A1 | 6/2005 | Whisenant et al. |
| 2005/0137682 A1 | 6/2005 | Justino |
| 2005/0148925 A1 | 7/2005 | Rottenberg et al. |
| 2005/0165344 A1 | 7/2005 | Dobak |

(56) References Cited

U.S. PATENT DOCUMENTS

| | | |
|---|---|---|
| 2005/0182486 A1 | 8/2005 | Gabbay |
| 2005/0283231 A1 | 12/2005 | Haug et al. |
| 2005/0288596 A1 | 12/2005 | Eigler et al. |
| 2005/0288706 A1 | 12/2005 | Widomski et al. |
| 2006/0009800 A1 | 1/2006 | Christianson et al. |
| 2006/0025857 A1 | 2/2006 | Bergheim et al. |
| 2006/0111660 A1 | 5/2006 | Wolf et al. |
| 2006/0116710 A1 | 6/2006 | Corcoran et al. |
| 2006/0122647 A1 | 6/2006 | Callaghan et al. |
| 2006/0167541 A1 | 7/2006 | Lattouf |
| 2006/0184231 A1 | 8/2006 | Rucker |
| 2006/0212110 A1 | 9/2006 | Osborne et al. |
| 2006/0241745 A1 | 10/2006 | Solem |
| 2006/0256611 A1 | 11/2006 | Bednorz et al. |
| 2006/0282157 A1 | 12/2006 | Hill et al. |
| 2007/0010852 A1 | 1/2007 | Blaeser et al. |
| 2007/0021739 A1 | 1/2007 | Weber |
| 2007/0043435 A1 | 2/2007 | Seguin et al. |
| 2007/0129756 A1 | 6/2007 | Abbott et al. |
| 2007/0191863 A1 | 8/2007 | De Juan, Jr. |
| 2007/0213813 A1 | 9/2007 | Von Segesser et al. |
| 2007/0276413 A1 | 11/2007 | Nobles |
| 2007/0276414 A1 | 11/2007 | Nobles |
| 2007/0282157 A1 | 12/2007 | Rottenberg et al. |
| 2007/0299384 A1 | 12/2007 | Faul et al. |
| 2008/0034836 A1 | 2/2008 | Eigler et al. |
| 2008/0086205 A1 | 4/2008 | Gordy et al. |
| 2008/0125861 A1 | 5/2008 | Webler et al. |
| 2008/0177300 A1 | 7/2008 | Mas et al. |
| 2008/0262602 A1 | 10/2008 | Wilk et al. |
| 2008/0319525 A1 | 12/2008 | Tieu et al. |
| 2009/0030499 A1 | 1/2009 | Bebb et al. |
| 2009/0054976 A1 | 2/2009 | Tuval et al. |
| 2009/0125104 A1 | 5/2009 | Hoffman |
| 2009/0149947 A1 | 6/2009 | Frohwitter |
| 2009/0198315 A1 | 8/2009 | Boudjemline |
| 2009/0276040 A1 | 11/2009 | Rowe et al. |
| 2009/0319037 A1 | 12/2009 | Rowe et al. |
| 2010/0004740 A1 | 1/2010 | Seguin et al. |
| 2010/0022940 A1 | 1/2010 | Thompson |
| 2010/0057192 A1 | 3/2010 | Celermajer |
| 2010/0069836 A1 | 3/2010 | Satake |
| 2010/0070022 A1 | 3/2010 | Kuehling |
| 2010/0081867 A1 | 4/2010 | Fishler et al. |
| 2010/0100167 A1 | 4/2010 | Bortlein et al. |
| 2010/0121434 A1 | 5/2010 | Paul et al. |
| 2010/0179590 A1 | 7/2010 | Fortson et al. |
| 2010/0191326 A1 | 7/2010 | Alkhatib |
| 2010/0249909 A1 | 9/2010 | McNamara et al. |
| 2010/0249910 A1 | 9/2010 | McNamara et al. |
| 2010/0249915 A1 | 9/2010 | Zhang |
| 2010/0256548 A1 | 10/2010 | McNamara et al. |
| 2010/0256753 A1 | 10/2010 | McNamara et al. |
| 2010/0298755 A1 | 11/2010 | McNamara et al. |
| 2011/0022057 A1 | 1/2011 | Eigler et al. |
| 2011/0022157 A1 | 1/2011 | Essinger et al. |
| 2011/0054515 A1 | 3/2011 | Bridgeman et al. |
| 2011/0071623 A1 | 3/2011 | Finch et al. |
| 2011/0071624 A1 | 3/2011 | Finch et al. |
| 2011/0093059 A1 | 4/2011 | Fischell et al. |
| 2011/0152923 A1 | 6/2011 | Fox |
| 2011/0190874 A1 | 8/2011 | Celermajer et al. |
| 2011/0218479 A1 | 9/2011 | Rottenberg et al. |
| 2011/0218480 A1 | 9/2011 | Rottenberg et al. |
| 2011/0218481 A1 | 9/2011 | Rottenberg et al. |
| 2011/0257723 A1 | 10/2011 | McNamara |
| 2011/0264203 A1 | 10/2011 | Dwork et al. |
| 2011/0276086 A1 | 11/2011 | Al-Qbandi et al. |
| 2011/0295182 A1 | 12/2011 | Finch et al. |
| 2011/0295183 A1 | 12/2011 | Finch et al. |
| 2011/0295362 A1 | 12/2011 | Finch et al. |
| 2011/0295366 A1 | 12/2011 | Finch et al. |
| 2011/0306916 A1 | 12/2011 | Nitzan et al. |
| 2011/0319806 A1 | 12/2011 | Wardle |
| 2012/0022633 A1 | 1/2012 | Olson et al. |
| 2012/0035590 A1 | 2/2012 | Whiting et al. |
| 2012/0041422 A1 | 2/2012 | Whiting et al. |
| 2012/0046528 A1 | 2/2012 | Eigler et al. |
| 2012/0046739 A1 | 2/2012 | Von Oepen et al. |
| 2012/0053686 A1 | 3/2012 | McNamara et al. |
| 2012/0071918 A1 | 3/2012 | Amin et al. |
| 2012/0130301 A1 | 5/2012 | McNamara et al. |
| 2012/0165928 A1* | 6/2012 | Nitzan .................. A61F 2/2418 623/2.15 |
| 2012/0179172 A1 | 7/2012 | Paul et al. |
| 2012/0190991 A1 | 7/2012 | Bornzin et al. |
| 2012/0265296 A1 | 10/2012 | McNamara et al. |
| 2012/0271398 A1 | 10/2012 | Essinger et al. |
| 2012/0289882 A1 | 11/2012 | McNamara et al. |
| 2012/0290062 A1 | 11/2012 | McNamara et al. |
| 2013/0030521 A1 | 1/2013 | Nitzan et al. |
| 2013/0046373 A1 | 2/2013 | Cartledge et al. |
| 2013/0138145 A1 | 5/2013 | Von Oepen |
| 2013/0178783 A1 | 7/2013 | McNamara et al. |
| 2013/0178784 A1 | 7/2013 | McNamara et al. |
| 2013/0184633 A1 | 7/2013 | McNamara et al. |
| 2013/0184634 A1 | 7/2013 | McNamara et al. |
| 2013/0197423 A1 | 8/2013 | Keren et al. |
| 2013/0197547 A1 | 8/2013 | Fukuoka et al. |
| 2013/0197629 A1 | 8/2013 | Gainor et al. |
| 2013/0204175 A1 | 8/2013 | Sugimoto |
| 2013/0231737 A1 | 9/2013 | McNamara et al. |
| 2013/0261531 A1 | 10/2013 | Gallagher et al. |
| 2013/0281988 A1 | 10/2013 | Magnin et al. |
| 2013/0304192 A1 | 11/2013 | Chanduszko |
| 2014/0012181 A1 | 1/2014 | Sugimoto et al. |
| 2014/0012303 A1 | 1/2014 | Heipl |
| 2014/0012368 A1 | 1/2014 | Sugimoto et al. |
| 2014/0012369 A1 | 1/2014 | Murry, III et al. |
| 2014/0067037 A1 | 3/2014 | Fargahi |
| 2014/0094904 A1 | 4/2014 | Salahieh et al. |
| 2014/0128795 A1 | 5/2014 | Keren et al. |
| 2014/0128796 A1 | 5/2014 | Keren et al. |
| 2014/0163449 A1 | 6/2014 | Rottenberg et al. |
| 2014/0194971 A1 | 7/2014 | McNamara |
| 2014/0213959 A1 | 7/2014 | Nitzan et al. |
| 2014/0222144 A1 | 8/2014 | Eberhardt et al. |
| 2014/0249621 A1 | 9/2014 | Eidenschink |
| 2014/0257167 A1 | 9/2014 | Celermajer |
| 2014/0275916 A1 | 9/2014 | Nabutovsky et al. |
| 2014/0277045 A1 | 9/2014 | Fazio et al. |
| 2014/0277054 A1 | 9/2014 | McNamara et al. |
| 2014/0303710 A1 | 10/2014 | Zhang et al. |
| 2014/0350565 A1 | 11/2014 | Yacoby et al. |
| 2014/0350658 A1 | 11/2014 | Benary et al. |
| 2014/0350661 A1 | 11/2014 | Schaeffer |
| 2014/0350669 A1 | 11/2014 | Gillespie et al. |
| 2014/0357946 A1 | 12/2014 | Golden et al. |
| 2015/0034217 A1 | 2/2015 | Vad |
| 2015/0039084 A1 | 2/2015 | Levi et al. |
| 2015/0066140 A1 | 3/2015 | Quadri et al. |
| 2015/0073539 A1 | 3/2015 | Geiger et al. |
| 2015/0119796 A1 | 4/2015 | Finch |
| 2015/0127093 A1 | 5/2015 | Hosmer et al. |
| 2015/0142049 A1 | 5/2015 | Delgado et al. |
| 2015/0148731 A1 | 5/2015 | McNamara et al. |
| 2015/0148896 A1 | 5/2015 | Karapetian et al. |
| 2015/0157455 A1 | 6/2015 | Hoang et al. |
| 2015/0173897 A1 | 6/2015 | Raanani et al. |
| 2015/0182334 A1 | 7/2015 | Bourang et al. |
| 2015/0190229 A1 | 7/2015 | Seguin |
| 2015/0196383 A1 | 7/2015 | Johnson |
| 2015/0201998 A1 | 7/2015 | Roy et al. |
| 2015/0209143 A1 | 7/2015 | Duffy et al. |
| 2015/0230924 A1 | 8/2015 | Miller et al. |
| 2015/0238314 A1 | 8/2015 | Bortlein et al. |
| 2015/0245908 A1 | 9/2015 | Nitzan et al. |
| 2015/0272731 A1 | 10/2015 | Racchini et al. |
| 2015/0282790 A1 | 10/2015 | Quinn et al. |
| 2015/0282931 A1 | 10/2015 | Brunnett et al. |
| 2015/0359556 A1 | 12/2015 | Vardi |
| 2016/0007924 A1 | 1/2016 | Eigler et al. |
| 2016/0022423 A1 | 1/2016 | McNamara et al. |
| 2016/0022970 A1 | 1/2016 | Forcucci et al. |

(56) References Cited

U.S. PATENT DOCUMENTS

| | | |
|---|---|---|
| 2016/0073907 A1 | 3/2016 | Nabutovsky et al. |
| 2016/0120550 A1 | 5/2016 | McNamara et al. |
| 2016/0129260 A1 | 5/2016 | Mann et al. |
| 2016/0157862 A1 | 6/2016 | Hernandez et al. |
| 2016/0166381 A1 | 6/2016 | Sugimoto et al. |
| 2016/0184561 A9 | 6/2016 | McNamara et al. |
| 2016/0206423 A1 | 7/2016 | O'Connor et al. |
| 2016/0213467 A1 | 7/2016 | Backus et al. |
| 2016/0220360 A1 | 8/2016 | Lin et al. |
| 2016/0220365 A1 | 8/2016 | Backus et al. |
| 2016/0262878 A1 | 9/2016 | Backus et al. |
| 2016/0262879 A1 | 9/2016 | Meiri et al. |
| 2016/0287386 A1 | 10/2016 | Alon et al. |
| 2016/0296325 A1 | 10/2016 | Edelman et al. |
| 2016/0361167 A1 | 12/2016 | Tuval et al. |
| 2016/0361184 A1 | 12/2016 | Tabor et al. |
| 2017/0035435 A1 | 2/2017 | Amin et al. |
| 2017/0113026 A1 | 4/2017 | Finch |
| 2017/0128705 A1 | 5/2017 | Forcucci et al. |
| 2017/0135685 A9 | 5/2017 | McNamara et al. |
| 2017/0165532 A1 | 6/2017 | Khan et al. |
| 2017/0216025 A1 | 8/2017 | Nitzan et al. |
| 2017/0224323 A1 | 8/2017 | Rowe et al. |
| 2017/0224444 A1 | 8/2017 | Viecilli et al. |
| 2017/0231766 A1 | 8/2017 | Hariton et al. |
| 2017/0273790 A1 | 9/2017 | Vettukattil et al. |
| 2017/0281339 A1 | 10/2017 | Levi et al. |
| 2017/0312486 A1 | 11/2017 | Nitzan et al. |
| 2017/0319823 A1 | 11/2017 | Yacoby et al. |
| 2017/0325956 A1 | 11/2017 | Rottenberg et al. |
| 2017/0348100 A1 | 12/2017 | Lane et al. |
| 2018/0099128 A9 | 4/2018 | McNamara et al. |
| 2018/0104053 A1 | 4/2018 | Alkhatib et al. |
| 2018/0125630 A1 | 5/2018 | Hynes et al. |
| 2018/0243071 A1 | 8/2018 | Eigler et al. |
| 2018/0256865 A1 | 9/2018 | Finch et al. |
| 2018/0263766 A1 | 9/2018 | Nitzan et al. |
| 2018/0280667 A1 | 10/2018 | Keren |
| 2018/0344994 A1 | 12/2018 | Karavany et al. |
| 2019/0000327 A1 | 1/2019 | Doan et al. |
| 2019/0008628 A1 | 1/2019 | Eigler et al. |
| 2019/0015188 A1 | 1/2019 | Eigler et al. |
| 2019/0021861 A1 | 1/2019 | Finch |
| 2019/0239754 A1 | 8/2019 | Nabutovsky et al. |
| 2019/0328513 A1 | 10/2019 | Levi et al. |
| 2019/0336163 A1 | 11/2019 | McNamara et al. |
| 2020/0060825 A1 | 2/2020 | Rottenberg et al. |
| 2020/0078558 A1 | 3/2020 | Yacoby et al. |
| 2020/0085600 A1 | 3/2020 | Schwartz et al. |
| 2020/0197178 A1 | 6/2020 | Vecchio |
| 2020/0261705 A1 | 8/2020 | Nitzan et al. |
| 2020/0315599 A1 | 10/2020 | Nae et al. |
| 2020/0368505 A1 | 11/2020 | Nae et al. |
| 2021/0052378 A1 | 2/2021 | Nitzan et al. |

FOREIGN PATENT DOCUMENTS

| | | |
|---|---|---|
| EP | 2238933 A1 | 10/2010 |
| EP | 2305321 A1 | 4/2011 |
| EP | 1965842 B1 | 11/2011 |
| EP | 3400907 A1 | 11/2018 |
| FR | 2827153 A1 | 1/2003 |
| WO | WO-9531945 A1 | 11/1995 |
| WO | WO-9727898 A1 | 8/1997 |
| WO | WO-99/60941 A1 | 12/1999 |
| WO | WO-00/44311 A2 | 8/2000 |
| WO | WO-0050100 A1 | 8/2000 |
| WO | WO-0110314 A2 | 2/2001 |
| WO | WO-0226281 A1 | 4/2002 |
| WO | WO-02/071974 A2 | 9/2002 |
| WO | WO-02087473 A1 | 11/2002 |
| WO | WO-03/053495 A2 | 7/2003 |
| WO | WO-2005/027752 A1 | 3/2005 |
| WO | WO-2005/074367 A1 | 8/2005 |
| WO | WO-2006/127765 A1 | 11/2006 |
| WO | WO-2007/083288 A2 | 7/2007 |
| WO | WO-2008/055301 A1 | 5/2008 |
| WO | WO-2009/029261 A1 | 3/2009 |
| WO | WO-2010/128501 A1 | 11/2010 |
| WO | WO-2010129089 A2 | 11/2010 |
| WO | WO-2011062858 A1 | 5/2011 |
| WO | WO-2013/096965 A1 | 6/2013 |
| WO | WO-2016/178171 A1 | 11/2016 |
| WO | WO-2017118920 A1 | 7/2017 |
| WO | WO-2018158747 A1 | 9/2018 |
| WO | WO-2019015617 A1 | 1/2019 |
| WO | WO-2019085841 A1 | 5/2019 |
| WO | WO-2019109013 A1 | 6/2019 |
| WO | WO-2019142152 A1 | 7/2019 |
| WO | WO-2019179447 A1 | 9/2019 |
| WO | WO-2019218072 A1 | 11/2019 |

OTHER PUBLICATIONS

Abraham et al., "Sustained efficacy of pulmonary artery pressure to guide adjustment of chronic heart failure therapy: complete follow-up results from the CHAMPION randomised trial," The Lancet, doi.org/10.1016/S0140-6736(15)00723-0 (2015).

Abraham et al., "Wireless pulmonary artery haemodynamic monitoring in chronic heart failure: a randomised controlled trial," The Lancet, DOI:10.1016/S0140-6736(11)60101-3 (2011).

Abreu et al., "Doppler ultrasonography of the femoropopliteal segment in patients with venous ulcer," J Vasc Bras., 11(4):277-285 (2012).

Adamson et al., "Ongoing Right Ventricular Hemodynamics in Heart Failure Clinical Value of Measurements Derived From an Implantable Monitoring System," J Am Coll Cardiol., 41(4):565-571 (2003).

Adamson et al., "Wireless Pulmonary Artery Pressure Monitoring Guides Management to Reduce Decompensation in Heart Failure With Preserved Ejection Fraction," Circ Heart Fail., 7:935-944 (2014).

Ambrosy et al. "The Global Health and Economic Burden of Hospitalizations for Heart Failure," J Am Coll Cardiol., 63:1123-1133 (2014).

Aminde et al., "Current diagnostic and treatment strategies for Lutembacher syndrome: the pivotal role of echocardiography," Cardiovasc Diagn Ther., 5(2):122-132 (2015).

Anderas E. "Advanced MEMS Pressure Sensors Operating in Fluids," Digital Comprehensive Summaries of Uppsala Dissertation from the Faculty of Science and Technology 933. Uppsala ISBN 978-91-554-8369-2 (2012).

Anderas et al., "Tilted c-axis Thin-Film Bulk Wave Resonant Pressure Sensors with Improved Sensitivity," IEEE Sensors J., 12(8):2653-2654 (2012).

Ataya et al., "A Review of Targeted Pulmonary Arterial Hypertension-Specific Pharmacotherapy," J. Clin. Med., 5(12):114 (2016).

Bannan et al., "Characteristics of Adult Patients with Atrial Septal Defects Presenting with Paradoxical Embolism.," Catheterization and Cardiovascular Interventions, 74:1066-1069 (2009).

Baumgartner et al., "ESC Guidelines for the management of grown-up congenital heart disease (new version 2010)—The Task Force on the Management of Grown-up Congenital Heart Disease of the European Society of Cardiology (ESC)," Eur Heart J., 31:2915-2957 (2010).

Beemath et al., "Pulmonary Embolism as a Cause of Death in Adults Who Died With Heart Failure," Am J Cardiol., 98:1073-1075 (2006).

Benza et al., "Monitoring Pulmonary Arterial Hypertension Using an Implantable Hemodynamic Sensor," CHEST, 156(6):1176-1186 (2019).

Boehm, et al., "Balloon Atrial Septostomy: History and Technique," Images Paeditr. Cardiol., 8(1):8-14(2006).

Bruch et al., "Fenestrated Occluders for Treatment of ASD in Elderly Patients with Pulmonary Hypertension and/or Right Heart Failure," J Interven Cardiol., 21(1):44-49 (2008).

(56) References Cited

OTHER PUBLICATIONS

Burkhoff et al., "Assessment of systolic and diastolic ventricular properties via pressure-volume analysis: a guide for clinical, translational, and basic researchers," Am J Physiol Heart Circ Physiol., 289:H501-H512 (2005).
Butler et al. "Recognizing Worsening Chronic Heart Failure as an Entity and an End Point in Clinical Trials," JAMA., 312(8):789-790 (2014).
Chakko et al., "Clinical, radiographic, and hemodynamic correlations in chronic congestive heart failure: conflicting results may lead to inappropriate care," Am J Medicine, 90:353-359 (1991) (Abstract Only).
Chang et al., "State-of-the-art and recent developments in micro/ nanoscale pressure sensors for smart wearable devices and health monitoring systems," Nanotechnology and Precision Engineering, 3:43-52 (2020).
Chen et al., "Continuous wireless pressure monitoring and mapping with ultra-small passive sensors for health monitoring and critical care," Nature Communications, 5(1):1-10 (2014).
Chen et al., "National and Regional Trends in Heart Failure Hospitalization and Mortality Rates for Medicare Beneficiaries, 1998-2008," JAMA, 306(15):1669-1678 (2011).
Chiche et al., "Prevalence of patent foramen ovale and stroke in pulmonary embolism patients," Eur Heart J., 34:P1142 (2013) (Abstract Only).
Chin et al., "The right ventricle in pulmonary hypertension," Coron Artery Dis., 16(1):13-18 (2005) (Abstract Only).
Chun et al., "Lifetime Analysis of Hospitalizations and Survival of Patients Newly Admitted With Heart Failure," Circ Heart Fail., 5:414-421 (2012).
Ciarka et al., "Atrial Septostomy Decreases Sympathetic Overactivity in Pulmonary Arterial Hypertension," Chest, 131(6):P1831-1837 (2007) (Abstract Only).
Cleland et al., "The EuroHeart Failure survey programme—a survey on the quality of care among patients with heart failure in Europe—Part 1: patient characteristics and diagnosis," Eur Heart J., 24:442-463 (2003).
Clowes et al., "Mechanisms of Arterial Graft Healing—Rapid Transmural Capillary Ingrowth Provides a Source of Intimal Endothelium and Smooth Muscle in Porous PTFE Prostheses," Am J Pathol., 123:220-230 (1986).
Davies et al., "Abnormal left heart function after operation for atrial septal defect," British Heart Journal, 32:747-753 (1970).
Del Trigo et al., "Unidirectional Left-To-Right Interatrial Shunting for Treatment of Patients with Heart Failure with Reduced Ejection Fraction: a Safety and Proof-of-Principle Cohort Study," Lancet, 387:1290-1297 (2016).
Della Lucia et al., "Design, fabrication and characterization of SAW pressure sensors for offshore oil and gas exploration," Sensors and Actuators A: Physical, 222:322-328 (2015).
Drazner et al., "Prognostic Importance of Elevated Jugular Venous Pressure and a Third Heart Sound in Patients with Heart Failure," N Engl J Med., 345(8):574-81 (2001).
Drazner et al., "Relationship between Right and Left-Sided Filling Pressures in 1000 Patients with Advanced Heart Failure," Heart Lung Transplant, 18:1126-1132 (1999).
Drexel, et al., "The Effects of Cold Work and Heat Treatment on the Properties of Nitinol Wire, Proceedings of the International Conference on Shape Memory and Superelastic Technologies, SMST 2006," Pacific Grove, California, USA (pp. 447-454) May 7-11, 2006.
Eigler et al., "Cardiac Unloading with an Implantable Interatrial Shunt in Heart Failure: Serial Observations in an Ovine Model of Ischemic Cardiomyopathy," Structural Heart, 1:40-48 (2017).
Eigler, et al., Implantation and Recovery of Temporary Metallic Stents in Canine Coronary Arteries, JACC, 22(4):1207-1213 (1993).
Eshaghian et al., "Relation of Loop Diuretic Dose to Mortality in Advanced Heart Failure," Am J Cardiol., 97:1759-1764 (2006).
Extended European Search Report dated Mar. 29, 2019 in EP Patent Appl. Serial No. EP16789391 (1830).
Feldman et al., "Transcatheter Interatrial Shunt Device for the Treatment of Heart Failure with Preserved Ejection Fraction (Reduce LAP-HF I [Reduce Elevated Left Atrial Pressure in Patients With Heart Failure]), A Phase 2, Randomized, Sham-Controlled Trial," Circulation, 137:364-375 (2018).
Ferrari et al., "Impact of pulmonary arterial hypertension (PAH) on the lives of patients and carers: results from an international survey," Eur Respir J., 42:26312 (2013) (Abstract Only).
Fonarow et al., "Characteristics, Treatments, and Outcomes of Patients With Preserved Systolic Function Hospitalized for Heart Failure," J Am Coll Cardiol., 50(8):768-777 (2007).
Fonarow et al., "Risk Stratification for In-Hospital Mortality in Acutely Decompensated Heart Failure: Classification and Regression Tree Analysis," JAMA, 293(5):572-580 (2005).
Fonarow, G., "The Treatment Targets in Acute Decompensated Heart Failure," Rev Cardiovasc Med., 2:(2):S7-S12 (2001).
Galie et al., "2015 ESC/ERS Guidelines for the diagnosis and treatment of pulmonary hypertension—The Joint Task Force for the Diagnosis and Treatment of Pulmonary Hypertension of the European Society of Cardiology (ESC) and the European Respiratory Society (ERS)," European Heart Journal, 37:67-119 (2016).
Galie et al., "Pulmonary arterial hypertension: from the kingdom of the near-dead to multiple clinical trial meta-analyses," Eur Heart J., 31:2080-2086 (2010).
Galipeau et al., "Surface acoustic wave microsensors and applications," Smart Materials and Structures, 6(6):658-667 (1997) (Abstract Only).
Geva et al., "Atrial septal defects," Lancet, 383:1921-32 (2014).
Gheorghiade et al., "Acute Heart Failure Syndromes, Current State and Framework for Future Research," Circulation, 112:3958-3968 (2005).
Gheorghiade et al., "Effects of Tolvaptan, a Vasopressin Antagonist, in Patients Hospitalized With Worsening Heart Failure A Randomized Controlled Trial," JAMA., 291:1963-1971 (2004).
Go et al. "Heart Disease and Stroke Statistics—2014 Update—A Report From the American Heart Association," Circulation, 128:1-267 (2014).
Guillevin et al., "Understanding the impact of pulmonary arterial hypertension on patients' and carers' lives," Eur Respir Rev., 22:535-542 (2013).
Guyton et al., "Effect of Elevated Left Atrial Pressure and Decreased Plasma Protein Concentration on the Development of Pulmonary Edema," Circulation Research, 7:643-657 (1959).
Hasenfub, et al., A Transcatheter Intracardiac Shunt Device for Heart Failure with Preserved Ejection Fraction (Reduce LAP-HF): A Multicentre, Open-Label, Single-Arm, Phase 1 Trial, www. thelancet.com, 387:1298-1304 (2016).
Hoeper et al., "Definitions and Diagnosis of Pulmonary Hypertension," J Am Coll Cardiol., 62(5):D42-D50 (2013).
Hogg et al., "Heart Failure With Preserved Left Ventricular Systolic Function. Epidemiology, Clinical Characteristics, and Prognosis," J Am Coll Cardiol., 43(3):317-327 (2004).
Howell et al., "Congestive heart failure and outpatient risk of venous thromboembolism: A retrospective, case-control study," Journal of Clinical Epidemiology, 54:810-816 (2001).
Huang et al., "Remodeling of the chronic severely failing ischemic sheep heart after coronary microembolization: functional, energetic, structural, and cellular responses," Am J Physiol Heart Circ Physiol., 286:H2141-H2150 (2004).
Humbert et al., "Pulmonary Arterial Hypertension in France— Results from a National Registry," Am J Respir Crit Care Med., 173:1023-1030 (2006).
International Search Report & Written Opinion dated Nov. 7, 2016 in Int'l PCT Patent Appl. Serial No. PCT/IB2016/052561 (1810).
International Search Report & Written Opinion dated May 29, 2018 in Int'l PCT Patent Appl. Serial No. PCT/IB2018/051385 (1310).
International Search Report & Written Opinion dated Feb. 6, 2013 in Int'l PCT Patent Appl. No. PCT/IB2012/001859, 12 pages (0810).
International Search Report & Written Opinion dated Feb. 7, 2020 in Int'l PCT Patent Appl. Serial No. PCT/IB2019/060257 (1410).
International Search Report & Written Opinion dated May 13, 2019 in Int'l PCT Patent Appl. No. PCT/IB2019/050452 (1610).

(56) References Cited

OTHER PUBLICATIONS

International Search Report & Written Opinion dated Jul. 14, 2020 in Int'l PCT Patent Appl. Serial No. PCT/IB2020/053832 (1210).
International Search Report & Written Opinion dated Jul. 20, 2020 in Int'l PCT Patent Appl. Serial No. PCT/IB2020/054699 (1710).
International Search Report & Written Opinion dated Jul. 23, 2021 in Int'l PCT Patent Appl. Serial No. PCT/IB2021/053594 (1910).
International Search Report & Written Opinion dated Aug. 12, 2020 in Int'l PCT Patent Appl. Serial No. PCT/IB2020/053118 (1010).
International Search Report & Written Opinion dated Aug. 28, 2012 in Int'l PCT Patent Appl. No. PCT/IL2011/000958 (0710).
International Search Report & Written Opinion dated Sep. 21, 2020 in Int'l PCT Patent Appl. Serial No. PCT/IB2020/054306 (1510).
International Search Report & Written Opinion dated Oct. 26, 2007 in Int'l PCT Patent Appl. Serial No. PCT/IB07/50234 (0610).
Jessup et al. "2009Focused Update: ACC/AHA Guidelines for the Diagnosis and Management of Heart Failure in Adults: A Report of the American College of Cardiology Foundation/American Heart Association Task Force on Practice Guidelines: Developed in Collaboration With the International Society for Heart and Lung Transplantation," J. Am. Coll. Cardiol., 53:1343-1382 (2009).
Jiang, G., "Design challenges of implantable pressure monitoring system," Frontiers in Neuroscience, 4(29):1-4 (2010).
Kane et al., "Integration of clinical and hemodynamic parameters in the prediction of long-term survival in patients with pulmonary arterial hypertension," Chest, 139(6):1285-1293 (2011) (Abstract Only).
Kaye et al., "Effects of an Interatrial Shunt on Rest and Exercise Hemodynamics: Results of a Computer Simulation in Heart Failure," Journal of Cardiac Failure, 20(3): 212-221 (2014).
Kaye et al., "One-Year Outcomes After Transcatheter Insertion of an Interatrial Shunt Device for the Management of Heart Failure With Preserved Ejection Fraction," Circulation: Heart Failure, 9(12):e003662 (2016).
Keogh et al., "Interventional and Surgical Modalities of Treatment in Pulmonary Hypertension," J Am Coll Cardiol., 54:S67-77 (2009).
Keren, et al. Methods and Apparatus for Reducing Localized Circulatory System Pressure,., Jan. 7, 2002 (pp. 16).
Kretschmar et al., "Shunt Reduction With a Fenestrated Amplatzer Device," Catheterization and Cardiovascular Interventions, 76:564-571 (2010).
Kropelnicki et al., "CMOS-compatible ruggedized high-temperature Lamb wave pressure sensor," J. Micromech. Microeng., 23:085018 pp. 1-9 (2013).
Krumholz et al., "Patterns of Hospital Performance in Acute Myocardial Infarction and Heart Failure 30-Day Mortality and Readmission," Circ Cardiovasc Qual Outcomes, 2:407-413 (2009).
Kulkarni et al., "Lutembacher's syndrome," J Cardiovasc Did Res., 3(2):179-181 (2012).
Kurzyna et al., "Atrial Septostomy in Treatment of End-Stage Right Heart Failure in Patients With Pulmonary Hypertension," Chest, 131:977-983 (2007).
Lammers et al., "Efficacy and Long-Term Patency of Fenerstrated Amplatzer Devices in Children," Catheter Cardiovasc Interv., 70:578-584 (2007).
Lindenfeld et al. "Executive Summary: HFSA 2010 Comprehensive Heart Failure Practice Guideline," J. Cardiac Failure, 16(6):475-539 (2010).
Luo, Yi, *Selective and Regulated RF Heating of Stent Toward Endohyperthermia Treatment of In-Stent Restenosis*, A Thesis Submitted in Partial Fulfillment of The Requirements For The Degree of Master of Applied Science in The Faculty of Graduate and Postdoctoral Studies (Electrical and Computer Engineering), The University of British Columbia, Vancouver, Dec. 2014.
MacDonald et al., "Emboli Enter Penetrating Arteries of Monkey Brain in Relation to Their Size," Stroke, 26:1247-1251 (1995).
Maluli et al., "Atrial Septostomy: A Contemporary Review," Clin. Cardiol., 38(6):395-400 (2015).

Maurer et al., "Rationale and Design of the Left Atrial Pressure Monitoring to Optimize Heart Failure Therapy Study (LAPTOP-HF)," Journal of Cardiac Failure., 21(6): 479-488 (2015).
McClean et al., "Noninvasive Calibration of Cardiac Pressure Transducers in Patients With Heart Failure: An Aid to Implantable Hemodynamic Monitoring and Therapeutic Guidance," J Cardiac Failure, 12(7):568-576 (2006).
McLaughlin et al., "Management of Pulmonary Arterial Hypertension," J Am Coll Cardiol., 65(18):1976-1997 (2015).
McLaughlin et al., "Survival in Primary Pulmonary Hypertension—The Impact of Epoprostenol Therapy.," Circulation, 106:1477-1482 (2002).
Mu et al., "Dual mode acoustic wave sensor for precise pressure reading," Applied Physics Letters, 105:113507-1-113507-5 (2014).
Nagaraju et al., "A 400µW Differential FBAR Sensor Interface IC with digital readout," IEEE., pp. 218-221 (2015).
Noordegraaf et al., "The role of the right ventricle in pulmonary arterial hypertension," Eur Respir Rev., 20(122):243-253 (2011).
O'Byrne et al., "The effect of atrial septostomy on the concentration of brain-type natriuretic peptide in patients with idiopathic pulmonary arterial hypertension," Cardiology in the Young, 17(5):557-559 (2007) (Abstract Only).
Oktay et al., "The Emerging Epidemic of Heart Failure with Preserved Ejection Fraction," Curr Heart Fail Rep., 10(4):1-17 (2013).
Owan et al., "Trends in Prevalence and Outcome of Heart Failure with Preserved Ejection Fraction," N Engl J Med., 355:251-259 (2006).
Paitazoglou et al., "Title: The AFR-Prelieve Trial: A prospective, non-randomized, pilot study to assess the Atrial Flow Regulator (AFR) in Heart Failure Patients with either preserved or reduced ejection fraction," EuroIntervention, 28:2539-50 (2019).
Park Blade Septostomy Catheter Instructions for Use, Cook Medical, 28 pages, Oct. 2015.
Partial Supplemental European Search Report dated Dec. 11, 2018 in EP Patent Appl. Serial No. 16789391.6 (1830).
Peters et al., "Self-fabricated fenestrated Amplatzer occluders for transcatheter closure of atrial septal defect in patients with left ventricular restriction: midterm results," Clin Res Cardiol., 95:88-92 (2006).
Ponikowski et al., "2016 ESC Guidelines for the diagnosis and treatment of acute and chronic heart failure. The Task Force for the diagnosis and treatment of acute and chronic heart failure of the European Society of Cardiology (ESC)," Eur Heart J., doi: 10.1093/eurheartj/ehw128 (2016).
Potkay, J. A., "Long term, implantable blood pressure monitoring systems," Biomed Microdevices, 10:379-392 (2008).
Pretorious et al., "An Implantable Left Atrial Pressure Sensor Lead Designed for Percutaneous Extraction Using Standard Techniques," PACE, 00:1-8 (2013).
Rajeshkumar et al., "Atrial septostomy with a predefined diameter using a novel occlutech atrial flow regulator improves symptoms and cardiac index in patients with severe pulmonary arterial hypertension," Catheter Cardiovasc Interv., 1-9 (2017).
Rich et al., "Atrial Septostomy as Palliative Therapy for Refractory Primary Pulmonary Hypertension," Am J Cardiol., 51:1560-1561 (1983).
Ritzema et al., "Direct Left Atrial Pressure Monitoring in Ambulatory Heart Failure Patients—Initial Experience With a New Permanent Implantable Device," Circulation, 116:2952-2959 (2007).
Ritzema et al., "Physician-Directed Patient Self-Management of Left Atrial Pressure in Advanced Chronic Heart Failure," Circulation, 121:1086-1095 (2010).
Roberts et al., "Integrated microscopy techniques for comprehensive pathology evaluation of an implantable left atrial pressure sensor," J Histotechnology, 36(1):17-24 (2013).
Rodes-Cabau et al., "Interatrial Shunting for Heart Failure Early and Late Results From the First-in-Human Experience With the V-Wave System," J Am Coll Cardiol Intv., 11:2300-2310.doi :10.1016/j.cin. 2018.07.001 (2018).
Rosenquist et al., Atrial Septal Thickness and Area in Normal Heart Specimens and in Those With Ostium Secundum Atrial Septal Defects, J. Clin. Ultrasound, 7:345-348 (1979).

(56) References Cited

OTHER PUBLICATIONS

Ross et al., "Interatrial Communication and Left Atrial Hypertension—A Cause of Continuous Murmur," Circulation, 28:853-860 (1963).
Rossignol, et al., Left-to-Right Atrial Shunting: New Hope for Heart Failure, www.thelancet.com, 387:1253-1255 (2016).
Sandoval et al., "Effect of atrial septostomy on the survival of patients with severe pulmonary arterial hypertension," Eur Respir J., 38:1343-1348 (2011).
Sandoval et al., "Graded Balloon Dilation Atrial Septostomy in Severe Primary Pulmonary Hypertension—A Therapeutic Alternative for Patients Nonresponsive to Vasodilator Treatment," JACC, 32(2):297-304 (1998).
Schiff et al., "Decompensated heart failure: symptoms, patterns of onset, and contributing factors," Am J. Med., 114(8):625-630 (2003) (Abstract Only).
Schneider et al., "Fate of a Modified Fenestration of Atrial Septal Occluder Device after Transcatheter Closure of Atrial Septal Defects in Elderly Patients," J Interven Cardiol., 24:485-490 (2011).
Scholl et al., "Surface Acoustic Wave Devices for Sensor Applications," Phys Status Solidi Appl Res., 185(1):47-58 (2001) (Abstract Only).
Setoguchi et al., "Repeated hospitalizations predict mortality in the community population with heart failure," Am Heart J., 154:260-266 (2007).
Shah et al., "Heart Failure With Preserved, Borderline, and Reduced Ejection Fraction—5-Year Outcomes," J Am Coll Cardiol., https://doi.org/10.1016/j.jacc.2017.08.074 (2017).
Shah et al., "One-Year Safety and Clinical Outcomes of a Transcatheter Interatrial Shunt Device for the Treatment of Heart Failure With Preserved Ejection Fraction in the Reduce Elevated Left Atrial Pressure in Patients With Heart Failure (Reduce LAP-HF 1) Trial—A Randomized Clinical Trial," JAMA Cardiol. doi:10.1001/jamacardio.2018.2936 (2018).
Sitbon et al., "Selexipag for the Treatment of Pulmonary Arterial Hypertension.," N Engl J Med., 373(26):2522-2533 (2015).
Sitbon et al., "Epoprostenol and pulmonary arterial hypertension: 20 years of clinical experience," Eur Respir Rev., 26:160055:1-14 (2017).
Steimle et al., "Sustained Hemodynamic Efficacy of Therapy Tailored to Reduce Filling Pressures in Survivors With Advanced Heart Failure," Circulation, 96:1165-1172 (1997).
Stevenson et al., "The Limited Reliability of Physical Signs for Estimating Hemodynamics in Chronic Heart Failure," JAMA, 261(6):884-888 (1989) (Abstract Only).
Su et al., "A film bulk acoustic resonator pressure sensor based on lateral field excitation," International Journal of Distributed Sensor Networks, 14(11):1-8 (2018).
Supplementary European Search Report dated Nov. 13, 2009 in EP Patent Appl. Serial No. 05703174.2 (0430).
Thenappan et al., "Evolving Epidemiology of Pulmonary Arterial Hypertension," Am J Resp Critical Care Med., 186:707-709 (2012).
Tomai et al., "Acute Left Ventricular Failure After Transcatheter Closure of a Secundum Atrial Septal Defect in a Patient With Coronary Artery Disease: A Critical Reappraisal," Catheterization and Cardiovascular Interventions, 55:97-99 (2002).
Torbicki et al., "Atrial Septostomy," The Right Heart, 305-316 (2014).
Troost et al., "A Modified Technique of Stent Fenestration of the Interatrial Septum Improves Patients With Pulmonary Hypertension," Catheterization and Cardiovascular Interventions, 73:173179 (2009).
Troughton et al., "Direct Left Atrial Pressure Monitoring in Severe Heart Failure: Long-Term Sensor Performance," J. of Cardiovasc. Trans. Res., 4:3-13 (2011).
Vank-Noordegraaf et al., "Right Heart Adaptation to Pulmonary Arterial Hypertension—Physiology and Pathobiology," J Am Coll Cardiol., 62(25):D22-33 (2013).

Verel et al., "Comparison of left atrial pressure and wedge pulmonary capillary pressure—Pressure gradients between left atrium and left ventricle," British Heart J., 32:99-102 (1970).
Viaene et al., "Pulmonary oedema after percutaneous ASD-closure," Acta Cardiol., 65(2):257-260 (2010).
Wang et al., "A Low Temperature Drifting Acoustic Wave Pressure Sensor with an Integrated Vacuum Cavity for Absolute Pressure Sensing," Sensors, 20(1788):1-13 (2020).
Wang et al., "Tire Pressure Monitoring System and Wireless Passive Surface Acoustic Wave Sensor," Appl Mech Mater., 536(537):333-337 (2014).
Warnes et al., "ACC/AHA 2008 Guidelines for the Management of Adults With Congenital Heart Disease—A Report of the American College of Cardiology/American Heart Association Task Force on Practice Guidelines (Writing Committee to Develop Guidelines on the Management of Adults With Congenital Heart Disease)," JACC, 52(23):e143-e263 (2008).
Webb et al., "Atrial Septal Defects in the Adult Recent Progress and Overview," Circulation, 114:1645-1653 (2006).
Wiedemann, H.R., "Earliest description by Johann Friedrich Meckel, Senior (1750) of what is known today as Lutembacher syndrome (1916)," Am J Med Genet., 53(1):59-64 (1994) (Abstract Only).
Written Opinion of the International Searching Authority dated Apr. 7, 2008 in Int'l PCT Patent Appl. Serial No. PCT/IL05/00131 (0410).
Yantchev et al., "Thin Film Lamb Wave Resonators in Frequency Control and Sensing Applications: A Review," Journal of Micromechanics and Microengineering, 23(4):043001 (2013).
Zhang et al., "Acute left ventricular failure after transcatheter closure of a secundum atrial septal defect in a patient with hypertrophic cardiomyopathy," Chin Med J., 124(4):618-621 (2011).
Zhang et al., "Film bulk acoustic resonator-based high-performance pressure sensor integrated with temperature control system," J Micromech Microeng., 27(4):1-10 (2017).
U.S. Appl. No. 09/839,643 / U.S. Pat. No. 8,091,556, filed Apr. 20, 2001 / Jan. 10, 2012.
U.S. Appl. No. 10/597,666 / U.S. Pat. No. 8,070,708, filed Jun. 20, 2007 / Dec. 6, 2011.
U.S. Appl. No. 12/223,080 / U.S. Pat. No. 9,681,948, filed Jul. 16, 2014 / Jun. 20, 2017.
U.S. Appl. No. 13/107,832 / U.S. Pat. No. 8,235,933, filed May 13, 2011 / Aug. 7, 2012.
U.S. Appl. No. 13/107,843 / U.S. Pat. No. 8,328,751, filed May 13, 2011 / Dec. 11, 2012.
U.S. Appl. No. 13/108,672 / U.S. Pat. No. 9,724,499, filed May 16, 2011 / Aug. 8, 2017.
U.S. Appl. No. 13/108,698, filed Jun. 16, 2011.
U.S. Appl. No. 13/108,850, filed May 16, 2011.
U.S. Appl. No. 13/108,880 / U.S. Pat. No. 8,696,611, filed May 16, 2011 / Apr. 15, 2014.
U.S. Appl. No. 13/193,309 / U.S. Pat. No. 9,629,715, filed Aug. 28, 2011 / Apr. 25, 2017.
U.S. Appl. No. 13/193,335 / U.S. Pat. No. 9,034,034, filed Jul. 28, 2011 / May 19, 2015.
U.S. Appl. No. 13/708,794 / U.S. Pat. No. 9,943,670, filed Dec. 7, 2012 / Apr. 17, 2018.
U.S. Appl. No. 14/154,080 / U.S. Pat. No. 10,207,087, filed Jan. 13, 2014 / Feb. 19, 2019.
U.S. Appl. No. 14/154,088, filed Jan. 13, 2014.
U.S. Appl. No. 14/154,093, filed Jan. 13, 2014.
U.S. Appl. No. 14/227,982 / U.S. Pat. No. 9,707,382, filed Mar. 27, 2014 / Jul. 18, 2017.
U.S. Appl. No. 14/282,615 / U.S. Pat. No. 9,713,696, filed May 20, 2014 / Jul. 25, 2017.
U.S. Appl. No. 14/712,801 / U.S. Pat. No. 9,980,815, filed May 14, 2015 / May 29, 2018.
U.S. Appl. No. 15/449,834 / U.S. Pat. No. 10,076,403, filed Mar. 3, 2017 / Sep. 18, 2018.
U.S. Appl. No. 15/492,852, filed Apr. 20, 2017.
U.S. Appl. No. 15/608,948, filed May 30, 2017.
U.S. Appl. No. 15/624,314, filed Jun. 15, 2017.
U.S. Appl. No. 15/650,783, filed Jul. 14, 2017.
U.S. Appl. No. 15/656,936, filed Jul. 21, 2017.

(56) References Cited

OTHER PUBLICATIONS

U.S. Appl. No. 15/668,622, filed Aug. 3, 2017.
U.S. Appl. No. 15/798,250, filed Oct. 30, 2017.
U.S. Appl. No. 15/988,888, filed May 24, 2018.
U.S. Appl. No. 16/130,978 / U.S. Pat. No. 10,251,750, filed Sep. 13, 2018 / Apr. 9. 2019.
U.S. Appl. No. 16/130,988, filed Sep. 13, 2018.
U.S. Appl. No. 16/205,213, filed Nov. 29, 2018.
U.S. Appl. No. 16/374,698, filed Apr. 3, 2019.
U.S. Appl. No. 16/395,209, filed Apr. 25, 2019.
Ando et al., "Left ventricular decompression through a patent foramen ovale in a patient with hypertropic cardiomyopathy: A case report," Cardiovascular Ultrasound 2: 1-7 (2004).
Atrium Advanta V12, Balloon Expandable Covered Stent, Improving Patient Outcomes with An Endovascular Approach, Brochure—8 pages, Getinge (2017).
Braunwald, Heart Disease, Chapter 6, p. 186.
Bridges, et al., The Society of Thoracic Surgeons Practice Guideline Series: Transmyocardial Laser Revascularization, Ann Thorac Surg., 77:1494-1502 (2004).
Bristow et al., Improvement in cardiac myocyte function by biological effects of medical therapy: a new concept in the treatment of heart failure, European Heart Journal 16 (Suppl.F): 20-31 (1995).
Case et al., "Relief of High Left-Atrial Pressure in Left-Ventricular Failure," Lancet, pp. 841-842 (Oct. 14, 1964).
Coats et al., "Controlled trial of physical training in chronic heart failure: Exercise performance, hemodynamics, ventilation and autonomic function," Circulation 85:2119-2131 (1992).
Partial International Search dated Aug. 17, 2017 in Int'l PCT Patent Appl. Serial No. PCT/IB2017/053188.
Davies et al., "Reduced contraction and altered frequency response of isolated ventricular myocytes from patients with heart failure," Circulation 92: 2540-2549 (1995).
Ennezat et al., An unusual case of low-flow, low-gradient severe aortic stenosis: Left-to-right shunt due to atrial septal defect, Cardiology 113(2): 146-148 (2009).
Ewert et al., "Acute left heart failure after interventional occlusion of an atrial septal defect," Z Kardiol. 90(5): 362-366 (May 2001).
Ewert et al., Masked Left Ventricular Restriction in Elderly Patients With Atrial Septal Defects: A Contraindication for Closure?, Catheterization and Cardiovascular Interventions 52: 177-180 (2001).
Extended EP Search Report dated Sep. 19, 2016 in EP Patent Application Serial No. 16170281.6.
Extended European Search Report dated Jan. 8, 2015 in EP Patent Appl No. 10772089.8.
Geiran et al., "Changes in cardiac dynamics by opening an interventricular shunt in dogs," J. Surg. Res. 48(1): 6-12 (Jan. 1990).
Gelernter-Yaniv et al., "Transcatheter closure of left-to-right interatrial shunts to resolve hypoxemia," Conginit. Heart Dis. 31 (1) 47-53 (Jan. 2008).
Gewillig et al., "Creation with a stent of an unrestrictive lasting atrial communication," Cardio. Young 12(4): 404-407 (2002).
International Search Report & Written Opinion dated May 29, 2018 in Int'l PCT Patent Appl. Serial No. PCTIB2018/051355.
International Search Report for PCT/IL2005/000131, 3 pages (dated Apr. 7, 2008).
International Search Report for PCT/IL2010/000354 dated Aug. 25, 2010 (1 pg).
Int'l Search Report & Written Opinion dated Feb. 16, 2015 in Int'l PCT Patent Appl. Serial No. PCT/IB2014/001771.
Khositseth et al., Transcatheter Amplatzer Device Closure of Atrial Septal Defect and Patent Foramen Ovale in Patients With Presumed Paradoxical Embolism, Mayo Clinic Proc., 79:35-41 (2004).
Kramer et al., "Controlled study of captopril in chronic heart failure: A rest and exercise hemodynamic study," Circulation 67(4): 807-816 (1983).
Lai et al., Bidirectional Shunt Through a Residual Atrial Septal Defect After Percutaneous Transvenous Mitral Commissurotomy, Cardiology 83(3): 205-207 (1993).
Lemmer et al., "Surgical implications of atrial septal defect complicating aortic balloon valvuloplasty," Ann Thorac. Surg. 48(2): 295-297 (Aug. 1989).
Merriam-Webster "Definition of'Chamber'," O-line Dictionary 2004, Abstract.
Park, et al., Blade Atrial Septostomy: Collaborative Study, Circulation, 66(2):258-266 (1982).
Roven et al., "Effect of Compromising Right Ventricular Function in Left Ventricular Failure by Means of Interatrial and Other Shunts," American Journal Cardiology, 24:209-219 (1969).
Salehian et al., Improvements in Cardiac Form and Function After Transcatheter Closure of Secundum Atrial Septal Defects, Journal of the American College of Cardiology, 45(4):499-504 (2005).
Schmitto et al., Chronic heart failure induced by multiple sequential coronary microembolization in sheep, The International Journal of Artificial Organs, 31(4):348-353 (2008).
Schubert et al., Left Ventricular Conditioning in the Elderly Patient to Prevent Congestive Heart Failure After Transcatheter Closure of the Atrial Septal Defect, Catheterization and Cardiovascular Interventions,64(3): 333-337 (2005).
Stormer et al., Comparative Study of n vitro Flow Characteristics Between a Human Aortic Valve and a Designed Aortic Valve and Six Corresponding Types of Prosthetic Heart Valves, European Surgical Research 8(2): 117-131 (1976).
Stumper et al., "Modified technique of stent fenestration of the atrial septum," Heart 89: 1227-1230 (2003).
Trainor et al., Comparative Pathology of an Implantable Left Atrial Pressure Sensor, ASAIO Journal, Clinical Cardiovascular/Cardiopulmonary Bypass, 59(5):486-92 (2013).
Zhou et al., Unidirectional Valve Patch for Repair of Cardiac Septal Defects With Pulmonary Hypertension, Annals of Thoracic Surgeons, 60:1245-1249 (1995).

* cited by examiner

ASYMMETRIC SHUNT FOR REDISTRIBUTING ATRIAL BLOOD VOLUME

CROSS-REFERENCE TO RELATED APPLICATIONS

This application is a continuation-in-part application of U.S. patent application Ser. No. 16/130,988, filed Sep. 13, 2018, which is a continuation of U.S. patent application Ser. No. 15/449,834, filed Mar. 3, 2017, now U.S. Pat. No. 10,076,403, the entire contents of each of which are incorporated by reference herein.

FIELD OF THE INVENTION

This application generally relates to percutaneously placed asymmetric implants and methods for redistributing blood from one cardiac chamber to another to address pathologies such as heart failure ("HF"), myocardial infarction ("MI") and pulmonary arterial hypertension ("PAH").

BACKGROUND OF THE INVENTION

Heart failure is the physiological state in which cardiac output is insufficient to meet the needs of the body or to do so only at a higher filing pressure. There are many underlying causes of HF, including myocardial infarction, coronary artery disease, valvular disease, hypertension, and myocarditis. Chronic heart failure is associated with neurohormonal activation and alterations in autonomic control. Although these compensatory neurohormonal mechanisms provide valuable support for the heart under normal physiological circumstances, they also play a fundamental role in the development and subsequent progression of HF.

For example, one of the body's main compensatory mechanisms for reduced blood flow in HF is to increase the amount of salt and water retained by the kidneys. Retaining salt and water, instead of excreting it via urine, increases the volume of blood in the bloodstream and helps to maintain blood pressure. However, the larger volumes of blood also cause the heart muscle, particularly the ventricles, to become enlarged. As the heart chambers become enlarged, the wall thickness decreases and the heart's contractions weaken, causing a downward spiral in cardiac function. Another compensatory mechanism is vasoconstriction of the arterial system, which raises the blood pressure to help maintain adequate perfusion, thus increasing the load that the heart must pump against.

In low ejection fraction ("EF") heart failure, high pressures in the heart result from the body's attempt to maintain the high pressures needed for adequate peripheral perfusion. However, as the heart weakens as a result of such high pressures, the disorder becomes exacerbated. Pressure in the left atrium may exceed 25 mmHg, at which stage, fluids from the blood flowing through the pulmonary circulatory system transudate or flow out of the pulmonary capillaries into the pulmonary interstitial spaces and into the alveoli, causing lung congestion and if untreated the syndrome of acute pulmonary edema and death.

Table 1 lists typical ranges of right atrial pressure ("RAP"), right ventricular pressure ("RVP"), left atrial pressure ("LAP"), left ventricular pressure ("LVP"), cardiac output ("CO"), and stroke volume ("SV") for a normal heart and for a heart suffering from HF. In a normal heart beating at around 70 beats/minute, the stroke volume needed to maintain normal cardiac output is about 60 to 100 milliliters. When the preload, after-load, and contractility of the heart are normal, the pressures required to achieve normal cardiac output are listed in Table 1. In a heart suffering from HF, the hemodynamic parameters change (as shown in Table 1) to maintain peripheral perfusion.

TABLE 1

| Parameter | Normal Range | HF Range |
| --- | --- | --- |
| RAP (mmHg) | 2-6 | 6-20 |
| RVSP (mmHg) | 15-25 | 20-80 |
| LAP (mmHg) | 6-12 | 15-50 |
| LVEDP (mmHg) | 6-12 | 15-50 |
| CO (liters/minute) | 4-8 | 2-6 |
| SV (milliliters/beat) | 60-100 | 30-80 |

HF is generally classified as either systolic heart failure ("SHF") or diastolic heart failure ("DHF"). In SHF, the pumping action of the heart is reduced or weakened. A common clinical measurement is the ejection fraction, which is a function of the blood ejected out of the left ventricle (stroke volume) divided by the maximum volume in the left ventricle at the end of diastole or relaxation phase. A normal ejection fraction is greater than 50%. Systolic heart failure generally causes a decreased ejection fraction of less than 40%. Such patients have heart failure with reduced ejection fraction ("HFrEF"). A patient with HFrEF may usually have a larger left ventricle because of a phenomenon called "cardiac remodeling" that occurs secondarily to the higher ventricular pressures.

In DHF, the heart generally contracts normally, with a normal ejection fraction, but is stiffer, or less compliant, than a healthy heart would be when relaxing and filling with blood. Such patients are said to have heart failure with preserved ejection fraction ("HFpEF"). This stiffness may impede blood from filling the heart and produce backup into the lungs, which may result in pulmonary venous hypertension and lung edema. HFpEF is more common in patients older than 75 years, especially in women with high blood pressure.

Both variants of HF have been treated using pharmacological approaches, which typically involve the use of vasodilators for reducing the workload of the heart by reducing systemic vascular resistance, as well as diuretics, which inhibit fluid accumulation and edema formation, and reduce cardiac filling pressure. No pharmacological therapies have been shown to improve morbidity or mortality in HFpEF whereas several classes of drugs have made an important impact on the management of patients with HFrEF, including renin-angiotensin antagonists, beta blockers, and mineralocorticoid antagonists. Nonetheless, in general, HF remains a progressive disease and most patients have deteriorating cardiac function and symptoms over time. In the U.S., there are over 1 million hospitalizations annually for acutely worsening HF and mortality is higher than for most forms of cancer.

In more severe cases of HFrEF, assist devices such as mechanical pumps are used to reduce the load on the heart by performing all or part of the pumping function normally done by the heart. Chronic left ventricular assist devices ("LVAD"), and cardiac transplantation, often are used as measures of last resort. However, such assist devices typically are intended to improve the pumping capacity of the heart, to increase cardiac output to levels compatible with normal life, and to sustain the patient until a donor heart for transplantation becomes available. Such mechanical devices enable propulsion of significant volumes of blood (liters/ min), but are limited by a need for a power supply, relatively large pumps, and pose a risk of hemolysis, thrombus formation, and infection. Temporary assist devices, intra-aortic balloons, and pacing devices have also been used.

Various devices have been developed using stents to modify blood pressure and flow within a given vessel, or between chambers of the heart. For example, U.S. Pat. No. 6,120,534 to Ruiz is directed to an endoluminal stent for regulating the flow of fluids through a body vessel or organ, for example, for regulating blood flow through the pulmonary artery to treat congenital heart defects. The stent may include an expandable mesh having lobed or conical portions joined by a constricted region, which limits flow through the stent. The mesh may comprise longitudinal struts connected by transverse sinusoidal or serpentine connecting members. Ruiz is silent on the treatment of HF or the reduction of left atrial pressure.

U.S. Pat. No. 6,468,303 to Amplatz et al. describes a collapsible medical device and associated method for shunting selected organs and vessels. Amplatz describes that the device may be suitable to shunt a septal defect of a patient's heart, for example, by creating a shunt in the atrial septum of a neonate with hypoplastic left heart syndrome ("HLHS"). That patent also describes that increasing mixing of pulmonary and systemic venous blood improves oxygen saturation, and that the shunt may later be closed with an occluding device. Amplatz is silent on the treatment of HF or the reduction of left atrial pressure, as well as on means for regulating the rate of blood flow through the device.

Implantable interatrial shunt devices have been successfully used in patients with severe symptomatic heart failure. By diverting or shunting blood from the left atrium ("LA") to the right atrium ("RA"), the pressure in the left atrium is lowered or prevented from elevating as high as it would otherwise (left atrial decompression). Such an accomplishment would be expected to prevent, relieve, or limit the symptoms, signs, and syndromes associated with pulmonary congestion. These include severe shortness of breath, pulmonary edema, hypoxia, the need for acute hospitalization, mechanical ventilation, and death.

Shunt flow is generally governed by the pressure gradient between the atria, and by the fluid mechanical properties of the shunt device. The latter are typically affected by the shunt's geometry and material composition. For example, the general flow properties of similar shunt designs have been shown to be related to the mean interatrial pressure gradient and the effective orifice diameter.

Percutaneous implantation of interatrial shunts generally requires transseptal catheterization immediately preceding shunt device insertion. The transseptal catheterization system is placed, from an entrance site in the femoral vein, across the interatrial septum in the region of fossa ovalis ("FO"), which is the central and thinnest region of the interatrial septum. This is the same general location where a congenital secundum atrial septal defect ("ASD") would be located. The FO in adults is typically 15-20 mm in its major axis dimension and ≤3 mm in thickness, but in certain circumstances may be up to 10 mm thick. LA chamber access may be achieved using a host of different techniques familiar to those skilled in the art, including but not limited to: needle puncture, stylet puncture, screw needle puncture, and radiofrequency ablation. The passageway between the two atria is dilated to facilitate passage of a shunt device having a desired orifice size. Dilation generally is accomplished by advancing a tapered sheath/dilator catheter system or inflation of an angioplasty-type balloon across the FO.

U. S. Patent Publication No. 2005/0165344 to Dobak, III describes apparatus for treating heart failure that includes a tubular conduit having an emboli filter or valve, the device configured to be positioned in an opening in the atrial septum of the heart to allow flow from the left atrium into the right atrium. Dobak discloses that shunting of blood may reduce left atrial pressures, thereby preventing pulmonary edema and progressive left ventricular dysfunction, and reducing LVEDP. Dobak describes that the device may include deployable retention struts, such as metallic arms that exert a slight force on the atrial septum on both sides and pinch or clamp the device to the septum.

Two types of percutaneously implantable shunts have been described in the medical and patent literature. In short-term, small-size clinical trials, both types have been shown to be associated with improvements in symptoms, quality of life measurements, and exercise capacity. Both shunts also have observed and theoretical drawbacks, which may limit their effectiveness and use.

The first type of shunt is henceforth referred to as an orifice-plate mesh shunt. Orifice-plate mesh shunts comprise a metallic mesh that wraps around both sides of the septum with a hole in the center, and anatomically mimics the location and geometrical characteristics of a small congenital secundum ASD. The shunt geometry generally resembles a thin plate with a hole in it. In most embodiments, the "plate" comprises both mesh material and atrial septal tissue encased by the mesh. One example of such devices, designed by Corvia Medical, Inc., Tewksbury Mass., consists of a self-expanding nitinol mesh that forms a pair of disc-like flanges with an open orifice in the center. The maximal diameter of the discs is 19.4 mm and the orifice diameter is 8 mm. Each disc flange has multiple truss-like legs that deploy into a preset configuration that wraps around the LA and RA sides of the interatrial septum and applies a clamping force to the tissue.

Another example of such a mesh type device, developed by Occlutech International AB, Helsingborg, Sweden, resembles a dual-disc occluder used for closing congenital secundum ASDs, which additionally includes a short open barrel orifice in the center that connects the two discs.

A major benefit of the foregoing orifice-plate mesh shunts over other shunt designs is simplicity of manufacture. Although relatively simple in theory and construction, orifice-plate mesh type shunts have several important drawbacks that are expected to reduce their overall potential for clinical safety and effectiveness.

A first drawback of orifice-plate devices is the susceptibility to narrow or close during the post-implantation healing period. For example, neoendocardial tissue ingrowth, referred to as pannus, grows from the underlining tissue to cover the mesh and narrow or partially occlude the shunt orifice. During the period following implantation, local trauma caused by crossing and dilating the FO, plus the chronic effects of continuous pressure applied by the mesh material on the septal tissue, provoke a localized healing response. This response entails activation of an inflammatory process, attracting lymphocytes and macrophages to the area of tissue injury. These inflammatory cells in turn release a variety of cytokines that signal fibroblasts and smooth-muscle cells from the wound margins to dedifferentiate, migrate, proliferate and encapsulate affected portions of the implanted device. The fibroblasts and smooth muscle cells then secrete extracellular matrix material composed of collagen and proteoglycans, which extracellular matrix forms the bulk of the pannus. The duration of this healing phase in humans is typically up to 6-9 months, but may be longer if there is a chronic source for tissue injury such as device compression or erosion of adjacent tissue. Eventually this pannus is covered with neoendothelial cells, causing the pannus growth to stop or stabilize. In the long term, the collagen of the pannus remodels, but generally retains its space occupying properties. Such tissue ingrowth typically spreads over the surfaces of the implant's struts, mesh, or discs, and may substantially narrow the orifice lumen or even entirely occlude the shunt. Narrowing or occlusion of the shunt prevents LA decompression and limits any positive effect for the patient.

The degree of luminal narrowing may be quite variable between patients due to differences in the severity of local injury—the more injury, the more exaggerated the pannus formation. Also, variability results from differences in host wound healing responses. For example, the amount and character of extracellular matrix may affect the duration of healing and amount of material deposited. Thus, for an orifice-plate mesh shunt, the eventual orifice lumen size will be highly variable. These processes will be familiar to one skill in the art as it is generally analogous to the type of late lumen loss that occurs in arteries when bare metal stents are used to treat atherosclerotic stenosis.

In a trial described in the publication, "A Transcatheter Intracardiac Shunt Device for Heart Failure with Preserved Ejection Fraction (REDUCE LAP-HF): A Multicentre, Open-label, Single-arm, Phase 1. Trial" by Hasenfuss, et al., 14 of 64 patients implanted with an orifice-plate mesh shunt device had no demonstrable flow across the shunt on transthoracic echocardiographic Doppler imaging at 6 months after implantation. It was not reported whether the shunts were occluded or if the imaging study was simply too technically difficult to tell for certain. Although additional interventional cardiology procedures may be undertaken to restore lost luminal patency, such procedures may pose unacceptable risks, including death and stroke from embolization of the orifice-clogging material, and there is no guarantee that the orifice will not occlude again.

A second drawback of an orifice-plate mesh shunt is the potential for paradoxical embolization. Paradoxical embolization refers to an arterial thromboembolism originating in the venous vasculature (venous thromboembolism or "VTE"), such that an embolus traverses right-to-left through a cardiac shunt into the systemic arterial circulation. The most severe complication of paradoxical embolization occurs when an embolus lodges in the cerebral circulation with resulting cerebral infarction (stroke). Similarly, if a paradoxical embolus enters the coronary arterial circulation, myocardial infarction ("MI") may ensue. Other embolic syndromes result from embolization to the mesenteric, renal, and peripheral arteries supplying the limbs. These may cause, respectively, ischemic bowel syndrome, hematuria with worsening renal function, and gangrene requiring amputation.

Most frequently, VTE in adults is the consequence of in situ thrombosis in the deep veins (deep venous thrombosis or "DVT") of the lower extremities or pelvis. For the most part, clinically relevant venous emboli develop in the popliteal veins or more proximally in larger veins of the upper thigh or pelvis. In patients with DVT involving the popliteal vein, the venous diameter averaged 11.4 mm (range from 6.2 mm to 20.1 mm). Often, emboli are described as having the form of a cast of the vein's lumen with a width equal to the diameter of the vein of origin. These thrombi also tend to be elongated, corresponding to the length of the occluded venous segment.

The risk factors associated with thromboembolic disease include a variety of anatomic, physiological, rheological variables and disease states. Heart failure is a well-recognized risk factor for DVT and VTE, especially in patients with reduced left ventricular systolic function. About 3% of deaths in heart failure patients are due to VTE, usually associated with pulmonary embolism. Patients with transvenous endocardial pacing leads and an intracardiac shunt have a 3-fold increased risk of systemic thromboembolism, suggesting that paradoxical embolism is a contributing underlying cause. There is evidence that the risk of paradoxical embolism is directly related to the orifice size of naturally occurring atrial level shunts such as ASD and patent foramen ovale ("PFO"). The presence of an atrial septal aneurysm is an additional risk factor. For example, as described in the publication "Transcatheter Amplatzer Device Closure of Atrial Septal Defect and Patent Foramen Ovale in Patients with Presumed Paradoxical Embolism" by Khositsth, et al., in a series of 103 adult patients with paradoxical embolization, an ASD was present in 12%, whereas PFO was present in 81%. In patients with clinically significant ASD referred for closure, the incidence of paradoxical embolus has been reported to be up to 14%.

It has been asserted that in order for VTE to enter the systemic circulation, the prevailing LA to RA pressure gradient must be temporarily reduced, eliminated or reversed so that blood will either flow slowly across the shunt, cease to flow across the shunt or flow retrograde across the shunt. Echo/Doppler imaging studies often reveal some amount of shunting in both directions (bi-directional shunting) in patients with congenital ASD, even when LA to RA flow predominates. Bidirectional shunting may be best demonstrated when a subject performs a Valsalva maneuver (straining caused by exhalation against a closed glottis). Valsalva increases intrathoracic pressure, which causes the RA and LA pressures to equalize after several seconds and then for the RA pressure to transiently exceed LA pressure on exhalation. Intermittent bidirectional flow also may be observed at rest when the interatrial pressure gradient is low, or intermittently during the cardiac cycle when LA contraction is delayed compared to RA contraction (interatrial conduction delay). This is seen especially when the atria are enlarged or diseased, such as in heart failure. In this setting, interatrial electrical conduction delay results in retardation of LA contraction. Bidirectional shunting can also be seen transiently during inspiration, when venous return to the RA is increased, during coughing, with abdominal compression, during forced exhalation, or in the presence of severe tricuspid valve regurgitation. Chronically increased pulmonary arterial pressure, as seen in severe pulmonary hypertension, whether primary or secondary to chronic lung disease, recurrent pulmonary embolism, or due to chronic right ventricular volume overload, has been associated with chronic and more severe RA to LA shunting.

Additional phenomena associated with RA to LA shunting are diminished pulmonary blood flow and decreased arterial oxygen saturation due to systemic venous admixing. When these findings are also transient, they are generally well tolerated. Thus, prevention of significant or larger paradoxical emboli is the primary concern rather than preventing reverse shunting per se. As the consequences of paradoxical embolization can be catastrophic, it is desirable, particularly in high-risk patients, that an implantable shunt be equipped with mechanism(s) that limit or minimize the chances of paradoxical embolization or minimize the chances of transporting large emboli.

From these data, it seems reasonable to expect that an orifice-plate mesh shunt, by virtue of its anatomic similarities with congenital secundum ASD, would have a similar risk of paradoxical embolization. It is easily understandable that a thin plate-orifice mesh type of artificial shunt might be more susceptible to paradoxical embolization than other types of shunts with longer orifice geometries, e.g., a nozzle. For any given quanta of RA volume (blood or thrombus), the statistical likelihood of traversing retrograde across the shunt and into the LA would be expected to be a complex function of the duration of pressure gradient reversal, flow patterns in the RA, shunt tunnel distance affecting the length of the flow velocity streamlines, and flow velocity and orifice or lumen size.

A third drawback of an orifice-plate mesh shunt is that percutaneous removal of the shunt is only possible at the time of implantation. Should the shunt become a nidus for infection, develop fatigue or corrosion fractures of its metallic framework, or erode or otherwise impinge on other vital cardiac structures, it cannot be removed by percutaneous retrieval/removal techniques. This is because the shunt, with its large "footprint" on the interatrial septum, is encased in pannus tissue. Attempts at percutaneous removal may result in tearing of the septum, pericardial tamponade, and device embolization into the systemic circulation, resulting in death or the need for emergency surgery. Safe removal would require performing open heart surgery. This entails that the heart be bypassed using an extracorporeal membrane pump oxygenator (cardiopulmonary bypass), so the heart can be opened, the shunt removed, and the septum repaired. Performing such surgical procedures in patients with already established severe heart failure, including its frequently associated co-morbid conditions such as peripheral, cerebrovascular, and coronary artery disease, renal dysfunction, and diabetes, would be expected to have substantial risks for mortality or severe morbidity.

A fourth drawback of an orifice-plate mesh type of shunt is that its geometry renders it relatively inefficient in supporting high flow. For any given pressure gradient across the shunt, an orifice-plate geometry requires a larger orifice because it has a reduced effective orifice size compared with other geometries, such as a venturi-shaped lumen, or a conical shaped nozzle. This is because with an office-plate, there is more energy loss associated with eddy currents at the edges of the plate. Orifice-plate geometries may be categorized as having a relatively low discharge coefficient, which is a dimensionless fluid-mechanical parameter that relates to the relationship between flow and actual orifice size. For practical purposes, the discharge coefficient is the ratio of areas of the exiting jet vena contracta, which is the narrowest portion of the jet, compared to the shunt orifice. For example, the coefficient of discharge for orifice plates placed in pipes tends to be approximately 0.6, but rarely exceeds 0.65. The discharge coefficient is affected by the orifice and chamber dimensions, the pressure gradient, and the viscosity of blood and/or the Reynolds number of the specific flow condition. This differs from the more efficient passage of flow through a classic venturi type of narrowing, where the discharge coefficient usually exceeds 0.9 and is typically in the range of 0.94 to 0.98. The result is that, in comparison with more efficient shunt lumen geometries, an orifice-plate mesh shunt requires a larger orifice diameter to accommodate the same amount of flow for any given pressure differential across the shunt.

A fifth drawback of an orifice-plate mesh shunt is that it occupies a large area or footprint on the interatrial septum. The flanges of the device that anchor the shunt typically occupy the entire area of the fossa ovalis and may overlap adjoining muscular portions of the interatrial septum. These flanges exert persistent pressure on the septum, causing injuring and stimulating an exaggerated healing response as described above. Also, the rigidity of the mesh may interfere with the normal motion of the muscular septum. The flanges additionally may impinge on adjacent cardiac structures such as the roof of the left atrium, the ostia of the pulmonary veins, and the aorta root and sinuses of Valsalva, where due to chronic rubbing contact or sandwiching compressive forces, they may erode into these vital structures. Such erosion has been associated with severe complications including cardiac tamponade and death. For example, the similarly sized Amplatzer ASD disc occlusion device described above has been occasionally associated with erosion into adjoining tissues with resulting catastrophic outcomes.

Additional issues associated with placing relatively large devices with complex three-dimensional geometries are potential difficulties in positioning the shunts accurately in the FO, obtaining sufficient tissue anchoring to prevent migration, and having devices conform to irregularities of the cardiac anatomy. For example, in a report of attempted implantation of orifice-plate mesh shunts in 66 patients in the above cited publication authored by Hasenfuss, et al., device placement was not possible in two patients. And of the 64 implanted patients, the device had to be removed and re-implanted in another 3 patients due to misplacement, migration, or embolization of the first attempted implant.

Finally, the large footprint on the atrial septum may hinder or render impossible performing other interventional procedures that require transseptal access. The large flange diameter and small mesh pore sizes generally make catheter crossing of the atrial septum possible only through the central shunt orifice itself. Transseptal procedures using small diameter catheters, such as atrial fibrillation RF ablation, may be conducted through the orifice-plate lumen only if it is not obstructed by pannus and the orifice location permits entry into all four pulmonary veins. Other structural heart disease procedures that have large diameter delivery systems and/or require crossing the FO in specific locations may encounter difficulties or simply not be possible. These procedures include left atrial appendage occlusion, mitral valve edge-to-edge ("MitraClip") repair, and transvascular mitral valve replacement. For example, placing of a MitraClip optimally requires crossing the FO in its superior-posterior quadrant. The guiding catheter has a tip inner diameter of 7.7 mm (23 Fr). Similar transseptal access is needed to perform reconstructive mitral annuloplasty with the Cardioband device marketed by Valtech. In these cases, the only alternatives might be higher risk therapeutic approaches involving trans-left ventricular apical access or open heart surgery.

The second type of shunt is referred to as a valved unidirectional shunt. These shunts attempt to overcome some of the drawbacks of orifice-plate devices. For example, valved unidirectional shunts have embodiments containing a one-way or check-valve to limit reverse shunting and paradoxical embolization. Some of the valve configurations are designed to open when the LA-RA pressure gradient exceeds a predefined threshold. Other valve configurations close only when the RA pressure exceeds LA pressure (reversed gradient).

U.S. Pat. No. 9,034,034 to Nitzan, the entire contents of which are incorporated by reference herein, solves many of the drawbacks of plate-like orifice mesh shunts describe above. An embodiment of the Nitzan-type shunt comprises an hourglass or diabolo outer shape, having a small FO footprint minimizing septal injury, which is expected to minimize pannus growth and obliteration of the shunt lumen. Its one-way valve also is designed to reduce the potential for reverse shunting and paradoxical embolization. The relatively small footprint of the shunt in contact with the septum and encapsulated collapsible nitinol frame is designed to facilitate percutaneous extraction from the septum and retrieval from the body using a standard goose-neck snare and large-bore sheath, thus making the device more easily retrieved. The venturi tube-like inner lumen of the diabolo shape provides better bulk flow characteristics, permitting a smaller orifice for the same amount of flow compared to orifice-plate shunts. And finally, the small footprint on the FO and the hourglass shape are designed to facilitate accurate placement and retention during implantation. This geometry also minimizes interference with normal motion of the interatrial septum, and the small footprint provides space surrounding the shunt for other potential interventional procedures that require transseptal catheterization.

One embodiment of the Nitzan design, manufactured by V-Wave, Ltd (Caesarea, Israel), designed to support unidirectional left-to-right flow, comprises a self-expanding frame constructed from a laser-cut nitinol tube. The frame includes five sinusoidal circumferential struts interconnected by six longitudinal bars. The frame is heat-set so that it has an asymmetrical hourglass shape or a diabolo shape. The shunt is deployed so that the neck (5.3 mm outer diameter) is placed across the FO and secured in place by its external surface geometry. The shunt's widest portion has a conical shape with an approximately 14.3 mm outer diameter at the LA end of the shunt, which serves as an "entry" port on the distal end of the entry funnel. The entry funnel is deployed in the left atrium, and registers the neck of the shunt to the region of the FO. A second, slightly narrower bell-shaped portion forms the exit portion of the shunt, which expands to a maximum outer diameter of 11.4 mm at the RA end of the shunt. The shunt does not require flanges, discs, or tissue anchors to secure it in place. Septal retention is achieved without applying persistent pressure, tension or rubbing contact on the tissue adjoining the device neck.

The V-Wave shunt has a single inner lumen where flow is entrained into the entry funnel in the LA and passes through the constricted neck having a 5.1 mm inner diameter, which resembles a venturi-type orifice, and then exits through a bioprosthetic valve positioned near the RA end of the shunt. The entry funnel and the central neck region are encapsulated with expanded polytetrafluoroethylene ("ePTFE") to form a skirt or cover over the frame. The skirt is designed to facilitate laminar flow and limit pannus ingrowth during device healing. The exit bell-shaped portion contains three, glutaraldehyde-fixed, porcine pericardial leaflets sutured to the frame at the right atrial extent of the ePTFE encapsulation. The leaflets are designed to create a smooth exit channel and remain in the open position, closing only when the RA pressure exceeds LA pressure by 1-2 mmHg, thus preventing reverse right-to-left shunting.

For deployment, the V-Wave shunt is compressed in a loading tube where it is attached to a triple-latch cable delivery catheter. The loading tube is inserted into a 14F delivery sheath that has been previously placed after a transseptal catheterization from the right femoral vein across the FO. The shunt then is advanced through the sheath until the entry funnel has been deployed in the LA. The entire system is withdrawn as a unit until the LA funnel is in contact with the left side of the FO. The delivery catheter latches are unhooked from the shunt, the delivery catheter withdrawn so the right atrial side of the shunt is held only by its radial force against the delivery sheath. Then the delivery sheath is withdrawn, thereby deploying the exit bell-shaped portion of the shunt on the RA side of the FO. Device placement may be guided and confirmed by fluoroscopy and echocardiography, e.g., intracardiac echo or transesophageal echo.

Pre-clinical testing on the V-Wave shunt was performed in an established juvenile ovine (sheep) model that created an ischemic cardiomyopathy form of heart failure. The sheep were pre-treated with sequential coronary artery microembolization as described in the publication, "Chronic Heart Failure Induced by Multiple Sequential Coronary Microembolization in Sheep" by Schmitto et al. After several weeks, the sheep manifested evidence of severe left ventricular systolic dysfunction and develop elevated LV, LA, and pulmonary artery pressures. In a 12-week survival study, this V-Wave shunt was associated with significant improvements in LA pressure and left ventricular ejection fraction. All manifestations of worsening heart failure were improved and in some cases reversed with interatrial shunting. Concurrent control animals with established heart failure, but were not implanted with the V-Wave shunt, demonstrated progressive worsening of LV ejection fraction, and intracardiac/pulmonary pressure during 3-month follow-up. The physiological improvements in shunted animals were substantial even though the shunt volume was assessed to be small. The pulmonary blood flow/systemic blood flow ratio (Qp/Qs) was between 1.1 to 1.2, as measured by oximetry, which is consistent with a very small shunt. Naturally occurring ASDs, with a Qp/Qs less than 1.5, are generally left untreated as they are well tolerated for decades by the compliant right heart and pulmonary vasculature, without evidence of worsening right ventricular failure despite mild chronic volume overload. This was confirmed in the sheep model where RA and pulmonary artery pressures decreased to baseline levels with shunting, but progressively worsened in the control animals.

A total of 38 patients were implanted with the V-Wave hourglass-shaped shunt having valve leaflets in two similar feasibility studies. The baseline characteristics of the combined study populations are summarized in Table 1 below.

TABLE 1

Baseline characteristics of 38 patients implanted with valved hourglass-shaped shunt device

| | |
|---|---|
| Age, years | 66 ± 9 |
| Male gender, % | 92 |
| Body mass index, kg/m2 | 30 ± 6 |
| NYHA class, median | III (97%), IV (3%) |
| Ischemic Cardiomyopathy, % | 76 |
| DM/HTN/AFIB, % | 68/84/53 |
| ACEi-ARB/BB/MRA/DIUR, % | 78/100/75/94 |
| CRT-D or ICD/CRT-D or CRT-P, % | 74/39 |
| NT-proBNP, pg/ml | 2640 ± 2301 |
| eGFR, mL · min−1 · 1.73 m−2 | 54 ± 20 |
| 6MWT, m | 282 ± 114 |
| PCWP, mmHg | 20 ± 6 |
| RAP, mmHg | 8 ± 4 |
| PAP mean, mmHg | 30 ± 7 |
| CI, L · min−1 · m−2 | 2.1 ± 0.5 |
| PVR, mmHg/L · min−1 | 2.9 ± 1.4 |

TABLE 1-continued

Baseline characteristics of 38 patients implanted with valved hourglass-shaped shunt device

| | |
|---|---|
| LVEF (HFrEF, n = 30), % | 26 ± 7 |
| LVEF (HFpEF, n = 8), % | 50 ± 9 |

NYHA = New York Heart Association heart failure classification;
DM = diabetes mellitus;
HTN = hypertension;
AFIB = atrial fibrillation;
ACEi-ARB = receiving angiotensin converting enzyme inhibitor or angiotensin receptor blocker;
BB = receiving beta blocker;
MRA = receiving mineralocorticoid antagonist;
DIUR = receiving loop diuretic;
CRT-D = implanted with combination cardiac resynchronization therapy pacemaker with ICD;
ICD = implantable cardioverter/defibrillator;
CRT-P = implanted with cardiac resynchronization therapy pacemaker without combination ICD;
NT-proBNP = N-terminal pro b-type natriuretic peptide;
eGFR = estimated glomerular filtration rate;
6MWT = 6 minute walk test distance;
PCWP = pulmonary capillary wedge pressure;
RAP = right atrial pressure;
PAP = pulmonary artery pressure;
CI = cardiac index;
PVR = pulmonary vascular resistance;
LVEF = left ventricular ejection fraction;
HFrEF = heart failure with reduced ejection fraction;
HFpEF = heart failure with preserved ejection fraction.
These parameters and abbreviations are well known to one skilled in the art.

All patients had New York Heart Association ("NYHA") Class III or ambulatory Class IV heart failure symptoms at the time of study enrollment. Patients with either reduced or preserved left ventricular ejection fraction were included. There was a high frequency of co-morbidities known to be associated with a poorer prognosis including coronary artery disease, diabetes mellitus, atrial fibrillation, and chronic kidney dysfunction. All patients received appropriate guideline-driven medical and device therapies prior to study enrollment. Patients had evidence of elevated levels of natriuretic peptides, reduced exercise capacity, elevated intracardiac and pulmonary artery pressures, increased pulmonary vascular resistance, and reduced cardiac output. These factors have also been associated with poor outcomes. Patients were excluded if they had severe right ventricular dysfunction or severe pulmonary hypertension.

Implantation of the V-Wave shunt was successful in all 38 patients and no device replacements were performed. Shunts remained implanted in the atrial septum without dislodgements, migrations or apparent interference with normal septal motion on fluoroscopic or echocardiographic imaging. No shunts have required removal or replacement for infection or strut fracture. Follow-up imaging studies show that there are adjacent locations on the FO, that are available and amenable for performing transseptal procedures to treat other cardiac conditions, including, for example, atrial fibrillation ablation, left atrial appendage occlusion, and mitral valve repair. The valve apparatus, when functioning normally, has been shown to effectively prevent reverse (right-to-left) shunting. Echocardiographic contrast and Doppler studies during rest or Valsalva maneuver show that there is no reverse shunting in the early months after human implantation. Furthermore, no thromboembolic clinical events, including paradoxical embolization, have been observed during the first year of follow-up.

Shunt patency is defined as LA to RA flow through the shunt as observed during transesophageal echo/Doppler study. At 3-months after implantation of the V-Wave shunts, patency was confirmed in all patients. The pulmonary to systemic flow ratio (Qp/Qs), as measured by echocardiography, increased from 1.04±0.22 at baseline to 1.18±0.16 shortly after implantation (p<0.03). In the subgroup of 30 patients with HFrEF presented by Dr. William Abraham, MD at TCT 2016 in Washington D.C., there were statistically significant (p<0.05) improvements in clinician-assessed symptoms, patient assessed quality-of-life scores, and exercise capacity as measured by a 6-minute hall walk testing at 3, 6, and 12 months following implantation There was no deterioration in natriuretic hormone levels, echocardiographic, or hemodynamic parameters. Most importantly, the annualized (Poisson) heart failure hospitalization rate with shunting (0.17 heart failure hospitalization per patient year), was substantially reduced in comparison to a well matched historical control groups (CHAMPION trial Control and Treatment groups, 0.90 and 0.67 heart failure hospitalization per patient year, respectively). These data provide adequate proof-of-concept that interatrial shunting is of benefit to patients with severe symptomatic heart failure. Moreover, these data strongly support moving forward with larger-scale clinical trials including randomized clinical trials.

Notwithstanding the initial success observed in the foregoing trial, device occlusion, e.g., shunts having undetectable LA to RA flow, was observed in some valved interatrial shunt devices after long-term implantation, e.g., by 1 year. Further, shunts may develop bidirectional shunting that was not present early on. Bidirectional shunting is indicative of an incompetent valve, e.g., a valve where one or more leaflets do not fully coapt during closure, resulting in an open channel for reversed flow, and depending on the severity of the incompetence, may create a potential path for paradoxical embolus to traverse from the RA to LA.

To assess the effective orifice size of valved shunts over time, transesophageal echo/Doppler measurements of the diameter of the vena contracta, measured on the left-to-right flow jets through the shunt, were found to be consistent with progressive shunt narrowing. The vena contracta diameter monotonically decreased with time after implantation from 4.0±1.1 mm just after implantation, to 3.6±1.0 mm at 3 months, and 2.7±1.4 mm at 6-12 months (p<0.01). This equates, on average, to shunts losing more than half of their orifice area by 12 months. Moreover, some of the left-to-right jets appeared to be exiting the shunt at an angle substantially different from the long axis of the shunt body. This skewing of the jet is consistent with material inside the shunt such as a valve leaflet with impaired mobility, which diverts the direction of the jet. This observation gives rise to concern about a decrease in the clinical effectiveness of the shunts over time Clinical effectiveness also may be measured by the rate of hospitalization for worsening heart failure. In the 38 patients, during the first 6 months after implantation of the V-Wave shunt, the hospitalization rate was 0.16 per patient year, which increased to 0.40 per patient year between months 6-12. These data suggest there may be a loss of shunting benefit consistent with the time course associated with shunt narrowing or occlusion.

There are several possible mechanisms working alone or in combination that could explain these observations.

The least likely cause of shunt occlusion is collapse of the shunt due to external forces applied by the septum. For example, it is possible that contraction of pannus tissue formed during the later stages of healing (remodeling) could result in extrinsic compression of the shunt. However, there is no evidence to support this scenario based on multiple observations of frame geometry seen during pre-clinical studies and during follow-up transesophageal echocardiography ("TEE"), CT, or fluoroscopic imaging in humans. In all cases, the observed shunt frame has not been observed to be extrinsically compressed or in any other way narrowed, deformed, or fractured.

Another possible mechanism is in situ thrombosis of the shunt. However, all patients were treated with monitored anticoagulation for the first three months, or indefinitely if there were other indications for chronic anticoagulation, which was most commonly required in patients with a history of atrial fibrillation. Subjects were also treated simultaneously with low-dose aspirin, which was continued indefinitely. Having experience with prosthetic cardiac valves as a predicate, valve thrombosis would have been expected to be seen earlier, typically within 30-45 days after implantation, especially in patients with a history of subtherapeutic anticoagulation therapy.

In the 38 patients implanted with the V-Wave valved hourglass-shaped shunt described above, no thrombi were detected on 121 consecutive post-implantation echocardiograms. These studies systematically looked for intracardiac or device thrombus by an independent Echocardiographic Core Laboratory at time points including one day after implantation, and at 1, 3, 6, and 12 months after implantation. None of the patients presented with stroke or other clinical manifestations of thromboembolic events. Of 9 patients with suspected shunt occlusion or incompetent valves, most were taking therapeutic doses of anticoagulants (warfarin or New Oral Anticoagulant agents) at the time the shunt anomaly was discovered. Another reason that thrombosis is unlikely is the observation of progressive vena contracta narrowing over a time course of 6 months or more. Thrombosis would be expected to result in sudden lumen loss, and not progress slowly over a period of months.

A third potential cause of occlusion is neoendocardial tissue overgrowth or pannus formation that narrows the lumen at the neck of the hourglass-shaped shunt. Applicants' earlier ovine studies suggest otherwise. Specifically, the shunt lumen surface at the neck of the hourglass contained only microscopic amounts of cellular material. On gross pathological examination, there was no visible loss of the lumen area in neck region. A human shunt specimen has been examined in an explanted heart from a patient that underwent cardiac transplantation 2.5 years after shunt implantation. The ePTFE surfaces of the shunt including the lumen at the neck contained no pannus formation or narrowing of any kind.

In another example, a left atrial pressure sensor implanted across the FO by transseptal catheterization and used for guiding the medical therapeutic dosing in symptomatic patients with severe heart failure was observed to experience pannus formation. In the original embodiment of the sensor, the sensing diaphragm, located at the distal end of the sensor module body, protruded into the left atrium by 1-mm beyond its three anchoring legs that rested on the left atrial side of the septum. In a later, improved geometry version, the legs were placed more proximal on the sensor module body so that sensing diaphragm protruded into the LA by an additional 1.5 mm.

In a comparative inter-species pathology study, neoendocardial tissue (pannus) formation was observed over the sensing diaphragm in 20 of 31 original sensors compared with only 3 of 40 specimens with the improved geometry sensor. Of the 20 original sensors with tissue coverage, 7 had demonstrable artifacts in the LA pressure waveform. In each case with artifacts, pannus formation over the sensing diaphragm had a thickness >0.3 mm. These data indicate that when tissue coverage exceeds this thickness, the tissue interferes with fluid pressure measurement. None of the improved sensors had waveform artifacts or tissue thickness >0.3 mm.

In addition to producing waveform artifacts, the time course of tissue encapsulation of the sensing diaphragm could be estimated by assessing LA pressure waveforms for baseline drift with or without the development of artifacts. It was hypothesized that as neoendocardial tissue grows over the sensing diaphragm, measured LA pressure increased due to a drifting baseline caused by tension applied from the tissue capsule covering the diaphragm through its contiguous connection with the atrial wall. This healing phenomenon may be initiated as early as several weeks' post implant in animals and starts around 3-4 months in humans. Using the timing of drift to indicate tissue coverage in humans, it was shown that in a group of 46 heart failure patients with the original sensor design geometry, about 25% developed the characteristic drift pattern associated with tissue coverage of the sensing diaphragm during the first year after implantation. Of 41 similar patients implanted with the improved geometry sensor, none developed drift.

Pannus formation on devices that traverse the interatrial septum has been observed to start at the portions of the device in contact with the septum in the region of local tissue injury. Tissue growth progresses contiguously, extending translationally along the external surfaces of the device that protrude into each atrial chamber. This pannus growth thins as a function of distance from the sites of cardiac contact until it becomes essentially a monolayer of neoendothelial cells. The process naturally stops after about 6-12 months in humans. Thereafter, the remaining tissue may remodel but active growth of pannus is completed. From these data, Applicants observed that tissue coverage typically grows a distance of about 3 mm from its starting place on the septal wall before stopping or becoming thin enough so as not to impede device function.

Thus, for pannus to cause narrowing of the lumen at the shunt neck, it would have to extend contiguously from the site of injury on the septum for some distance to reach the neck. Applicants have determined that translational tissue growth over a distance of 3 or more millimeters becomes much less likely.

Pannus formation affecting the valve leaflets is the most likely stand-alone mechanism that explains all of the untoward observations seen in human subjects implanted with V-Wave shunts, including progressive shunt narrowing, incompetence of the valve with bidirectional flow, and eventual loss of shunt flow with associated loss of clinical efficacy.

Tissue overgrowth affecting the valve leaflet bases and commissures was the predominant histopathological finding in the ovine pre-clinical study described above. Gross pathological examination of shunts implanted for 3 months showed pannus infiltration extending from the adjacent FO into the valve leaflet bases with thickening of the leaflet bodies in 5 out of 6 shunts. In 4 shunts, there was fusion of at least 2 of the 3 valve commissures where the leaflet edges were sutured to the shunt frame. Fusion of all 3 commissures was observed in 3 shunts. One case showed severe narrowing at the commissures with a luminal area of 4 $mm^2$ or a 75% area stenosis in comparison to the normal 19.6 $mm^2$ lumen at the device neck. The leaflets were described as semi-pliable or stiffened in 4 out of 6 shunts. In two of the devices, commissural fusion and leaflet thickening were so pronounced that complete leaflet coaptation could not likely occur during valve closure. In none of these cases has pannus formation been seen to narrow the shunt neck.

On examination of microscopic sections, pannus thickness tends to be greater on the side of the leaflets facing the atrial septum where the ePTFE/leaflet junction was infiltrated with pannus that was contiguous with the adjoining atrial tissue. Pannus extended from the atrial septum on and around the right atrial edge of the ePTFE skirt and into the base and commissures of the valve leaflets. At 3 months, the pericardial leaflets showed varying degrees of pannus coverage ranging from mild to marked. In general, pannus is thickest at the leaflet bases and commissures, and tapers toward the free edges. In 2 sheep, the pannus on the leaflets measured 2 to 3 times the original thickness of the leaflets.

The pannus was generally well healed or organized by 3 months. It was composed of collagen and proteoglycan matrix surrounding smooth muscle cells, fibroblasts and rare focal areas of inflammation with lymphocytes, macrophages, and occasional multinucleated (foreign body type) giant cells. The pannus tissue was mostly covered with neoendothelium consistent with near complete healing. No leaflet calcification or thrombi were observed.

Although animal models of cardiovascular devices are limited in their ability to represent human tissue healing responses, the major differences are characteristically limited to the temporal duration of the response. For example, in a comparative pathology study described in the publication, "Comparative Pathology of an Implantable Left Atrial Pressure Sensor" by Roberts, et al., of a percutaneously implantable titanium/nitinol-enclosed LA pressure sensor, implanted on the interatrial septum, it was found that sheep at 1.5 to 8 months and canines implanted for 1 to 25 months, closely approximated the pathological findings seen in humans implants of 3 to 56 months duration. Histology had a similar appearance in humans and animals, and confirmed that the tissue covering the device was composed of a neoendocardium lined with a neoendothelium. The appearance of the neoendocardial tissue covering the sensor described above was similar to what is observed with ASD closure devices.

This mechanism of pannus formation preferentially affecting the bioprosthetic valve material compared to the ePTFE encapsulated portions of the shunt was observed in the human explanted specimen referred to earlier. After 2.5 year of implantation in heart, the 3 pericardial leaflets were severely thickened, immobile, infiltrated at their bases and commissures with pannus resulting in valvular stenosis with a reduction in outflow area of 52% relative to the non-obstructed shunt neck. Although this shunt was patent, it would have been incompetent, allowing bidirectional flow, and would have shunted less than half of the flow expected for any given pressure gradient.

To further evaluate the tendency of this bioprosthetic valve to become infiltrated with pannus, valved and valveless designs of the V-Wave shunt were implanted by applicants in a non-diseased juvenile ovine (n=9) model. Specifically, this study was designed to highlight the resistance of a valveless, ePTFE encapsulated shunt (n=6) to pannus formation, narrowing and occlusion, relative to the legacy valved version previously used in humans (n=3), by creating a highly proliferative model expected in healthy juvenile sheep where the left-to-right interatrial pressure gradient was expected to be small. In the valveless design, the bioprosthetic valve material and its attaching polypropylene suture were removed and the ePTFE encapsulation was extended to cover the entire nitinol frame of the shunt except for the last 1.5 mm on the RA side where the shunt was coupled to its delivery system for deployment. The ePTFE used had an internodal distance of up to 30 microns. At 12 weeks the sheep where euthanized. The gross pathology findings showed that the 3 valved shunts were heavily infiltrated with pannus formation, extending from the septum into the regions containing the bioprosthetic leaflets. The leaflets were fused, immobile and highly stenotic leaving only a pinhole opening. The degree of pannus formation was much exaggeration versus prior experience in the ovine heart failure model. Thick pannus extended retrograde contiguously from the leaflet bases toward the hourglass neck of the shunts. The pannus growth from the original septal site of injury to the tips of the valve leaflets exceeded 3 mm in distance. Pannus appeared to grow through the valve commissures and through the suture holes attaching the porcine pericardial leaflets to the frame and the ePTFE skirt. Pannus formation was associated with mononuclear inflammatory cell infiltrates and multinucleated giant cells.

All 6 of the valveless, ePTFE encapsulated shunts were widely patent with only minimal pannus formation attaching the FO tissue to the external surface of the device. Applicants observed no pannus growing translationally more than 3 mm along the external surface of the ePTFE from the septum. No visible pannus reached from the septum all the way into the lumen portion of either the left atrial entry cone or right atrial exit cone of the device. The lumina at the necks of all of the shunts were widely patent on gross and microscopic examination. There was no evidence of pannus formation permeating through the ePTFE encapsulation into the shunt lumen.

From these combined observations, applicants have determined that length of translational pannus growth from the site of healing may be dependent on the type of biomaterial surface. In the case of the ePTFE encapsulated shunt, pannus formation severe enough to interfere with device function tends to translate a maximum of about 3 mm from the site of injury, whereas in the case of the bioprosthetic valve material tested, the amount of pannus formation and translational length of pannus tissue growth were exaggerated.

Also, from these data, it is reasonable to expect that the near complete shunt healing seen after 3 months in the juvenile ovine model will be predictive of the histopathological findings in humans at 9-12 months. Moreover, these gross and microscopic observations, with their anticipated species-to-species conservation of findings, leads to the conclusion that the healing response in sheep is likely indicative of the mechanism causing shunt closure, valvular incompetence, and progressive stenosis in humans. Thus, there exists a need for a more durable shunt configuration that maintains luminal patency for extended periods of time.

It further would be desirable to provide a shunt for redistributing atrial blood volumes and reducing interatrial pressure imbalances that reduces the risk of paradoxical embolism caused by emboli transfer from the right to left atria.

It also would be desirable to provide an interatrial shunt configuration that reduces the risk of pannus formation after a prolonged period of implantation, where the degree of pannus formation and tissue ingrowth is not strongly dependent on the manner or location in which the shunt is implanted in the FO.

SUMMARY OF THE INVENTION

In view of the foregoing drawbacks of previously-known interatrial shunts, an asymmetric shunt constructed in accordance with the principles of the present invention provides a more durable configuration that maintains luminal patency for extended periods of time. The inventive asymmetric shunts further enable redistribution of interatrial blood volumes and pressure imbalances while reducing a risk of paradoxical embolism caused by emboli moving through the shunt from the right to left atria.

The asymmetric device for regulating blood volume distribution across a patient's atrial septum includes a first expandable end region transitionable from a contracted delivery state to an expanded deployed state in which the first expandable end region extends into the patient's left atrium and an inlet end of the first expandable end region is in a first plane, and a second expandable end region transitionable from a contracted delivery state to an expanded deployed state in which the second expandable end region extends into the patient's right atrium and an outlet end of the second expandable end region is in a second plane. The first plane intersects the second plane, e.g., at an angle between 20 and 45 degrees. In addition, the asymmetric device includes a neck region joining the first expandable end region to the second expandable end region, the neck region sized and shaped for placement in the patient's atrial septum. The asymmetric device may be formed of a plurality of longitudinal struts interconnected by a plurality of circumferential sinusoidal struts.

In accordance with one aspect of the present invention, the inlet end of the first expandable end region has a first cross-sectional shape, e.g., a circle, and the outlet end of the second expandable end region has a second cross-sectional shape different from the first cross-sectional shape of the inlet end of the first expandable end region, e.g., a cross-sectional shape having a first pair of opposing sides that extend parallel and a second pair of opposing ends that curve, in the expanded state. In addition, the asymmetric device has a central longitudinal axis. From a first profile of the device having a first orientation, the central longitudinal axis has a curved shape. In accordance with another aspect of the present invention, the central longitudinal axis of the device lies in a single plane.

In addition, the asymmetric device may include a conduit having a lumen wall defining a lumen, wherein the lumen wall is resistant to transmural and translational tissue growth. For example, the lumen may have a diameter in the neck region in a range of 5 mm to 6.5 mm, and may provide high velocity flow therethrough, while limiting paradoxical emboli passing across the lumen during a transient pressure gradient reversal. The conduit may include a layer of biocompatible material. The conduit may have a first end that extends from the neck region a first distance of at least 3 mm into the patient's left atrium and a second end that extends from the neck region a second distance of at least 3 mm into the patient's right atrium, thereby preventing pannus formation from narrowing the lumen of the conduit in the neck region. The second end of the conduit may extend from the neck region a distance of between 3 mm to 15 mm into the patient's right atrium.

Further, the conduit may be sized and shaped so that when implanted the second end of the conduit is located out of a natural circulation flow path of blood entering into the patient's right atrium from an inferior vena cava, thereby reducing a risk of emboli entrained in flow from the inferior vena cava being directed into the second end of the conduit. In addition, the first expandable end region of the asymmetric device, in the expanded deployed state, may form a filter that prevents emboli from entering the second end of the conduit.

In accordance with another aspect of the present invention, the asymmetric device for regulating blood volume distribution across a patient's atrial septum includes a first expandable end region transitionable from a contracted delivery state to an expanded deployed state in which the first expandable end region extends into the patient's left atrium and an inlet end of the first expandable end region has a circular cross-sectional shape in the expanded state, and a second expandable end region transitionable from a contracted delivery state to an expanded deployed state in which the second expandable end region extends into the patient's right atrium and an outlet end of the second expandable end region has a cross-sectional shape in the expanded state having a first pair of opposing sides that extend parallel and a second pair of opposing ends that curve. The asymmetric device may have a central longitudinal axis, wherein from a first profile of the device having a first orientation, the central longitudinal axis is a straight line; whereas, from a second profile of the device having a second orientation, the central longitudinal axis has a curved shape. For example, at the second orientation of the second profile of the device, one of the first pair of opposing sides that extend parallel of the cross-sectional shape of the second expandable end region in the expanded state is closest to the first expandable end region.

DETAILED DESCRIPTION OF THE PREFERRED EMBODIMENTS

Interatrial shunts are provided for redistributing interatrial blood volumes and reducing left atrial pressure, which may be advantageous in treating subjects suffering from heart failure ("HF") or other disorders associated with elevated left atrial pressure. A preferred embodiment of the inventive device includes an anchor, which may be an hourglass or "diabolo" shaped stent or frame, and a conduit, formed by encapsulating the frame in a synthetic biocompatible material. The shunt is configured to be lodged securely within a passage formed in the atrial septum, preferably the fossa ovalis, and provides one-way blood flow from the left atrium to the right atrium, when blood pressure in the left atrium exceeds that on the right.

Figure 1A:
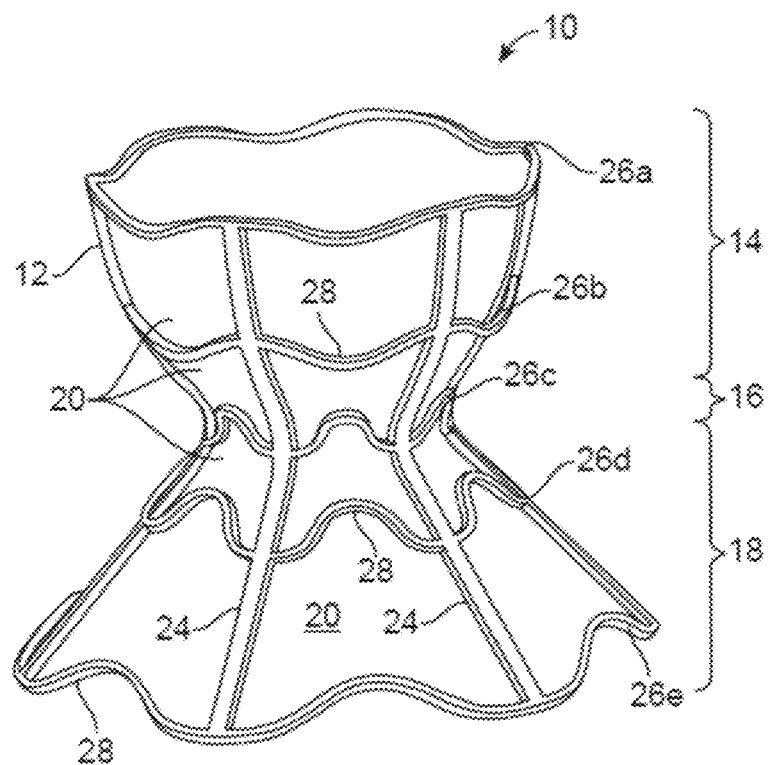
FIGS. 1A to 1C are, respectively, perspective, end and side views of an interatrial shunt.
Figure 1B:
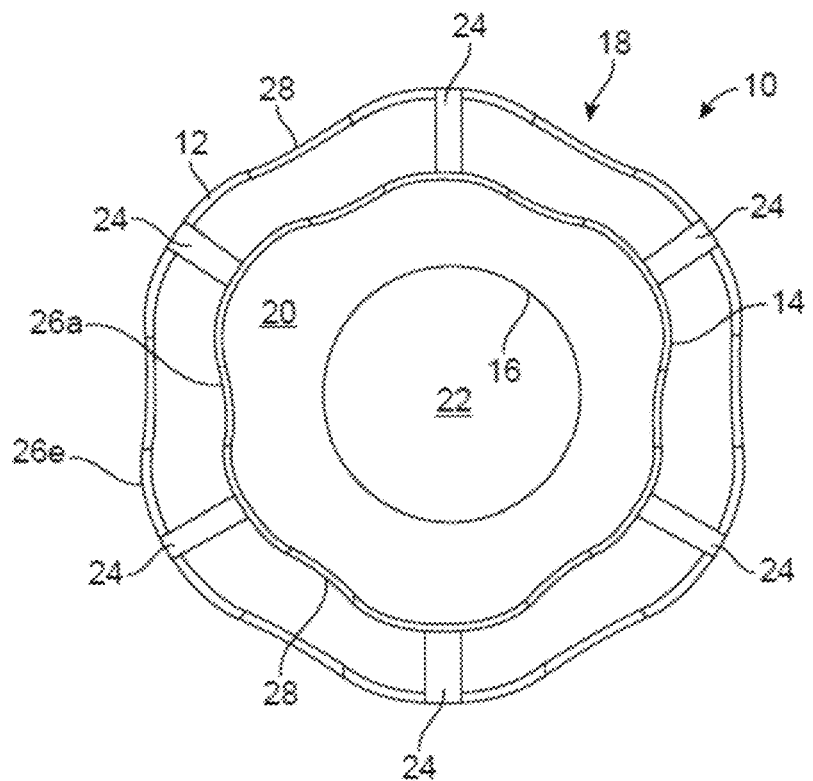
Figure 1C:
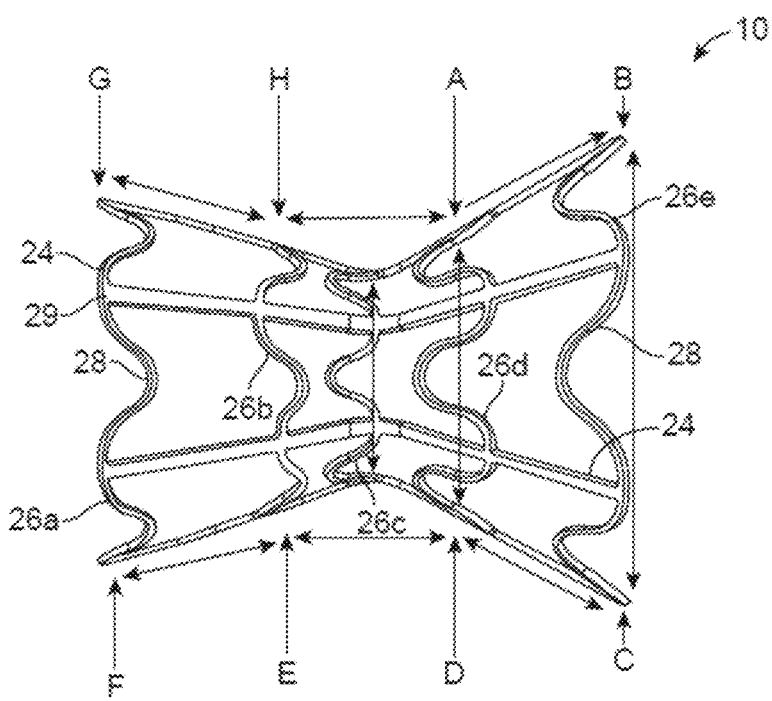

Referring now to FIGS. 1A to 1C, an illustrative embodiment of an interatrial shunt is described. Shunt 10 may be constructed similar to the shunt designs disclosed in U.S. Pat. No. 10,076,403, assigned to the assignee of the instant application, the entire contents of which are incorporated by reference herein. For example, shunt 10 includes anchor 12 having three regions: flared or funnel-shaped end region 14, flared or funnel-shaped end region 18, and neck region 16 disposed between end regions 14 and 18. Neck region 16 is configured to lodge in a puncture formed in the atrial septum, preferably in the fossa ovalis. Flared end regions 14 and 18 are configured to partially engage and protrude beyond the right and left sides, respectively, of the atrial septum when implanted. Shunt 10 further comprises a conduit, illustratively formed by encapsulating anchor 12 with biocompatible material 20 that covers all or substantially all of anchor 12 to form a conduit defining a lumen or interior passageway 22.

Flared region 14 is configured to be disposed in the right atrium, while flared region 18 is configured to be disposed in the left atrium. In one embodiment, anchor 12 includes six longitudinal struts 24 interconnected by five circumferential struts 26a-26e. As depicted in the figures, a conduit is formed by biocompatible material 20 that encapsulates the entirety of neck 16, flared end region 18, and flared end region 14. Biocompatible material 20 preferably is affixed to anchor 12 using a suitable biocompatible adhesive or by sandwiching the anchor between inner and outer layers of biocompatible material using sintering techniques.

The radial dimensions, axial lengths and contours of neck region 16 and flared end regions 14 and 18 preferably are selected to provide laminar flow through the interior of the shunt, to reduce the formation of eddy currents when implanted, and thus inhibit thrombus formation; to inhibit pannus formation that could obstruct the neck region; to promote tissue ingrowth around the exterior of the neck region to secure the shunt against migration; to provide a desired rate of blood flow between the left and right atria at physiological pressure differentials; and to prevent retrograde paradoxical embolization.

As noted above, neck 16 of shunt 10 preferably is configured for implantation through the fossa ovalis of the atrial septum, and more preferably near or at the central portion of the fossa ovalis. As known to those skilled in the art, the fossa ovalis is a thinned portion of the atrial septum formed during fetal development of the heart, which appears as an indent in the right side of the atrial septum and is surrounded by a thicker portion of the atrial septum. While the atrial septum itself may be several millimeters thick and muscular, the fossa ovalis may be only approximately one millimeter thick, and is formed primarily of fibrous tissue.

Shunt 10 may be asymmetrically shaped to take advantage of the natural features of the atrial septum near the fossa ovalis, and to provide suitable flow characteristics. For example, the anchor may have an hourglass or diabolo shape where a LA entry funnel resembles a conical-shaped nozzle and a RA exit funnel is "bell" shaped, with the wide mouth lumen of the bell at the RA exit port in the RA. The narrow entrance to the bell-shaped exit funnel connected to the orifice of the neck region may be configured to approximate the curved surface of a parabola. This type of convergent-divergent nozzle resembles the shape of a classical de Laval nozzle used in rocket engines. Left to right flow is largely governed by the smooth convergence of streamlines in the entry cone and the divergence of streamlines exiting the bell. Such a nozzle configuration is very efficient in the forward flow direction having a discharge coefficient resembling a classic venturi tube, e.g., 0.95-0.98.

Referring now to FIG. 1C, points B and C are located on the leftmost circumferential strut 26e, which defines the LA entry port. Points A and D are located on circumferential strut 26d along the LA entry funnel proximal to strut 26e. Points H and E are located on circumferential strut 26b along the RA exit funnel, and points G and F are located on circumferential strut 26a, which defines the RA exit port. In preferred embodiments, the diameter of lumen 22 in the neck region of the shunt orifice ranges from 5 to 6.5 mm. The portion of the shunt crossing the FO, bounded by points ADEH may be 3 mm in axial length but may be extended up to 10 mm in patients with a thicker FO. The diagonal length between points AB, CD, EF, and/or GH is preferably ≥3 mm so that pannus cannot grow translationally inward from the ends of the shunt and thus obstruct neck region 16. In addition, the horizontal component length between points AB, CD, EF, and/or GH is preferably ≤15 mm, to avoid interference with existing cardiac structures when implanted. It has been determined that providing a length of segments EF and GH generally greater than 5 mm is expected to ensure that the end region that extends into the right atrium is disposed generally out of the flow path of blood returning from the inferior vena cava, which is most likely to have entrained emboli that could cause paradoxical embolization. Truncated funnel cones bounded by ABCD and/or EFGH may have volumes ≤2 ml.

Other embodiments of the shunt may include anchors with different combinations and configurations of circumferential ring and axial strut elements. Specifically, such embodiments, may have more or less than 6 longitudinal struts 24 and more or less than five circumferential struts 26a-26e. These configurations may yield other shunt lumen geometries. In another embodiment, anchor 12 may be made of a self-expanding polymer. Alternatively, the anchor need not be self-expanding, and may be made from a plastically deformable biocompatible metal such as 316L stainless steel, cobalt chromium alloys, or any other such suitable materials known to those skilled in the art. Such a deformable shunt anchor may be delivered by an expanding member, such as a balloon, that is configured to achieve the desired luminal geometry. The deformable anchor may be designed to expand prismatically or at certain localized sites where ductile hinges are configured for more selected expansion as taught by U.S. Pat. No. 6,242,762 to Shanley, the entire contents of which are incorporated by reference herein.

Figure 2:
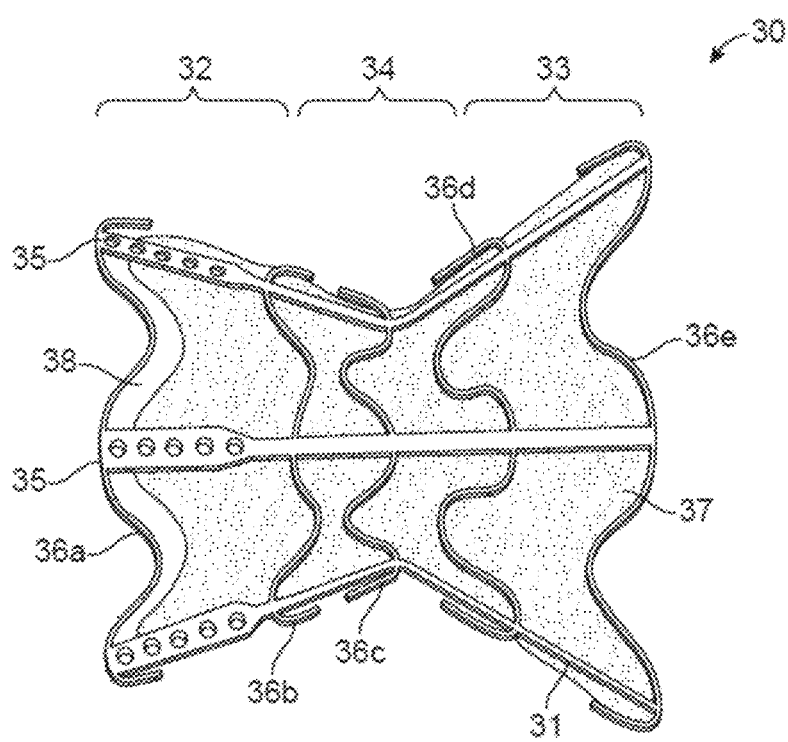
FIG. 2 is a side view of an alternative embodiment of an interatrial shunt having a cutout in its polymeric encapsulation to secure the shunt to a delivery system.

Referring now to FIG. 2, an alternative embodiment of an interatrial shunt is described. Shunt 30 includes anchor 31 is similar in construction to that described for the embodiment of FIGS. 1A-1C, and has flared end regions 32 and 33 and neck region 34. When implanted in a patient's interatrial septum, flared end region 32 is disposed in the patient's right atrium, while flared end region 33 is disposed in the patient's left atrium, with neck region 34 situated in a passage formed in the interatrial septum. Anchor 31 includes longitudinal struts 35 and circumferential struts 36a-36e, and is encapsulated by biocompatible material 37. Anchor 31 may comprise a self-expanding or plastically deformable material as described herein above.

Shunt 30 of FIG. 2 differs from the previous embodiment in that biocompatible material 37, for example ePTFE, includes cutout 38 adjacent to circumferential strut 36a. Cutout 38 may extend proximally from circumferential strut 36a for a distance of 0.5 mm to 2 mm, and more preferably about 1 mm, to permit circumferential strut 36e to be releasably engaged with a delivery system during deployment, for example, hooks, as described in U.S. Pat. No. 9,713,696 to Yacoby, the entire contents of which are incorporated by reference herein. Biocompatible material 37 may be trimmed manually or mechanically from circumferential strut 36a to create cutout 38 or by laser-cutting. In this manner, shunt 30 may be positioned and repositioned in a passage formed in the interatrial septum until the clinician is satisfied with the device placement, before being released. In a preferred embodiment, the conduit formed by biocompatible material 37 extends a distance of at least 3 mm beyond neck region 34 into flared end region 32, to ensure that pannus cannot grow translationally along luminal wall far enough to partially occlude the flow area of neck region 34. Additionally, flared end region 32 extends a distance of at least 5 mm into the right atrium when implanted in the interatrial septum to ensure that the entry of flared end region 34 is generally not aligned with flow paths generated by blood entering the right atrium from the inferior vena cava, thereby reducing the risk that emboli carried from the lower extremities into the right atrium will cause paradoxical embolism by passing through shunt 30.

The interatrial hourglass-shaped shunt with flow characteristics resembling a venturi tube and a discharge coefficient of approximately 0.96-0.97 may have a minimal neck orifice inner diameter ranging from 5 mm to approximately 6.5 mm. Having a somewhat larger orifice diameter, within this range, e.g. 6.0 mm, will support approximately 35% more flow for any given pressure gradient compared with a 5.1 mm shunt. This may not only create improved hemodynamic conditions but provide additional benefit in maintaining shunt flow should some shunt narrowing due to pannus ingrowth occur during device healing.

In addition, various nozzle geometries with high discharge coefficients relative to an orifice-plate geometry advantageously may be used to provide laminar flow through the shunt. These include but are not limited to various variations of venturi tubes, conical convergent nozzles (with convergence angles from 20 to 80 degrees), cylindrical convergent nozzles, and the Addy type nozzle with a convergent curved entrance wall leading to a length of cylindrical tubing having a diameter equivalent to the orifice diameter. The latter two appear similar in appearance to the horn of a trumpet. In another preferred embodiment, the shunt lumen may be a cylindrical tube with no or minimal dilation at the entry or exit ports.

The cross-section of lumen 22 (see FIG. 1B) need not be circular and/or the lumen need not be coaxial with a straight horizontal line axis when viewed longitudinally. Although these latter geometries may be difficult to deliver through catheters with circular luminal cross-sections, they may be constrained to such catheter lumens and expand into non-circular cross-sectional or curved longitudinal geometries upon deployment. Other preferred embodiments include any combination of entry, orifice, and exit geometries where the exiting jet vena contracta cross-sectional area is 70% or greater compared with the minimal orifice area, over the range of physiological interatrial pressure gradients, thereby having a higher discharge coefficient than an orifice-plate.

A shunt with a single LA conical entry funnel, with an hourglass-shaped lumen, or with a tubular lumen, having a discharge coefficient of 0.70 or larger, generally has a longer tunnel of entrained flow by nature of its longer length, typically 6 to 30 mm long, versus an orifice-plate mesh type shunt, which may be defined by the thickness of the FO itself and is typically shorter than 6 mm, e.g., 3 mm or less. For paradoxical embolization to occur, i.e., for a paradoxical embolus to embolize from the heart into the systemic arterial circulation, the paradoxical embolus must pass completely or nearly completely through the shunt. Emboli may be propagated by their residual kinetic energy against a left-to right gradient or when there is no gradient, or may be carried along when a reversed pressure gradient creates right to left bulk flow. Depending on the relative magnitude of the kinetic energy of the embolus and the bulk flow directional status, a longer lumen shunt will tend to pass fewer emboli compared to an orifice-plate shunt with a shorter lumen. This is likely to be the case in the presence of normal left to right bulk flow or when there is zero net flow. This is also likely to be true during very transient pressure gradient reversals, such as during a cough. Therefore, in another preferred embodiment, a shunt with a flow lumen length of 6 to 30 mm, or more typically 10 to 15 mm, by virtue of its increased lumen length, will have less tendency for paradoxical embolization than an orifice-plate mesh shunt.

Figure 3A:
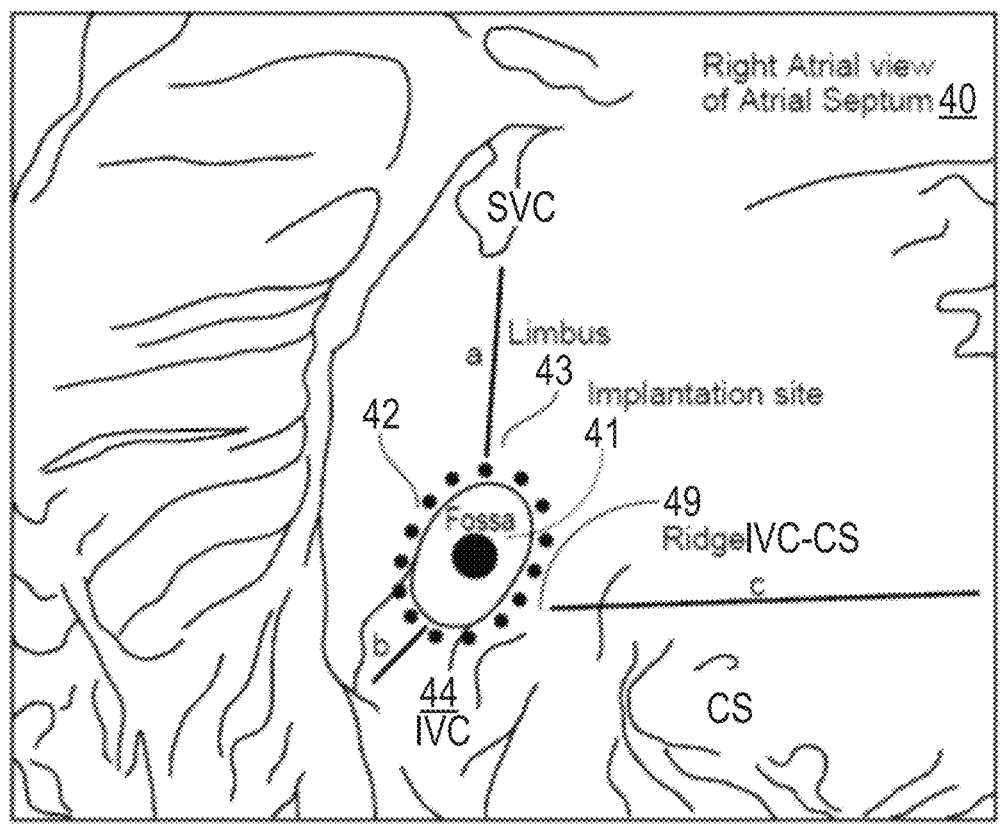
FIGS. 3A and 3B are, respectively, a plan view of the right atrial side of the atrial septum, illustrating implantation of a shunt through a portion of the fossa ovalis, and a perspective view of an embodiment of the shunt of FIGS. 1A-1C positioned in the fossa ovalis of the atrial septum.
Figure 3B:
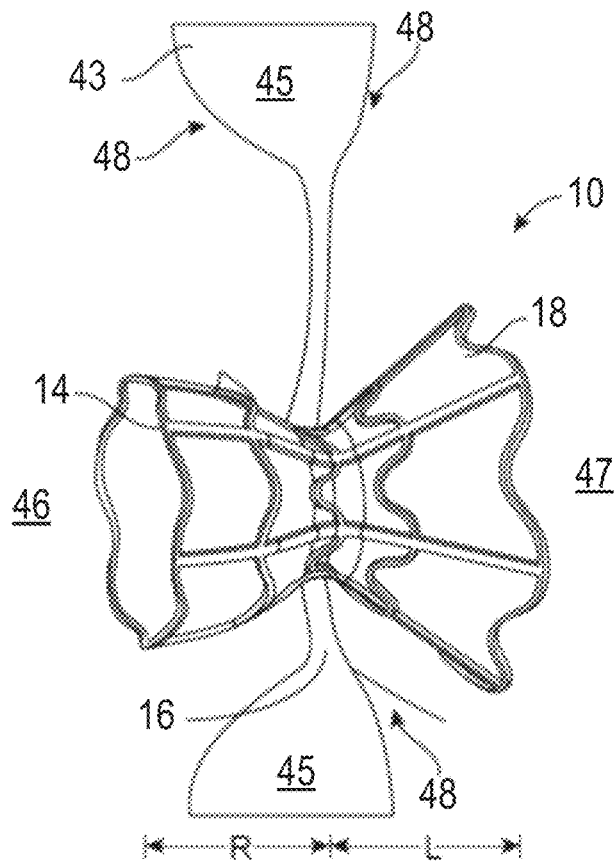

Referring now to FIG. 3A, a preferred location for implanting shunt 10 of FIGS. 1A-1C is described. FIG. 3A is a plan view of the right atrial side of atrial septum 40, including implantation site 41 located at a central position of fossa ovalis 42. Preferably, implantation site 41 is selected so that the shunt may be implanted spaced apart from the surrounding limbus 43, inferior vena cava ("IVC") 44, and atrial septum 45. For example, as shown in FIG. 3B, flared end region 14 is configured to be implanted in right atrium 46 and may be tapered so as to have a more cylindrical shape than does flared end region 18, which is configured to be implanted in left atrium 47. The more cylindrical shape of flared end region 14 may reduce or inhibit contact between flared end region 14 and limbus 43 of fossa ovalis 42, that is, between flared end region 14 and the prominent margin of the fossa ovalis, while still anchoring device 10 across atrial septum 45. The more cylindrical shape of flared end region 14 further may reduce or inhibit contact between flared end region 14, and the right side of atrial septum 40, as well as ridge 49 separating the coronary sinus from the IVC 44 (shown in FIG. 3A but not FIG. 3B).

Still with respect to FIG. 3A, a preferred location for shunt implantation may be slightly anterior to the centerline of the long axis of the fossa ovalis, i.e., located on the right hand side of the ovale. This location leaves potential space in the upper left quadrant (posterior-superior) of the fossa, which has been found to be optimal for crossing the fossa to perform structural heart disease procedures on the mitral valve, including edge-to-edge repair with MitraClip® transcatheter mitral valve repair system offered by Abbott, Abbott Park, Ill. and mitral annuloplasty with Cardioband, offered by Valtech Cardio, Or Yehuda, Israel. This preferred location also leaves potential space in the lower left quadrant (posterior-inferior) of the fossa, which has been found to be optimal for crossing the fossa to perform structural heart disease procedures to occlude the left atrial appendage. A shunt with an hourglass shape that occupies the smallest possible location on the fossa, as described herein, facilitates these other procedures.

Again, referring to FIG. 3B, shunt 10 preferably is configured so as to avoid imposing significant mechanical forces on atrial septum 45, thus allowing the septum to naturally deform as the heart beats. For example, the thicknesses of muscular areas of septum 45 may change by over 20% between systole and diastole. It is believed that any significant mechanical constraints on the motion of atrial septum 45 in such areas would lead to the development of relatively large forces acting on the septum and/or on atrial tissue that contacts shunt 10. Such forces could invoke an inflammatory response and/or hyperplasia in the atrial septum tissue, and possibly cause shunt 10 to eventually lose patency. However, by configuring shunt 10 so that neck region 16 may be implanted entirely or predominantly in the fibrous tissue of the fossa ovalis 42 with a small footprint, the hourglass shape of shunt 10 is expected to be sufficiently stable so as to be retained in the septum, while reducing mechanical loads on the surrounding atrial septum 45. Tissue ingrowth from atrial septum 45 in regions 48 may further enhance binding of shunt 10 to the septum. Preferably, there should be a substantial rim of fossa around the shunt after implantation, e.g., for a thickness of 1-2 mm, as depicted in FIG. 3B.

Also, because neck region 16 of shunt 10 is significantly narrower than flared end regions 14 and 18, shunt 10 will "self-locate" in a puncture through atrial septum 45, particularly when implanted through the fossa ovalis, with a tendency to assume an orientation where its longitudinal axis is substantially orthogonal to the FO. In some embodiments, neck region 16 may have a diameter suitable for implantation in the fossa ovalis, e.g., that is smaller than the fossa ovalis, and that also is selected to inhibit blood flow rates exceeding a predetermined threshold. Neck region 16 preferably provides a passage having a diameter between about 4 and about 7 mm, and more preferably between about 5 mm and about 6.5 mm. For example, diameters of less than about 4 mm may in some circumstances not allow sufficient blood flow through the shunt to decompress the left atrium, and may reduce long-term patency of the shunt. Conversely, diameters of greater than about 7 mm may allow too much blood flow, resulting in right ventricular volume overload and pulmonary hypertension. Preferably, the effective diameter at the narrowest point in shunt 10 is about 5 mm to 6.5 mm.

The diameters of flared end regions 14 and 18 further may be selected to stabilize shunt 10 in the puncture through atrial septum 45, e.g., in the puncture through fossa ovalis 42. For example, flared end region 18 may have a diameter of 10 to 20 mm at its widest point, e.g., about 13 to 15 mm; and flared end region 14 may have a diameter of 9 to 15 mm at its widest point, e.g., about 9 to 13 mm. The largest diameter of flared end region 14 may be selected so as to avoid mechanically loading the limbus of the fossa ovalis 42, which might otherwise cause inflammation. The largest diameter of flared end region 18 may be selected so as to provide a sufficient angle between flared end regions 14 and 18 to stabilize shunt 10 in the atrial septum, while limiting the extent to which flared end region 18 protrudes into the left atrium (e.g., inhibiting interference with flow from the pulmonary veins), and providing sufficient blood flow from the left atrium through neck region 16.

The length of end region 14 may be selected to protrude into the right atrium by a distance sufficient to inhibit tissue ingrowth that may otherwise interfere with the operation of shunt 10. Applicants have observed that tissue ingrowth inwards along an impermeably membranes of specified biomaterials from the end that contacts tissue generally stops after about 3 mm. Accordingly, to ensure that tissue ingrowth from the ends of the conduit does not extend into and partially occlude the flow area of neck region 16, the distance R between the narrowest portion of neck region 16 and the end of region 14 should be at least 3 mm plus half of the thickness of the septal region, i.e., fossa ovalis, contacting the exterior of shunt 10. Assuming that the fossa ovalis has a thickness of about 3.0 mm, then the minimum distance R should be about 4.5 mm, based on applicants' observations. Likewise, end region 18 preferably does not significantly engage the left side of atrial septum 45, so that distance L also preferably is at least 4.5 mm. Due to patient-to-patient variability in the thickness of the FO, e.g., due to the patient's general health and age, and because neck region 16 may not be precisely aligned with the mid-point of the FO, each distances R and L preferably fall within a range of 3 to 6 mm. Accordingly, for some embodiments, the overall dimensions of shunt 10 may be about 9-12 mm long (L+R, in FIG. 3B) to prevent tissue ingrowth from the ends of the conduit, i.e., end regions 14 and 18, from partially occluding neck region 16.

In another preferred embodiment, regardless of the geometrical shape of the conduit, there should be a minimum of 3 mm of material resistant to translational tissue growth, i.e., extending inward from the ends of the end regions to accommodate neoendocardial tissue growth over the shunt surfaces starting from a location in contact with the atrial septum, such that tissue growth cannot reach the orifice (site of minimal diameter of the shunt lumen or cross-sectional area of lumen 22 shown in FIG. 1B). With this preferred embodiment, the minimal orifice diameter of an interatrial shunt device will be rendered largely unaffected by pannus formation. In another preferred embodiment, there should be a minimum of 3 mm of conduit length for neoendocardial tissue to grow over the shunt luminal surfaces starting from a location in contact with the atrial septum, before reaching the entrance or exit port sites of the shunt lumen. With such an embodiment, there is even less potential for pannus to encroach the shunt lumen.

Figure 4A:
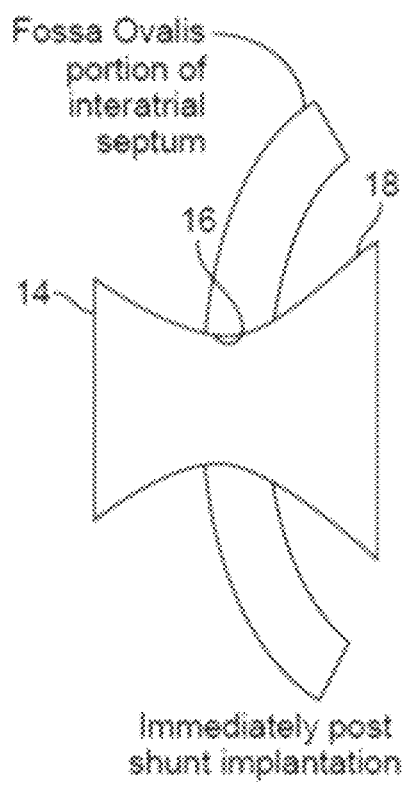
FIGS. 4A and 4B schematically depict pannus formation on an hourglass-shaped embodiment of an interatrial shunt positioned in the fossa ovalis orthogonal to the atrial septum wall, immediately after implantation and after pannus formation.
Figure 4B:
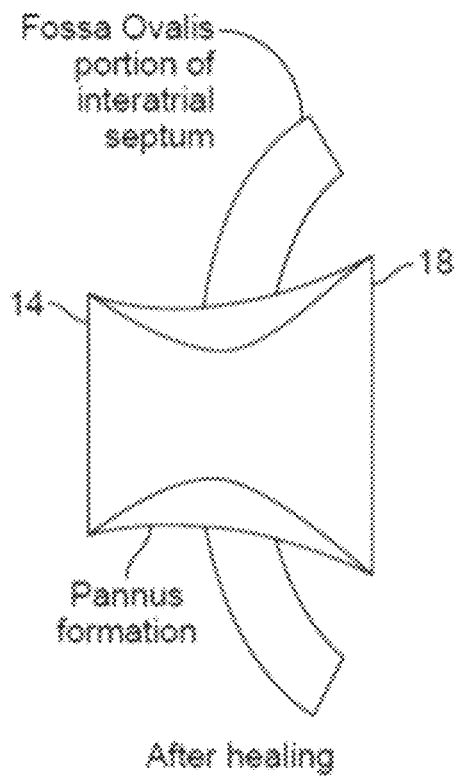
Figure 5A:
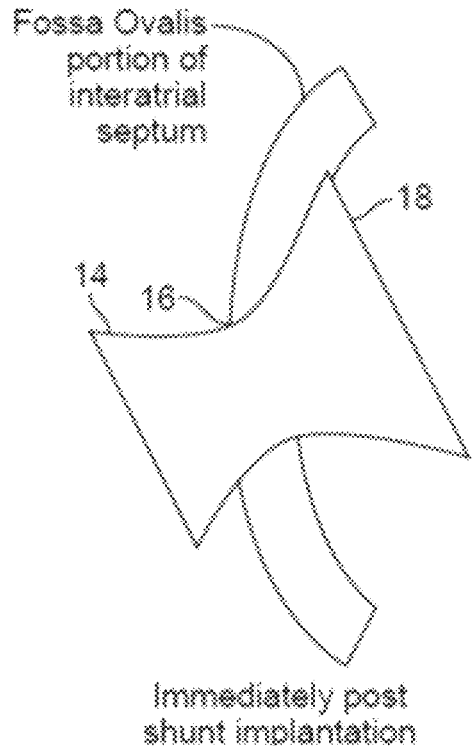
FIGS. 5A and 5B schematically depict pannus formation on an hourglass-shaped embodiment of an interatrial shunt positioned in the fossa ovalis non-orthogonal to the atrial septum wall, invention immediately after implantation and after pannus formation.
Figure 5B:
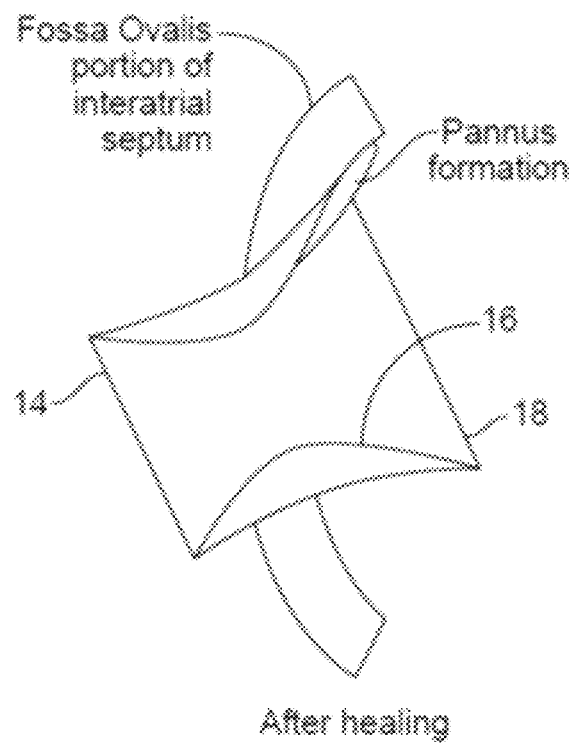

Referring now to FIGS. 4A and 4B, the expected healing response invoked by implanting shunt 10 of FIGS. 1A-1C orthogonally across the FO is described, while FIGS. 5A and 5B correspond to implantation of the shunt non-orthogonally so that an outer surface of the LA entry cone contacts the atrial septal tissue. FIGS. 4A and 5A depict positioning of the shunts immediately post implantation, while FIGS. 4B and 5B depict shunt positioning after the completion of the healing phase.

In each of FIGS. 4A and 4B, the FO is shown as bowed towards the RA and concave towards the LA. In patients with dilated cardiomyopathy or restrictive physiology, including most patients with left ventricular failure, regardless of etiology, the FO portion of the interatrial septum generally is bowed toward the right atrium. This gives the LA a generally concave or near hemispherical shape in the region centered on the FO. Conversely, the RA side of the FO is generally convex in shape. This orientation of the FO was confirmed by echocardiography (n=178 examinations)

in the 38 patients implanted with the V-Wave Nitzan-type valved shunt discussed in the Background of the Invention portion of this specification. In measurements of more than 100 patients exhibiting heart failure with preserved ejection fraction ("HFpEF"), the LA volume generally averaged 85 ml with a minimum volume of 54 ml, while for a like number of patients exhibiting heart failure with reduced ejection fraction ("HFrEF"), the LA volume generally averaged 104 ml with a minimum volume of 71 ml. Although the LA is often approximated by a sphere or an ellipsoid, there are frequently exceptions to this, for example, where the LA appears squashed when viewed in its anterior-posterior dimension. Although not specifically quantified, the RA appeared to be similar in size to the LA.

Although exceptions to RA bowing of septal anatomy occur, they generally do so in the presence of isolated right ventricular failure or severe pulmonary hypertension in the absence of left ventricular dysfunction or mitral valve disease, e.g. as occurs in pulmonary arterial hypertension ("PAH"). In those instances, RA pressure tends to exceed LA pressure causing the FO to bow in the opposite direction toward the LA. Such patients generally would derive no clinical benefit from left-to-right interatrial shunting. However, patients with severe pulmonary hypertension in the absence of left-sided heart failure may benefit from right-to-left shunting as a means to improve low systemic cardiac output. Several of the embodiments described in this disclosure would be provide improved performance compared to right-to-left shunts currently available to that population of patients.

Another geometrical constraint is the frequent presence or need to place transvenous endocardial electrical pacing or defibrillation leads in or through the RA of heart failure patients. In the 38-patient feasibility study conducted with the V-Wave Nitzan-type shunt, 74% of patients had already been implanted with cardiac rhythm management devices prior to interatrial shunting. Most of these patients had 2 or 3 such electrical leads placed. Leads most often enter the RA from the superior vena cava ("SVC"). Right atrial pacing leads usually loop up and terminate anterio-laterally in the RA appendage, but in some circumstances, they are attached to a muscular portion of the interatrial septum. RV pacing and defibrillation leads usually course along the lateral wall of the RA, then cross the tricuspid valve, and terminate in the interventricular septum, RV apex, or pulmonary outflow tract. LV leads enter the coronary sinus, which is just below and anterior to the FO. Occasionally, leads must be placed from unusual sites of origin and may enter the RA from the inferior vena cava ("IVC"). Leads are usually left with enough slack so that they do not put tension on their terminal ends when the heart moves or changes position. Much of this slack results in a web of excess lead body material that is often concentrated in the RA.

The observations of septal bowing, the range of chamber dimensions observed and the consequences of multiple transvenous endocardial lead placement have important implications for interatrial shunt device design. If a shunt protrudes into the LA chamber, it preferably is placed so that it generally projects orthogonally with respect to the FO as shown in FIG. A. Orthogonal placement is expected to minimize impingement on other adjacent or nearby critical cardiac structures, such as the aortic root, the mitral valve annulus, the roof and the posterior wall of the LA, and the pulmonary veins. Alternatively, if not placed substantially orthogonally, as shown in FIG. 5A, the shunt geometry should be selected to prevent the shunt from interacting with these structures. Proper accounting for such design considerations will prevent erosion of the shunt into critical cardiac structures, and prevent blockage of flow through the shunt by luminal impingement by adjacent cardiac structures. Ideally, the shunt should also occupy minimal space within the LA and only minimally disturb its normal flow pattern. The LA fills from the pulmonary veins during ventricular systole and drains into the left ventricle when the mitral valve opens during diastole. Blood coming from the right superior pulmonary veins tends to course along and hug the interatrial septum preventing stasis near the FO.

In a preferred embodiment of shunt 10, the volume of blood displaced by the portion of the shunt protruding into the LA, i.e., the volume of blood in the portion of the shunt lumen protruding into the LA, should be less than or equal to 5% of the LA diastolic volume expected in the patient population. This is typically 2.0 ml or less in adult patients with heart failure. Moreover, the shunt should not protrude into the LA by more than 15 mm, or more typically 3 to 10 mm. These dimensional considerations may also be accomplished in conjunction with other shunt features that facilitate a substantially orthogonal orientation, such as an LA entry funnel.

Similar considerations exist for the RA side of the FO. The shunt should occupy a minimal volume and have only a small effect on normal flow patterns. In a preferred embodiment, the same occupying volume and protrusion distance considerations, apply to the RA side of the shunt, that is, the device and its lumen should occupy less than or equal to 5% of the RA diastolic volume, e.g., 2.0 ml or less in adult patients with heart failure, and protrude into the RA by no more than, for example, 15 mm, or more typically 3 to 10 mm. These dimensional considerations can also be accomplished in conjunction with other shunt features that facilitate a substantially orthogonal orientation, such as RA exit funnel. These same criteria apply when the shunt is used in an application where RA to LA shunting is desirable, e.g., pulmonary arterial hypertension ("PAH"). The shunt should protrude in the RA the least amount necessary so that it does not foul pacing leads or abrade their electrical insulation.

As described earlier, the propensity for venous thromboembolism ("VTE") to cross in the retrograde direction through a shunt is expected to be a function of not only the amount and duration of retrograde shunt flow from the RA to the LA, but also a result of the flow patterns in the RA. The path of flow in the adult RA is complex because blood enters the chamber from multiple sources which include the inferior vena cava ("IVC"), the superior vena cava ("SVC"), the coronary sinus and from the LA through the shunt. These flow paths include directional changes and asymmetries whose topology has been assessed by color flow Doppler imaging and more recently from magnetic resonance velocity mapping.

Since the overwhelming majority of VTE in adult patients originate from the lower extremities and pelvic veins, the path traveled by paradoxical emboli are most likely similar to the flow vectors for blood coming from the IVC. Flow from the inferior vena cava courses along the posterior wall of the RA chamber before looping around the roof, where it is directed toward the tricuspid valve by coursing along the interatrial septum. The rest of the cavity generally contains pooled blood. Thus, blood entering the RA from the IVC forms a clockwise vortex descending along the RA side of the interatrial septum in most patients with normal anatomy. Advantageously, this flow pattern of blood downwards from the roof of the RA and along the interatrial septum reduces the risk of blood pooling in the vicinity of neck region 16 of the inventive shunt 10, thus reducing the risk of local thrombus formation due to blood stasis. Further, these flow pathway observations suggest that a thrombus originating from inferior vena cava will a have a trajectory that passes very close to the RA orifice of a naturally occurring secundum type atrial septal defect or an orifice-plate mesh type shunt. Because in this case thrombus is essentially presented by the flow path within the RA to the orifice, even a small reversal of shunt flow could embolize the thrombus across the orifice into the LA.

Preferably, the shunt includes an exit port (end region 14) that extends a distance into the RA, e.g., 3 to 15 mm, or more typically 5 to 10 mm, sufficient to place the orifice of the exit port out of the naturally occurring flow paths in the RA. In particular, the exit port projects partially or completely through the stream of blood originating from the IVC that loops down across the interatrial septum. Such a shunt geometry thus will be expected to have a lower risk of paradoxical embolization compared with an orifice-plate mesh type shunt where the exit port is directed at the passing looped IVC flow stream.

Referring now to FIGS. 6A through 6E, an exemplary embodiment of a shunt constructed in accordance with the principles of the present invention is provided. Shunt 50 is constructed similar to shunt 10 of FIGS. 1A to 1C. For example, shunt 50 is formed of a metal frame and encapsulated with a biocompatible material. Specifically, shunt 50 generally comprises an anchor having three regions: flared or funnel-shaped end region 51 having inlet end 52, flared or funnel-shaped end region 54 having outlet end 55, and neck region 53 disposed between end regions 51 and 54. Neck region 53 is configured to lodge in a puncture formed in the atrial septum, preferably in the fossa ovalis. Flared end regions 51 and 54 are configured to partially engage and protrude beyond the right and left sides, respectively, of the atrial septum when implanted. Shunt 50 further comprises a conduit, illustratively formed by encapsulating the anchor with biocompatible material 56 that covers all or substantially all of the anchor to form a conduit defining a lumen or interior passageway.

Flared region 51 is configured to be disposed in the right atrium, while flared region 54 is configured to be disposed in the left atrium. In one embodiment, the anchor includes six longitudinal struts 57 interconnected by five circumferential struts 58a-58e. Longitudinal struts 57 prevent foreshortening of the anchor during expansion, while the sinusoidal or serpentine bends in circumferential struts 58a-58e permit the anchor to transition between a radially collapsed substantially cylindrical delivery state to an expanded, flared, deployed state. As depicted in the figures, a conduit is formed by biocompatible material 56 that encapsulates the entirety of neck region 53, flared end region 54, and flared end region 51. Biocompatible material 56 preferably is affixed to the anchor using a suitable biocompatible adhesive or by sandwiching the anchor between inner and outer layers of biocompatible material using sintering techniques.

In a preferred embodiment, the anchor comprises a self-expanding material, such as a shape memory alloy, and circumferential struts 58a-58e are treated to expand a predetermined amount when deployed, so that together with encapsulation 56, the passageway has a contour that permits substantially laminar flow between flared end section 51 (in the left atrium) and flared end section 54 (in the right atrium). The sinusoidal or serpentine bends in circumferential struts on flared end region 52 preferably are 180 degrees out of phase with the sinusoidal or serpentine bends in neck region 53 and flared end region 54, so that the sinusoidal or serpentine bends do not extend beyond the ends of longitudinal struts 57 in either the collapsed delivery state or deployed state.

The anchor may comprise a biocompatible metal framework or laser-cut solid metallic tube made from nitinol, titanium alloy, cobalt chromium alloy, MP35n, 316 stainless steel, L605, Phynox/Elgiloy, platinum chromium or other biocompatible metal such as are known to persons of skill in the art. While a preferred embodiment employs a shape memory self-expanding alloy, the anchor alternatively may comprise an elastically or plastically deformable material, e.g., balloon expandable, or may be a shape memory alloy that responds to temperature changes to transition between contracted delivery and expanded deployed states. The surface finish applied to the material of the anchor may be selected to control the distance, thickness, composition and/or growth pattern of pannus formation, e.g., the external surfaces of the anchor may be electro-polished.

Biocompatible material 56 forming the conduit preferably is resistant to the transmural and translational ingrowth of pannus material having a tissue thickness greater than 0.6 mm. For example, in experimental ePTFE vascular grafts, those with a 60-micron internodal distance showed rapid, transmural infiltration with proliferating smooth muscle cells and granulation tissue, whereas ePTFE grafts with a 30-micron internodal distance were observed to develop only a slow growing, thin sheet of endothelium that advanced only a few millimeters into the graft lumen from the adjacent artery. Porous polyester fabric coverings employed on some atrial septal defect ("ASD") occlusion devices would be poor choices for use in the shunt of the present invention, because such materials become completely enmeshed with penetrating fibrotic tissue. It is expected that when shunt 50 comprises an anchor made of, for example, electro polished nitinol, and biocompatible material 56 may be an inert polymer such as ePTFE with an internodal distance of 30 microns or less, or is PTFE, such that pannus will grow to a thickness no greater than about 0.6 mm after extending translationally a distance of 3 mm from the site of contact with the Foramen Ovalis ("FO") tissue. In such cases, interior lumen of the conduit is not expected to narrow beyond a total of 1.2 mm from its original diameter and the neck. For the purposes of this patent the term "luminal narrowing" shall be defined as a loss of minimal shunt lumen diameter of greater than 25% and the term "luminal obstruction" is defined as total (100% loss of lumen diameter) blockage of the lumen to the flow of blood.

Circumferential struts 58a-58e and longitudinal struts 57 preferably comprise a unitary construction, that is, the entire anchor is laser cut from a tube of shape memory metal. Biocompatible material 56 may comprise, for example, a sheet of a polymer such as expanded polytetrafluoroethylene ("ePTFE"), polytetrafluoroethylene ("PTFE",) silicone, polycarbonate urethane, DACRON (polyethylene terephthalate), Ultra High Molecular Weight Polyethylene (UHMWPE), or polyurethane. The biocompatible material may also be a metal, ceramic, carbon nanotube array or any other suitable biocompatible material. For example, biocompatible material 56 may comprise ePTFE with an up to 30-micron internodal distance, and may be applied as inner and outer layers sintered together to form a unitary conduit. Alternatively, biocompatible material 56 may be applied to the inner lumen and the outside of the anchor using electrospinning techniques. Other methods of encapsulation and other suitable polymers that prevent transmural ingrowth of pannus tissue may alternatively be used, as will be understood by one skilled in the art. Bare metal regions of the anchor, and any other regions of the anchor, optionally may be electropolished or otherwise treated to inhibit thrombus formation using known methods.

Figure 6A:
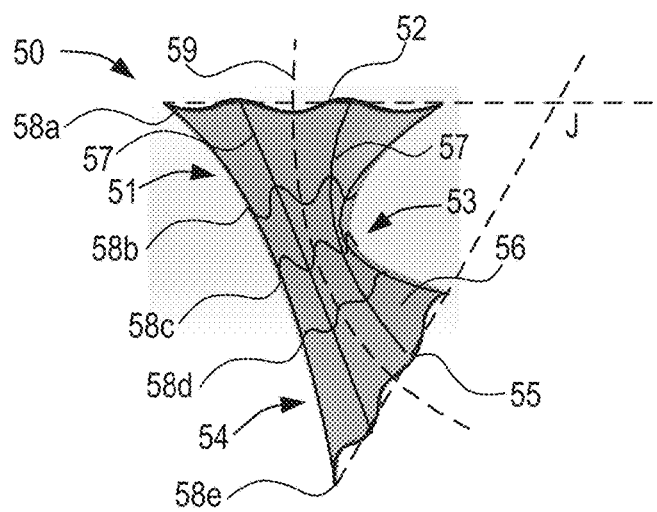
FIGS. 6A to 6D illustrate various perspectives of an alternative exemplary embodiment of a shunt constructed in accordance with the principles of the present invention.
Figure 6B:
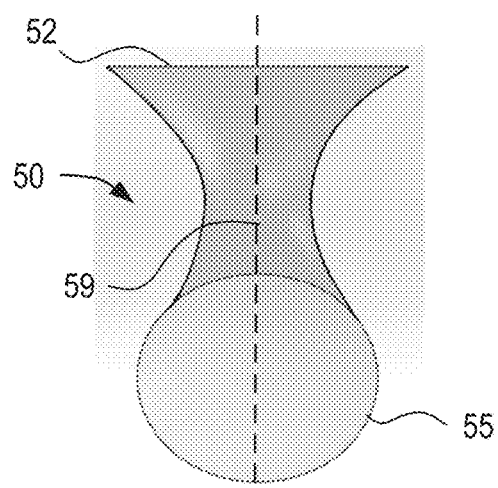

Shunt 50 differs from shunt 10 of FIGS. 1A to 1C in that shunt 80 is curved along central longitudinal axis 81. As illustrated in FIG. 6A, inlet end 52 at the LA entry port in the LA is in a first plane, and outlet end 55 at the RA exit port in the RA is in a second plane different from the first plane, such that the first and second planes intersect at point J. For example, the first and second planes may intersect an angle between 20 and 45 degrees, e.g., 30 degrees. FIG. 6A illustrates a first profile of shunt 50 having a first orientation, whereas FIG. 6B illustrates a second profile of shunt 80 having a second orientation, looking into outlet end 83 of shunt 80. By comparing FIGS. 6A and 6B, the second orientation of the second profile of shunt 50 is approximately 90 degrees from the first orientation of the first profile of shunt 50 when shunt 50 is rotated about central longitudinal axis 59 of shunt 50. As shown in FIG. 6A, from the first profile of shunt 50, central longitudinal axis 59 has a curved shape, whereas in FIG. 6B, from the second profile of shunt 50, central longitudinal axis 59 is a straight line. As will be understood by a person ordinarily skilled in the art, central longitudinal axis 59 may be curved in a manner such that no profile of shunt 50 at any orientation depicts central longitudinal axis 59 as a straight line, e.g., when central longitudinal axis 59 has a helical shape.

Figure 6C:
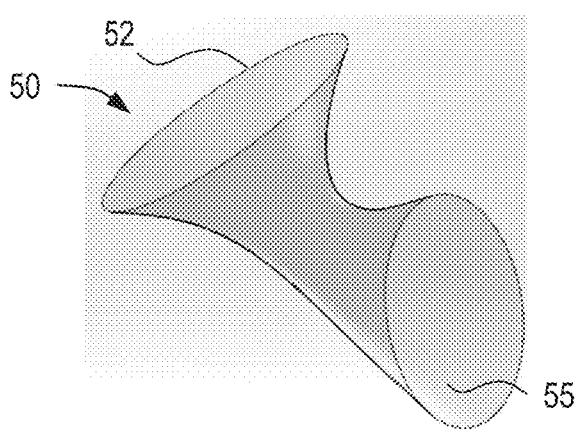
Figure 6D:
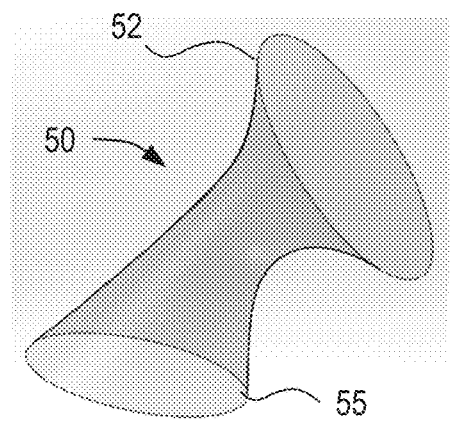
Figure 6E:
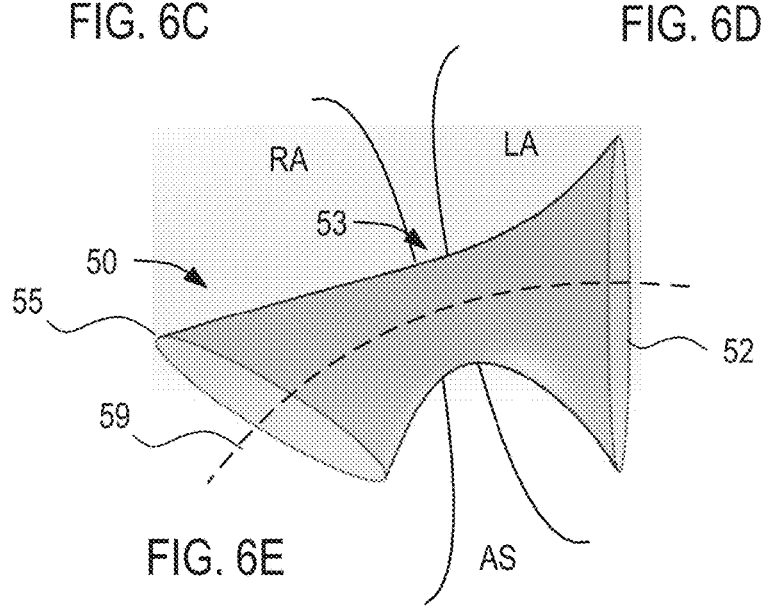
FIG. 6E illustrates the shunt of FIGS. 6A to 6D with respect to the atrial septum in an expanded deployed configuration.

FIGS. 6C and 6D illustrate shunt 50 from additional views. FIG. 6E illustrates shunt 50 when implanted in a hole within the atrial septum. As shown in FIG. 6E, neck region 53 of shunt 50 is situated in a passage formed in atrial septum AS, such that inlet end 52 of shunt 50 is disposed within left atrium LA and outlet end 55 of shunt 50 is disposed within right atrium RA of the patient. Accordingly, as blood enters shunt 50 through inlet end 52, blood flow is redirected along the curvature of central longitudinal axis 59 of shunt 50, and exits shunt 50 via outlet end 55 into right atrium RA at a different angle from the direction of blood flow path through inlet end 52. For example, blood may enter inlet end 52 of shunt 50 from within the left atrium LA at an entry angle substantially perpendicular to the atrial septum AS, and exit outlet end 55 of shunt 50 in the right atrium RA at an exit angle relative to the entry angle that is equivalent to the angle at which the first plane intersects the second plane at point J.

Figure 7A:
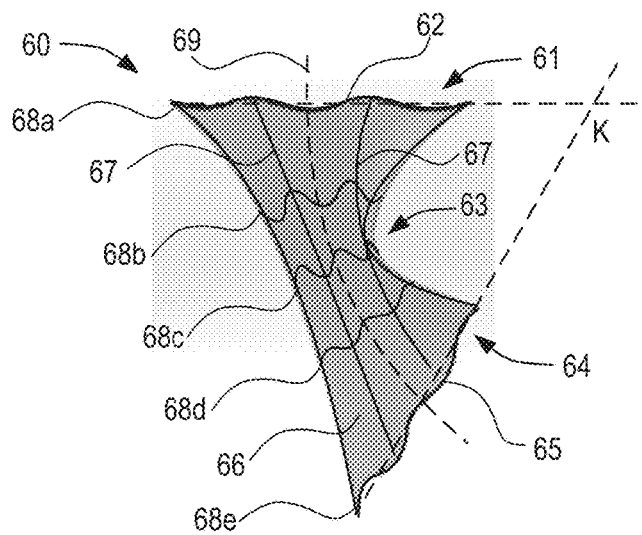
FIGS. 7A to 7E illustrate various perspectives of another alternative exemplary embodiment of a shunt constructed in accordance with the principles of the present invention.
Figure 7B:
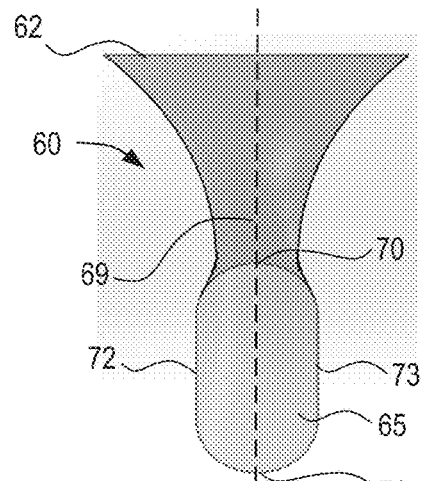

Referring now to FIGS. 7A through 7F, an alternative exemplary embodiment of a shunt constructed in accordance with the principles of the present invention is provided. Shunt 60 is constructed similar to shunt 50 of FIGS. 6A to 6E. For example, as illustrated in FIG. 7A, inlet end 62 at first flared end region 61, e.g., the LA entry port in the LA, is in a first plane, and outlet end 65 at second flared end region 64, e.g., the RA exit port in the RA, is in a second plane different from the first plane, such that the first and second planes intersect at point K. For example, the first and second planes may intersect an angle between 20 and 45 degrees, e.g., 30 degrees. Shunt 60 may, for example, be formed of a metal frame and encapsulated with a biocompatible material. FIG. 7A illustrates a first profile of shunt 60 having a first orientation, whereas FIG. 7B illustrates a second profile of shunt 60 having a second orientation, looking into outlet end 65 of shunt 60. By comparing FIGS. 7A and 7B, the second orientation of the second profile of shunt 60 is approximately 90 degrees from the first orientation of the first profile of shunt 60 when shunt 60 is rotated about central longitudinal axis 69 of shunt 60. As shown in FIG. 7A, from the first profile of shunt 60, central longitudinal axis 69 has a curved shape, whereas in FIG. 7B, from the second profile of shunt 60, central longitudinal axis 69 is a straight line. As will be understood by a person ordinarily skilled in the art, central longitudinal axis 69 may be curved in a manner such that no profile of shunt 60 at any orientation depicts central longitudinal axis 69 as a straight line, e.g., when central longitudinal axis 69 has a helical shape.

Figure 7C:
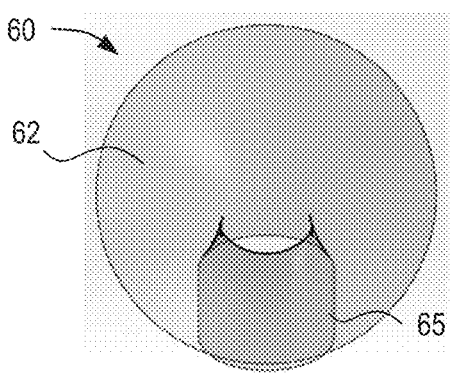

Shunt 60 differs from shunt 50 in that inlet end 62 at the LA entry port in the LA has a cross-sectional shape different from the cross-sectional shape of outlet end 65 at the RA exit port in the RA. As illustrated in FIG. 7B, outlet end 65 of shunt 60 has a cross-sectional shape having a first pair of opposing sides that extend parallel and a second pair of opposing ends that curve. For example, the cross-sectional shape of outlet end 65 has two rounded ends 70 and 71, opposite from one another, and two flattened portions 72 and 73, opposite from one another. Alternatively, the cross-sectional shape of outlet end 65 of shunt 60 may be an ellipse or an oval. In addition, as illustrated in FIG. 7C, inlet end 62 of shunt 60 has a cross-sectional shape of a circle. As further illustrated in FIGS. 7A and 7B, central longitudinal axis 69 of shunt 60 may be curved such that rounded end 70 of outlet end 65 is closest in proximity to inlet end 62. As will be understood by a person ordinarily skilled in the art, central longitudinal axis 69 of shunt 60 may be curved such that rounded end 71 of outlet end 65 is closest in proximity to inlet end 62. The width of outlet end 65, e.g., the distance between rounded ends 70 and 71, may be equal to the diameter of the cross-sectional shape of circular inlet end 62. Therefore, outlet end 65 may have a cross-sectional area that is less than the cross-sectional area of circular inlet end 62, and thus, as will be understood by a person ordinarily skilled in the art, blood may exit outlet end 65 at a faster rate than blood entering shunt 60 via inlet end 62. In accordance with another aspect of the present invention, the width of outlet end 65 may be larger than or less than the diameter of the cross-sectional shape of circular inlet end 62, such that a desired blood flow rate at outlet end 65 may be achieved.

Figure 7D:
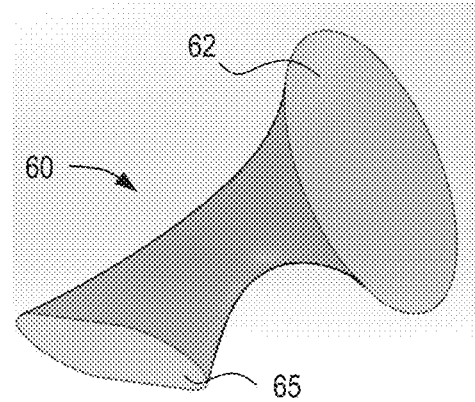
Figure 7E:
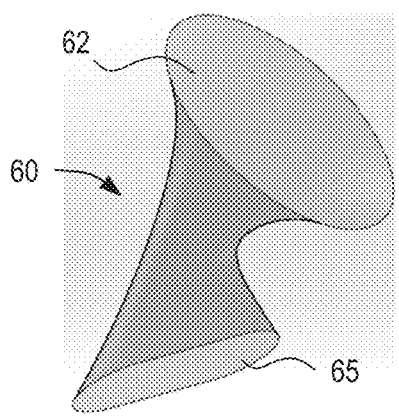
Figure 7F:
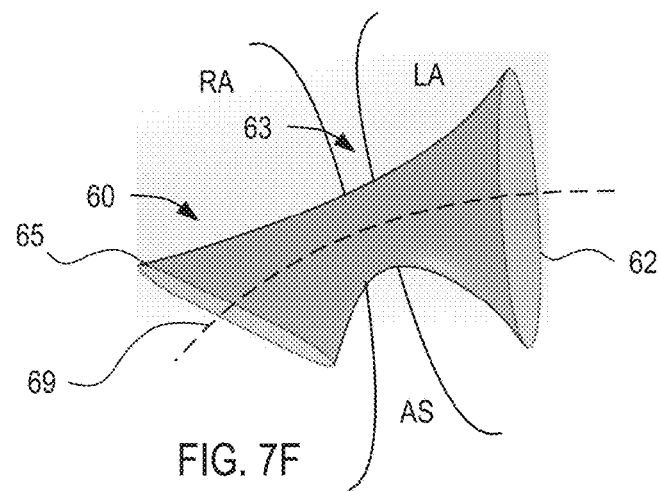
FIG. 7F illustrates the shunt of FIGS. 7A to 7E with respect to the atrial septum in an expanded deployed configuration.

FIGS. 7D and 7E illustrate shunt 60 from additional views at different orientations. FIG. 7F illustrates shunt 60 when implanted in a hole within the atrial septum. As shown in FIG. 7F, neck region 63 of shunt 60 is situated in a passage formed in atrial septum AS, such that inlet end 62 of shunt 60 is disposed within left atrium LA and outlet end 65 of shunt 60 is disposed within right atrium RA of the patient. Accordingly, as blood enters shunt 60 through inlet end 62, blood flow is redirected along the curvature of central longitudinal axis 69 of shunt 60, and exits shunt 60 via outlet end 65 into right atrium RA at a different angle from the direction of blood flow path through inlet end 62, and optionally at a faster rate than blood flow entry through inlet end 62. For example, blood may enter inlet end 62 of shunt 60 from within the left atrium LA at an entry angle substantially perpendicular to the atrial septum AS, and exit outlet end 65 of shunt 60 in the right atrium RA at an exit angle relative to the entry angle that is equivalent to the angle at which the first plane intersects the second plane at point K.

Figure 8A:
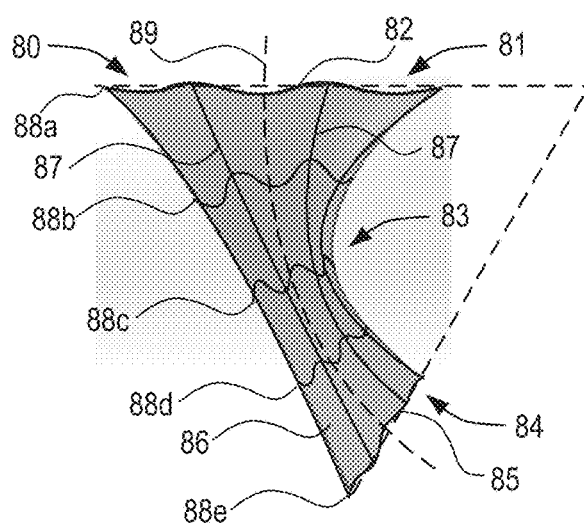
FIGS. 8A to 8D illustrate various perspectives of yet another alternative exemplary embodiment of a shunt constructed in accordance with the principles of the present invention.
Figure 8B:
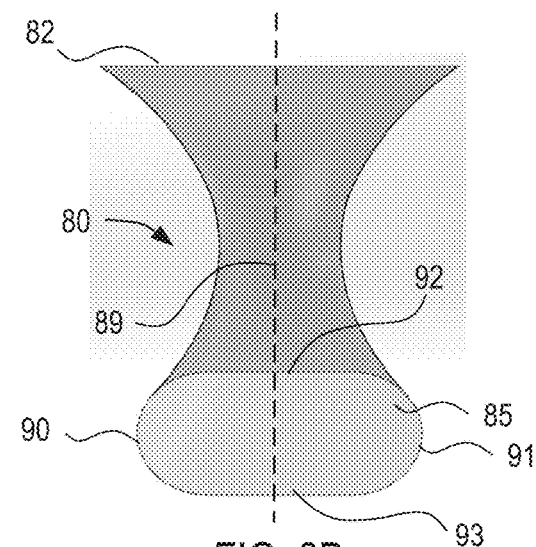

Referring now to FIGS. 8A through 8E, an alternative exemplary embodiment of a shunt constructed in accordance with the principles of the present invention is provided. Shunt 80 is constructed similar to shunt 60 of FIGS. 7A to 7F. For example, as illustrated in FIG. 8A, inlet end 82 at first flared end region 81, e.g., the LA entry port in the LA, is in a first plane, and outlet end 85 at second flared end region 84, e.g., the RA exit port in the RA, is in a second plane different from the first plane, such that the first and second planes intersect at point L. For example, the first and second planes may intersect an angle between 20 and 45 degrees, e.g., 30 degrees. Shunt 80 may, for example, be formed of a metal frame and encapsulated with a biocompatible material. FIG. 8A illustrates a first profile of shunt 80 having a first orientation, whereas FIG. 8B illustrates a second profile of shunt 80 having a second orientation, looking into outlet end 85 of shunt 80. By comparing FIGS. 8A and 8B, the second orientation of the second profile of shunt 80 is approximately 90 degrees from the first orientation of the first profile of shunt 80 when shunt 80 is rotated about central longitudinal axis 89 of shunt 80. As shown in FIG. 8A, from the first profile of shunt 80, central longitudinal axis 89 has a curved shape, whereas in FIG. 8B, from the second profile of shunt 80, central longitudinal axis 89 is a straight line. As will be understood by a person ordinarily skilled in the art, central longitudinal axis 89 may be curved in a manner such that no profile of shunt 80 at any orientation depicts central longitudinal axis 89 as a straight line, e.g., when central longitudinal axis 89 has a helical shape.

In addition, like shunt 60 of FIGS. 7A to 7F, outlet end 85 of shunt 80 has a cross-sectional shape having a first pair of opposing sides that extend parallel and a second pair of opposing ends that curve. For example, the cross-sectional shape of outlet end 85 has two rounded ends 90 and 91, opposite from one another, and two flattened portions 92 and 93, opposite from one another. Alternatively, the cross-sectional shape of outlet end 85 of shunt 80 may be an ellipse or an oval. Shunt 80 differs from shunt 60 in that central longitudinal axis 89 of shunt 80 is curved such that flattened portion 92 of outlet end 85 is closest in proximity to inlet end 82. As will be understood by a person ordinarily skilled in the art, central longitudinal axis 89 of shunt 80 may be curved such that flattened portion 93 of outlet end 85 is closest in proximity to inlet end 82.

Figure 8C:
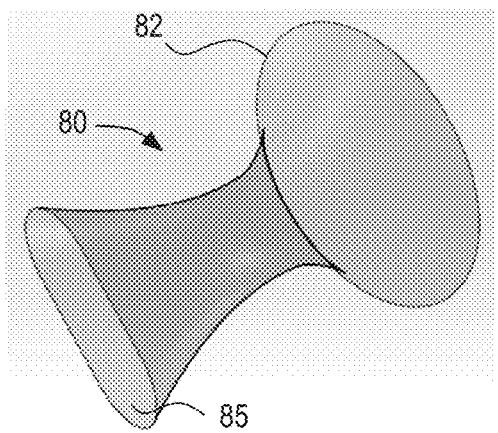
Figure 8D:
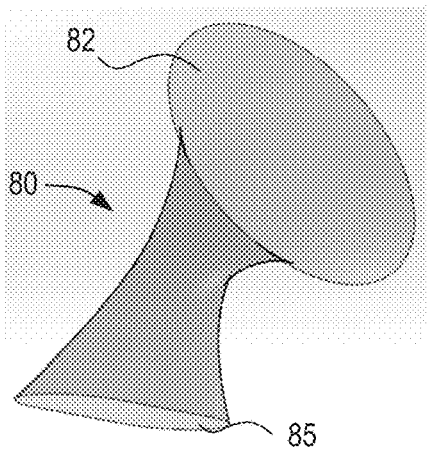
Figure 8E:
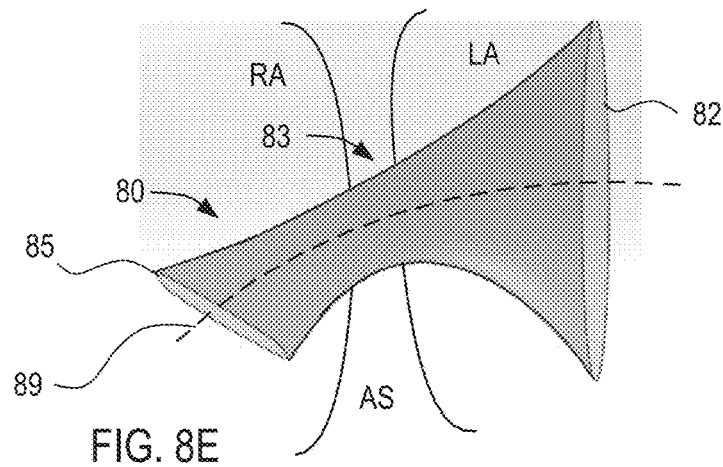
FIG. 8E illustrates the shunt of FIGS. 8A to 8D with respect to the atrial septum in an expanded deployed configuration.

FIGS. 8C and 8D illustrate shunt 80 from additional views at different orientations. FIG. 8E illustrates shunt 80 when implanted in a hole within the atrial septum. As shown in FIG. 8E, neck region 83 of shunt 80 is situated in a passage formed in atrial septum AS, such that inlet end 82 of shunt 80 is disposed within left atrium LA and outlet end 85 of shunt 80 is disposed within right atrium RA of the patient. Accordingly, as blood enters shunt 80 through inlet end 82, blood flow is redirected along the curvature of central longitudinal axis 89 of shunt 80, and exits shunt 80 via outlet end 85 into right atrium RA at a different angle from the direction of blood flow path through inlet end 82, and optionally at a faster rate than blood flow entry through inlet end 82. For example, blood may enter inlet end 82 of shunt 80 from within the left atrium LA at an entry angle substantially perpendicular to the atrial septum AS, and exit outlet end 85 of shunt 80 in the right atrium RA at an exit angle relative to the entry angle that is equivalent to the angle at which the first plane intersects the second plane at point L.

Referring now to FIGS. 9A through 9E, an alternative exemplary embodiment of a shunt constructed in accordance with the principles of the present invention is provided. Shunt 100 is constructed similar to shunt 10 of FIGS. 1A to 1C, except that inlet end 102 at first flared end region 101, e.g., the LA entry port in the LA, has a cross-sectional shape different from the cross-sectional shape of outlet end 105 at second flared end region 104, e.g., the RA exit port in the RA. Shunt 100 may, for example, be formed of a metal frame and encapsulated with a biocompatible material.

Figure 9A:
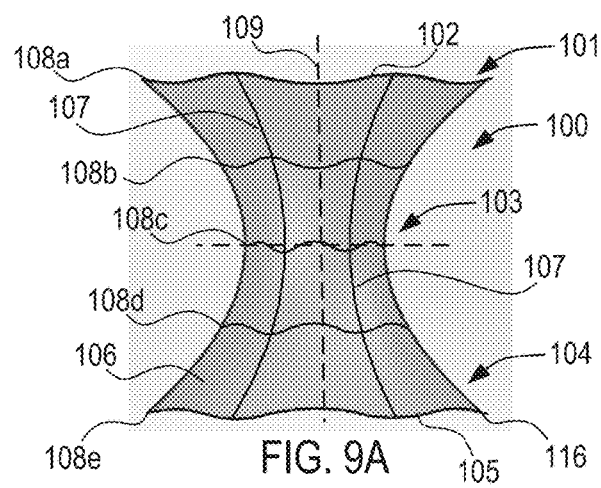
FIGS. 9A to 9D illustrate various perspectives of an alternative exemplary embodiment of a shunt constructed in accordance with the principles of the present invention.
Figure 9B:
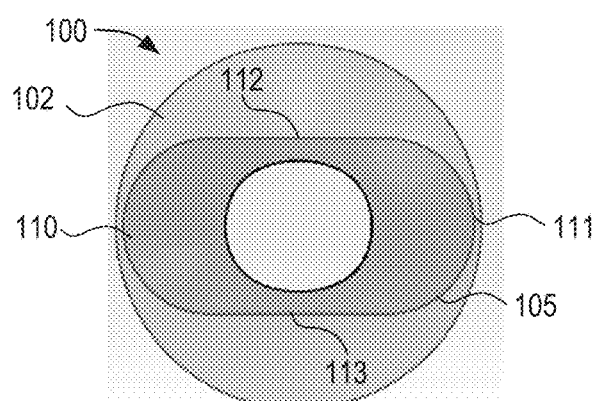

FIG. 9B illustrates shunt 100 from a profile having an orientation where shunt 100 of FIG. 9A is rotated 90 degrees about the horizontal dotted line. Thus, rounded ends 110 and 111 of outlet end 105 are depicted as opposing ends of outlet end 105 in FIG. 9B. As illustrated in FIG. 9B, inlet end 102 of shunt 100 has a cross-sectional shape of a circle, and outlet end 105 of shunt 100 has a cross-sectional shape having a first pair of opposing sides that extend parallel and a second pair of opposing ends that curve. For example, the cross-sectional shape of outlet end 105 has two rounded ends 110 and 111, opposite from one another, and two flattened portions 112 and 113, opposite from one another. Alternatively, the cross-sectional shape of outlet end 105 of shunt 100 may be an ellipse or an oval.

As shown in FIG. 9B, the width of outlet end 105, e.g., the distance between rounded ends 110 and 111, may be approximately equal to the diameter of the cross-sectional shape of circular inlet end 102. Therefore, outlet end 105 may have a cross-sectional area that is less than the cross-sectional area of circular inlet end 102, and thus, as will be understood by a person ordinarily skilled in the art of fluid mechanics, blood may exit outlet end 105 at a faster rate than blood entering shunt 100 via inlet end 102. In accordance with another aspect of the present invention, the width of outlet end 105 may be larger than or less than the diameter of the cross-sectional shape of circular inlet end 102, such that a desired blood flow rate at outlet end 105 may be achieved.

Figure 9C:
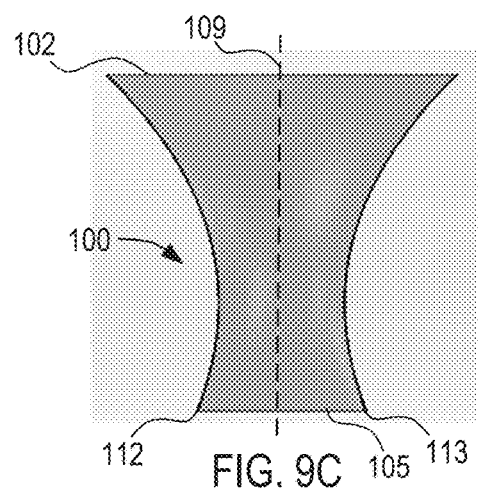
Figure 9D:
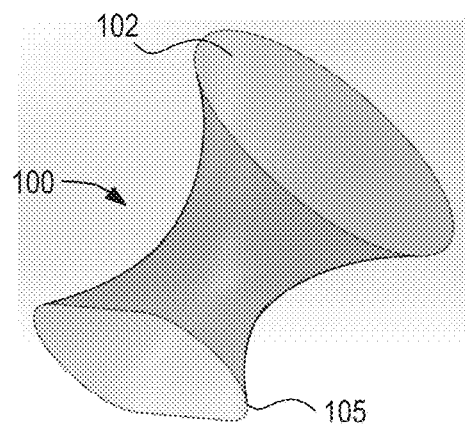
Figure 9E:
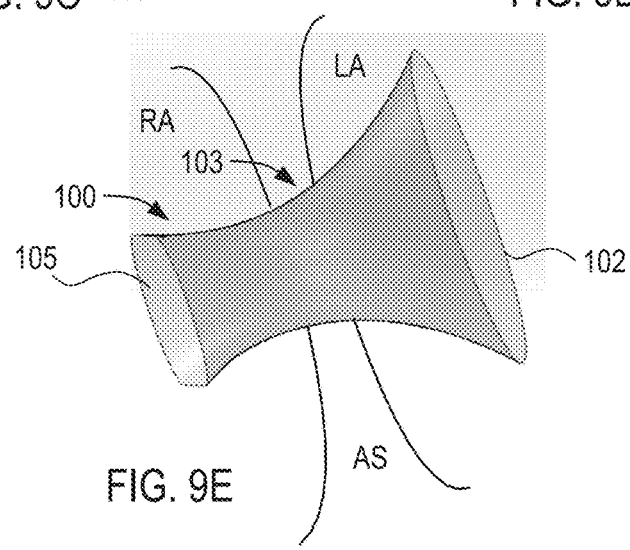
FIG. 9E illustrates the shunt of FIGS. 9A to 9D with respect to the atrial septum in an expanded deployed configuration.

FIG. 9C illustrates shunt 100 from a profile having an orientation where shunt 100 of FIG. 9A is rotated 90 degrees about central longitudinal axis 109. Thus, flattened portions 112 and 113 of outlet end 105 are depicted as opposing ends of outlet end 105 in FIG. 9C. FIG. 9D illustrates shunt 100 from an additional view. FIG. 9E illustrates shunt 100 when implanted with respect to the atrial septum. As shown in FIG. 9E, neck region 103 of shunt 100 is situated in a passage formed in atrial septum AS, such that inlet end 102 of shunt 100 is disposed within left atrium LA and outlet end 105 of shunt 100 is disposed within right atrium RA of the patient. Accordingly, blood enters shunt 100 through inlet end 102, and exits shunt 100 via outlet end 105 into right atrium RA at faster rate than blood flow entry through inlet end 102.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

While various illustrative embodiments of the invention are described above, it will be apparent to one skilled in the art that various changes and modifications may be made herein without departing from the invention.

What is claimed:

1. An asymmetric device for regulating blood volume distribution across a patient's atrial septum, the device comprising:
    a first expandable end region configured to transition from a contracted delivery state to an expanded deployed state in which the first expandable end region extends into the patient's left atrium and an inlet end of the first expandable end region is in a first plane;
    a second expandable end region configured to transition from a contracted delivery state to an expanded deployed state in which the second expandable end region extends into the patient's right atrium and an outlet end of the second expandable end region is in a second plane; and a neck region joining the first expandable end region to the second expandable end region, the neck region configured for placement in the patient's atrial septum, wherein the first plane intersects the second plane.

2. The device of claim 1, wherein the inlet end of the first expandable end region has a first cross-sectional shape, and wherein the outlet end of the second expandable end region has a second cross-sectional shape different from the first cross-sectional shape of the inlet end of the first expandable end region in the expanded state.

3. The device of claim 2, wherein the first cross-sectional shape of the inlet end of first expandable end region in the expanded state is a circle.

4. The device of claim 2, wherein the second cross-sectional shape of the outlet end of the second expandable end region in the expanded state has a first pair of opposing sides that extend parallel and a second pair of opposing ends that curve.

5. The device of claim 1, wherein the first plane intersects the second plane at an angle between 20 and 45 degrees.

6. The device of claim 1, further comprising a central longitudinal axis, wherein from a first profile of the device having a first orientation, the central longitudinal axis has a curved shape.

7. The device of claim 6, wherein the central longitudinal axis of the device lies in a single plane.

8. The device of claim 1, further comprising a conduit having a lumen wall defining a lumen, the lumen wall resistant to transmural and translational tissue growth.

9. The device of claim 8, wherein the conduit has a first end that extends from the neck region a first distance of at least 3 mm into the patient's left atrium and a second end that extends from the neck region a second distance of at least 3 mm into the patient's right atrium, thereby preventing pannus formation from narrowing the lumen of the conduit in the neck region.

10. The device of claim 9, wherein the second end of the conduit extends from the neck region a distance of between 3 mm to 15 mm into the patient's right atrium.

11. The device of claim 8, wherein the conduit is configured so that when implanted the second end of the conduit is located out of a natural circulation flow path of blood entering into the patient's right atrium from an inferior vena cava, thereby reducing a risk of emboli entrained in flow from the inferior vena cava being directed into the second end of the conduit.

12. The device of claim 8, wherein the lumen has a diameter in the neck region in a range of 5 mm to 6.5 mm.

13. The method of claim 8, wherein the lumen of the conduit is configured to provide high velocity flow therethrough, while limiting paradoxical emboli passing across the lumen during a transient pressure gradient reversal.

14. The device of claim 8, wherein the conduit comprises a layer of biocompatible material.

15. The device of claim 8, wherein the first expandable end region, in the expanded deployed state, forms a filter that prevents emboli from entering the second end of the conduit.

16. The device of claim 1, further comprising a plurality of longitudinal struts interconnected by a plurality of circumferential sinusoidal struts.

17. An asymmetric device for regulating blood volume distribution across a patient's atrial septum, the device comprising:

a first expandable end region configured to transition from a contracted delivery state to an expanded deployed state in which the first expandable end region extends into the patient's left atrium and an inlet end of the first expandable end region has a circular cross-sectional shape in the expanded state;

a second expandable end region configured to transition from a contracted delivery state to an expanded deployed state in which the second expandable end region extends into the patient's right atrium and an outlet end of the second expandable end region has a cross-sectional shape in the expanded state having a first pair of opposing sides that extend parallel and a second pair of opposing ends that curve; and a neck region joining the first expandable end region to the second expandable end region, the neck region configured for placement in the patient's atrial septum.

18. The device of claim 17, wherein the inlet end of the first expandable end region in the expanded state is in a first plane, and the outlet end of the second expandable end region in the expanded state is in a second plane, and wherein the first plane intersects the second plane.

19. The device of claim 17, further comprising a central longitudinal axis, wherein from a first profile of the device having a first orientation, the central longitudinal axis has a curved shape.

20. The device of claim 19, wherein at the second orientation of the second profile of the device, one of the first pair of opposing sides that extend parallel of the cross-sectional shape of the second expandable end region in the expanded state is closest to the first expandable end region.

* * * * *